(12) United States Patent
Olhoft et al.

(10) Patent No.: US 8,541,653 B2
(45) Date of Patent: Sep. 24, 2013

(54) TRANSFORMATION OF SOYBEAN

(75) Inventors: Paula Olhoft, Morrisville, NC (US);
Leslie Grist, Raleigh, NC (US); Libby Bernal, Morrisville, NC (US); Sara Price, Raleigh, NC (US); Diana Arias, Cary, NC (US); Haiping Hong, Morrisville, NC (US)

(73) Assignee: BASF Plant Science GmbH, Ludwigshafen (DE)

( * ) Notice: Subject to any disclaimer, the term of this patent is extended or adjusted under 35 U.S.C. 154(b) by 1635 days.

(21) Appl. No.: 11/628,689

(22) PCT Filed: Jun. 4, 2005

(86) PCT No.: PCT/EP2005/006012
§ 371 (c)(1),
(2), (4) Date: Dec. 6, 2006

(87) PCT Pub. No.: WO2005/121345
PCT Pub. Date: Dec. 22, 2005

(65) Prior Publication Data
US 2009/0049567 A1 Feb. 19, 2009

Related U.S. Application Data

(60) Provisional application No. 60/577,708, filed on Jun. 7, 2004, provisional application No. 60/621,702, filed on Oct. 25, 2004, provisional application No. 60/629,138, filed on Nov. 18, 2004.

(51) Int. Cl.
*C12N 15/84* (2006.01)
*A01H 4/00* (2006.01)

(52) U.S. Cl.
USPC ........... 800/294; 800/300; 800/312; 435/426; 435/430; 435/431; 435/469

(58) Field of Classification Search
None
See application file for complete search history.

(56) References Cited

U.S. PATENT DOCUMENTS

| | | | |
|---|---|---|---|
| 5,322,783 A | 6/1994 | Tomes et al. | |
| 5,376,543 A * | 12/1994 | Chee et al. | 800/294 |
| 6,384,301 B1 | 5/2002 | Martinell et al. | |
| 6,649,812 B1 | 11/2003 | Knittel et al. | |
| 2001/0034888 A1 | 10/2001 | Olhoft et al. | |
| 2003/0046733 A1 | 3/2003 | Dias | |

FOREIGN PATENT DOCUMENTS

| WO | WO-95/06741 | 3/1995 |
|---|---|---|
| WO | WO-2006/024509 | 3/2006 |

OTHER PUBLICATIONS

Kim et al. Journal of Plant Physiology 136: 664-669 (1990).*
Xiang et al. Hereditas (Beijing) 23(4): 336-340 (2001).*
Wright et al. Plant Cell Reports 5: 150-154 (1986).*
Birch et al. Ann. Rev. Plant Physiol. Plant Mol. Biol. 48: 297-326 (1997).*
Wu et al. Plant Cell Reports 21: 659-668 (2003).*
Somers et al. Plant Physiology 131: 892-899 (2003).*
Everat-Bourboulox, A. Physiol. Plantarum 70: 648-652 (1987).*
Long et al. Development 125: 3027-3035 (1998).*
Zhang, Z. et al., "The Use of Glufosinate as a Selective Agent in *Agrobacterium*-mediated Transformation of Soybean", Plant Cell, Tissue and Organ Culture 56 (1999), pp. 37-46.
Bechtold, N. et al., "In Planta *Agrobacterium*-Mediated Transformation of Adult *Arabidopsis thaliana* Plants by Vacuum Infiltration", Methods in Molecular Biology, 82 (1998), pp. 259-266.
Parrott, W. A. et al., "Recovery and Evaluation of Soybean Plants Transgenic for a *Bacillus thuringiensis* var. *Kurstaki* Insecticidal Gene", In Vitro Cell. Dev. Biol. 30P (1994), pp. 144-149.
Stewart, Jr., C. N. et al., "Genetic Transformation, Recovery, and Characterization of Fertile Soybean Transgenic for a Synthetic *Bacillus thuringiensis crylAc* Gene", Plant Physiol. 112 (1996), pp. 121-129.
Hadi, M. Z. et al., "Transformation of 12 Different Plasmids into Soybean via Particle Bombardment", Plant Cell Reports 15 (1996), pp. 500-505.
Maughan, P.J. et al., "Biolistic Transformation, Expression, and Inheritance of Bovine β-Casein in Soybean (*Glycine max*)", In Vitro Cell. Dev. Biol.—Plant 35 (1999), pp. 344-349.
Samoylov, V.M. et al., "A Liquid-Medium-Based Protocol for Rapid Regeneration from Embryogenic Soybean Cultures", Plant Cell Reports 18 (1998), pp. 49-54.
McCabe, D.E. et al., "Stable Transformation of Soybean (*Glycine max*) by Particle Acceleration", Bio/Technology 6 (1988), pp. 923-926.
Simmonds, D.H. et al., "Genotype Screening for Proliferative Embryogenesis and Biolistic Transformation of Short-Season Soybean Genotypes", Plant Cell Reports 19 (2000), pp. 485-490.
Bailey, M.A. et al., "Inheritance of *Agrobacterium tumefaciens*-Induced Tumorigenesis of Soybean", Crop Science 34 (1994), pp. 514-519.
Bailey, M.A. et al., "Genotype Effects on Proliferative Embryogensis and Plant Regeneration of Soybean", In Vitro Cell. Dev. Biol. 29P (1993), pp. 102-108.
Aragão, F.J.L. et al., "Selection of Transgenic Meristematic Cells Utilizing a Herbicidal Molecule Results in the Recovery of Fertile Transgenic Soybean [*Glycine max* (L.) Merril] Plants at a High Frequency", Theor. Appl. Genet. 101 (2000), pp. 1-6.
Manickavasagam, M. et al., "*Agrobacterium*-mediated Genetic Transformation and Development of Herbicide-Resistant Sugarcane (*Saccharum* species hybrids) Using Axillary Buds", Plant Cell Rep. 23 (2004), pp. 134-143.
Kinney, A.J. et al., "Modifying Soybean Oil for Enhancing Performance in Biodiesel Blends", Fuel Processing Technology 86 (2005), pp. 1137-1147.

(Continued)

*Primary Examiner* — David T Fox
(74) *Attorney, Agent, or Firm* — Novak Druce Connolly Bove + Quigg LLP

(57) ABSTRACT

The present invention relates to improved methods for the incorporation of DNA into the genome of a soybean (*Glycine max*) plant utilizing meristematic cells of primary or higher leaf nodes as target tissue by means of *Agrobacterium*-mediated transformation and subsequent regeneration of the transformed cells into a whole plant.

18 Claims, 17 Drawing Sheets

(56) References Cited

OTHER PUBLICATIONS

Figure 1:
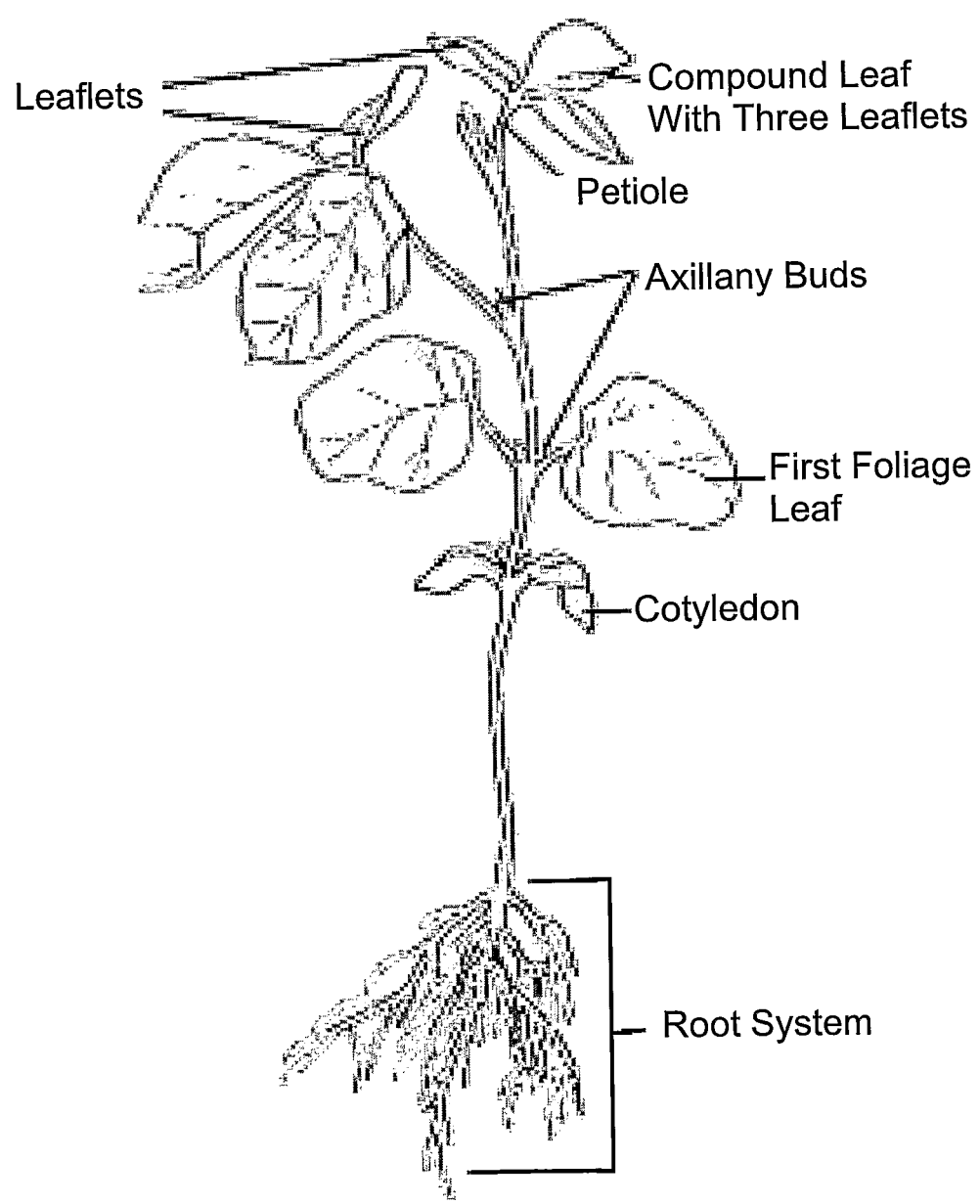

Dayal, S. et al., "An Efficient Protocol for Shoot Regeneration and Genetic Transformation of Pigeonpea (*Cajanus cajan* (L.) Millsp.] Using Leaf Explants", Plant Cell Rep. 21 (2003), pp. 1072-1079.

Kado, C. I., "Molecular Mechanisms of Crown Gall Tumorigenesis", Critical Reviews in Plant Sciences vol. 10, No. 1 (1991), pp. 1-32.

Olhoft, P.M. et al., "Efficient Soybean Transformation Using Hygromycin B Selection in the Cotyledonary-node Method", Planta 216 (2003), pp. 723-735.

Olhoft, P.M. et al., "L-Cysteine Increases *Agrobacterium*-mediated T-DNA Delivery into Soybean Cotyledonary-node Cells", Plant Cell Rep. 20 (2001), pp. 706-711.

Cho, H-J. et al., "High-Efficiency Induction of Soybean Hairy Roots and Propagation of the Soybean Cyst Nematode", Planta 210 (2000), pp. 195-204.

Lazo, G.R. et al., "A DNA Transformation-Competent *Arabidopsis* Genomic Library in *Agrobacterium*", Bio/Technology 9 (1991), pp. 963-967.

Horsch, R.B. et al., "A Simple and General Method for Transferring Genes into Plants", Science 227 (1985), pp. 1229-1231.

Trieu, A.T. et al., "Transformation of *Medicago truncatula* via Infiltration of Seedlings or Flowering Plants with *Agrobacterium*", The Plant Journal vol. 22, No. 6 (2000), pp. 531-541.

Sato, S. et al., "Stable Transformation via Particle Bombardment in Two Different Soybean Regeneration Systems", Plant Cell Reports 12 (1993), pp. 408-413.

Hinchee, M.A.W. et al., "Production of Transgenic Soybean Plants Using *Agrobacterium*-Mediated DNA Transfer", Bio/Technology 6 (1988), pp. 915-922.

Finer, J.J. et al., "Apical Proliferation of Embryogenic Tissue of Soybean [*Glycine max* (L.) Merrill]", Plant Cell Reports 7 (1988), pp. 238-241.

Ko, T.-S. et al., "Two Critical Factors are Required for Efficient Transformation of Multiple Soybean Cultivars: *Agrobacterium* Strain and Orientation of Immature Cotyledonary Explant", Theor. Appl. Genet. 107 (2003), pp. 439-447.

Yan, B. et al., "*Agrobacterium tumefaciens*—Mediated Transformation of Soybean [*Glycine max* (L.) Merrill.] Using Immature Zygotic Cotyledon Explants", Plant Cell Reports 19 (2000), pp. 1090-1097.

Ko, T.-S. et al., "A Partially Disarmed vir Helper Plasmid, pKYRT1, in Conjunction with 2,4-dichlorophenoxyactic Acid Promotes Emergence of Regenerable Transgenic Somatic Embryos from Immature Cotyledons of Soybeans", Planta 218 (2004), pp. 536-541.

Finer, J.J. et al., "Transformation of Soybean via Particle Bombardment of Embryogenic Suspension Culture Tissue", In Vitro Cell. Dev. Biol. 27P (1991), pp. 175-182.

Parrott, W.A. et al., "Recovery of Primary Transformants of Soybean", Plant Cell Reports 7 (1989), pp. 615-617.

Finer, J.J. et al., "Development of an Embryogenic Suspension Culture of Soybean (*Glycine max* Merrill.)", Plant Cell, Tissue and Organ Culture 15 (1988), pp. 125-136.

Trick, H.N. et al., "Recent Advances in Soybean Transformation", Plant Tissue Culture and Biotechnology vol. 3, No. 1 (1997), pp. 9-26.

\* cited by examiner

A

B

C

D

E

TRANSFORMATION OF SOYBEAN

RELATED APPLICATIONS

This application is a national stage application (under 35 U.S.C. 371) of PCT/EP2005/006012 filed Jun. 4, 2005, which claims benefit of U.S. Provisional application 60/577,708 filed Jun. 7, 2004, U.S. Provisional application 60/621,702 filed Oct. 25, 2004, and U.S. Provisional application 60/629,138 filed Nov. 18, 2004.

FIELD OF THE INVENTION

The present invention relates to improved methods for the incorporation of DNA into the genome of a soybean (*Glycine max*) plant utilizing meristematic cells of primary or higher leaf nodes as target tissue by means of *Agrobacterium*-mediated transformation and subsequent regeneration of the transformed cells into a whole plant.

BACKGROUND OF THE INVENTION

The soybean (*Glycine max*) belongs to the *Fabaceae* (*Leguminosae*) family. This plant family is identified by having its seed borne in a legume (pod). The soybean is thought to have originated in China. Wild types of soybeans are viny in nature, which probably is a major reason why soybeans were first introduced in the United States as a hay crop. Introductions from China, Manchuria, Korea and Japan have been important in developing varieties for the United States. Modern breeding efforts to improve the agronomic traits, such as more erect growth, reduced lodging and increased seed size, have been primarily responsible for the development of soybeans into a crop of world-wide importance. The acreage and the proportion of the crop harvested for grain has increased steadily and today soybeans are a major world commodity.

Cultivated soybean has a substantial commercial value throughout the world. Over 50 million hectares worldwide are used to produce an annual crop of soybeans in excess of 100 metric tons with an estimated value exceeding 20 billion dollars. The development of scientific methods useful in improving the quantity and quality of this crop is, therefore, of significant commercial interest.

Soybeans are widely used as a source of protein, oil, condiments and chemical feed-stock. Significant effort has been expended to improve the quality of cultivated soybean species by conventional plant breeding, and a number of major successes are recorded. The methods of conventional plant breeding have been limited, however, to the movement of genes and traits from one soybean variety to the other.

Modern biotechnological research and development has provided useful techniques for the improvement of agricultural products by plant genetic engineering. Plant genetic engineering involves the transfer of a desired gene or genes into the inheritable germ-line of crop plants such that those genes can be bred into or among the elite varieties used in modern agriculture. Gene transfer techniques allow the development of new classes of elite crop varieties with improved disease resistance, herbicide tolerance, and increased nutritional value. Various methods have been developed for transferring genes into plant tissues including high velocity microprojection, microinjection, electroporation, direct DNA uptake, and *Agrobacterium*-mediated gene transformation. *Agrobacterium*-mediated gene transformation is the most widely used gene transfer technique in plants. This technique takes advantage of the pathogenicity of the soil dwelling bacterium *Agrobacterium tumefaciens*. *Agrobacterium tumefaciens* natively has the ability to transfer a portion of its DNA, called T-DNA, into the genome of the cells of a plant to induce those cells to produce metabolites useful for the bacterium's nutrition. *Agrobacterium*-mediated transformation takes advantage of this concept by replacing the T-DNA of an *Agrobacterium* with a foreign set of genes, thus, making the bacterium a vector capable of transferring the foreign genes into the genome of the plant cell. Typically, the foreign gene construct that is transferred into the plant cell involves a specific gene of interest, which is desired to be introduced into the germline of the plant, coupled with a selectable marker that confers upon the plant cell a resistance to a chemical selection compound. Typically, the *Agrobacterium*-mediated gene transfer is into an undifferentiated cell cultivated in tissue culture, known as a callus cell, or the transfer is made into a differentiated plant cell from a leaf or stem, which is then induced to become an undifferentiated callus culture.

The development of a method for introducing foreign genes into soybean species greatly enhanced the range of traits which could be imparted to soybeans. In order to obtain a system for useful gene introduction into soybeans, a number of obstacles had to be overcome. These include optimization of regeneration to whole plants of the target tissue, definition of the conditions (e.g., time, bacterial concentration, and media) for the co-cultivation of the soybean cells and *Agrobacterium* cells, and establishing an appropriate selection protocol.

However, DNA delivery using particle bombardment, electroporation, or *Agrobacterium*-mediated delivery into soybean has proven to be difficult. This is due, in part, to the small number of cells that have been found to be totipotent in soybean (Trick et al. (1997) Plant Tissue Cult Biotechnol 3:9-26). Methods that use *Agrobacterium* tumefaciens for DNA delivery have the additional problem of overcoming any incompatibility between the soybean explant and the *Agrobacterium*. Two methods routinely used are an *Agrobacterium*-based method targeting the cotyledonary-node axillary meristems (Hinchee et al. (1988) Bio/Technology 6:915-922) and a method using particle bombardment of mature zygotic embryos (Finer and McMullen (1991) In Vitro Cell Dev Biol 27P: 175-182).

Described are methods based on somatic embryogenesis: Embryos are induced from immature soybean cotyledons by placing the explant on high levels of 2,4-D (40 mg/L) and the embryogenic tissues are subsequently proliferated on induction medium (Finer (1988) Plant Cell Rep 7:238-241) or liquid suspension culture (Finer and Nagasawa (1988) Plant Cell Tissue Organ Cult 15:125-136).

Further described are methods based on *Agrobacterium*-mediated transformation of zygotic immature cotyledons (Parrott et al. (1989) Plant Cell Rep 7:615-617; Yan et al. (2000) Plant Cell Rep 19:1090-1097; Ko et al. (2003) Theor Appl Genet. 107:439-447). However, in Parrott et al. the three plants produced were chimeric, from a multicellular origin, and did not transmit the transgene to the next generation. Yan et al. (2000) Plant Cell Rep 19:1090-1097 reported a low transformation frequency of 0.03%. Plant produced transmitted the transgene into the next generation, presumably due to the continuous selection of transformed primary embryos for the production of secondary embryos thereby resulting in non-chimeric plants. Recently, Ko et al. (2003) Theor Appl Genet. 107:439-447 has reported the recovery of transgenic plants at 1.7% transformation frequencies, however, the method relies on using a partially disarmed (oncogenic) *Agrobacterium* strain, pKYRT, with a functional TR-DNA sequence in order to stimulate embryogenesis (Ko et al.

(2004) Planta 218:536-541). These methods use the immature cotyledons as the target tissue with subsequent proliferation and selection on solid medium.

Other methods for soybean transformation are based on particle bombardment trans-formation of proliferative embryogenic cultures. Fertile transgenic soybean plants have been produced using particle bombardment (Finer and McMullen (1991) In Vitro Cell Dev Biol 27P:175-182; Sato et al. (1993) Plant Cell Rep 12:408-413; Parrott et al. (1994) In Vitro Cell Dev Biol 30P:144-149; Hadi et al. (1996) Plant Cell Rep 15:500-505; Stewart et al. (1995) Plant Physiol 112:121-129; Maughan et al. (1999) In Vitro Cell Dev Biol-Plant 35:334-349). In these methods, the proliferative embryogenic cultures from both liquid and solid media are used for particle bombardment and immediate selection occurs while on solid or liquid media.

The above-described methods based on embryogenic cultures have one or more of the following disadvantages:
1. A continual supply of greenhouse grown plants are needed to supply the immature cotyledons for establishment of embryogenic cultures and induction of embryo-genesis.
2. For microprojectile bombardment, induction of somatic embryos occurs for at least 90 d on solid or liquid medium before bombardment. After bombardment, the embryos are transferred to medium with selection up to 4 weeks, or when embryos elongate. Surviving embryogenic clusters are transferred to maturation medium for a minimum of 4 weeks. The mature embryos are then desiccated for 2 to 7 days then plated onto germination medium for 3 to 4 weeks. After embryos develop shoots and roots, they are transferred to Magenta boxes for 2 to 3 weeks before transferring to greenhouse. This process takes approximately 9 months to one year.
3. For *Agrobacterium* infection, the immature cotyledons are used as the target material thereby decreasing the time by 3 months. However, to produce non-chimeric plants, production of secondary embryos from transgenic primary embryos is needed before desiccation of mature embryos to induce germination of plantlets.
4. Sterility with somatic embryogenesis and particle bombardment is a problem (Samoylov et al. (1998) Plant Cell Rep 18:49-54). This is mainly due to the length of time in culture (see above).
5. The induction of somatic embryos and the formation of proliferative embryogenic cultures are highly genotype-dependent (Bailey et al. (1993) In Vitro Cell Dev Biol 29P:102-108; Bailey et al. (1993) Crop Sci 34:514-519; Simmonds and Donaldson (2000) Plant Cell Rep 19:485-490).

Other methods for soybean transformation are employing the embryo axes as target tissue. Methods for particle bombardment transformation of immature embryonic axes are disclosed (McCabe et al. (1988) Bio/Technology 6:923-926; Aragao et al. (2000) Theor Appl Genet. 101:1-6). The embryos of mature, sterile seeds are excised and the apical meristem exposed by removing the primary leaves. After bombardment of the apical meristem, the explants are moved to shoot induction medium overnight and the explants are transferred to recovery plus selection medium for 2 weeks before elongated shoots begin to emerge. After 3 to 4 weeks additional shoots regenerate. A total of 5 to 7 shoots regenerate in total, and in Aragao et al. (2000), only 10% of those shoots elongated. Transformation efficiency from 0.1 to 20.1%. This group used ahas (acetohydroxyacid synthase) for selection of transgenic cells while the protocol from McCabe et al. (1988) Bio/Technology 6:923-926 no selection is applied. *Agrobacterium* mediated transformation of immature embryo axes is further described in US 20030046733 and U.S. Pat. No. 6,384,301 with a 1 to 3% transformation efficiency. The protocol is similar to above, but instead of bombardment, *Agrobacterium* is applied and a co-cultivation step included. Also, pretreatment of seeds with hormones is claimed.

Other methods related to transformation of the cotyledonary-node, e.g. by particle bombardment (U.S. Pat. No. 5,322,783). The cotyledonary node is targeted after excising the meristem from imbibed seeds, a pretreatment with cytokinins for 1 day, and a preculture on sucrose medium for an additional day. In this patent no transformed plants are presented. Presumably this method would be difficult to access the cells for particle bombardment. Transformed plants have been reported by using *Agrobacterium tumefaciens* infection of the cotyledonary-node (Hinchee et al. (1988) Bio/Technology 6:915-922; Zhang et al. (1999) Plant Cell Tissue Organ Cult 56:37-46; Olhoft and Somers (2001) Plant Cell Rep 20:706-711; Olhoft et al. (2003) Planta 216:723-735). Explants are prepared from 5-day-old seedlings and exposed to *Agrobacterium tumefaciens*. After co-cultivation, shoots are induced for 4 weeks under selection. Elongation of transformed shoots begins as early as 4 to 6 weeks on elongation medium and continues for 6 months. Transformed shoots are rooted on rooting medium for 5 to 7 days before transferring to the greenhouse.

Although some of the problems linked to the transformation of soybeans have been overcome by the methods described in the art, there is still a significant need for improvement, since all methods known so far have only a low to moderate transformation and—especially—regeneration efficiency. Although significant advances have been made in the field of *Agrobacterium*-mediated transformation methods, a need continues to exist for improved methods to facilitate the ease, speed and efficiency of such methods for transformation of soybean plants. Therefore, it was the objective of the present invention to provide an improved method having higher overall efficiency in the process of generation of transgenic soybean plants. This objective is solved by the present invention.

SUMMARY OF THE INVENTION

This invention uses *Agrobacterium*, including *Agrobacterium tumefaciens*, for T-DNA delivery into meristematic cells located in primarily the first leaf-node, all other higher leaf nodes and the regeneration into mature transgenic plants. These target tissues are infected directly at the seedling stage with *Agrobacterium*.

Accordingly a first embodiment of the invention related to a method for producing a transgenic soybean plant comprising the steps of:
(a) providing an axillary meristematic tissue of a primary or higher leaf node of a soybean seedling, and
(b) co-cultivating said axillary meristematic tissue with an *Agrobacterium* comprising a transgenic T-DNA, said transgenic T-DNA comprising at least one plant expression cassette for an agronomically valuable trait, and—optionally—one or more selectable marker genes, and
(c) transferring said co-cultivated axillary meristematic tissue on a shoot induction medium comprising
  (i) at least one plant growth factor in a concentration suitable to induce de novo shoot induction from said axillary meristematic tissue, and
  (ii) optionally one or more selection compounds which in combination with the selectable marker gene of (b)

allow for identification and/or selection of a plant cell, tissue or plant comprising said selectable marker gene, and/or (iii) optionally one or more antibiotics suitable to inhibit *Agrobacterium* growth, and cultivating said co-cultivated axillary meristematic tissue until shoots are induced and developed therefrom and isolating said shoots, and (d) transferring said isolated shoots to a rooting medium and cultivating said shoots on said rooting medium until said shoots have formed roots, and further regenerating the so derived plantlets into mature plants, which comprise inserted into their genome a T-DNA comprising said at least one plant expression cassette for an agronomically valuable trait, and—optionally—said at least one selectable marker gene.

Preferably the method of the invention comprises one or more additional steps selected from the group of:

(a1) wounding the explant prior to, during or immediately after co-cultivation, and (b1) transferring said co-cultivated axillary meristematic tissue after step (b) to a medium comprising at least one antibiotic suitable to inhibit *Agrobacterium* growth, and—optionally—at least one plant growth factor, wherein said medium is preferably lacking a selection compound which in combination with the selectable marker gene of (b) would allow for identification and/or selection of plant cells, organs or plants comprising said selectable marker gene, and, (b2) further incubating said axillary, meristematic tissue after step (b) and—optionally (b1)—on a shoot induction medium (SIM) comprising at least one plant growth factor, wherein said shoot induction medium is preferably lacking a selection compound which in combination with the selectable marker gene of (b) would allow for identification and/or selection of plant cells, organs or plants comprising said selectable marker gene, and (c1) transferring said shoots after step (c) to a shoot elongation medium comprising (i) at least one plant growth factor in a concentration suitable to allow shoot elongation, and (ii) optionally one or more selection compounds which in combination with the selectable marker gene of (b) allow for identification and/or selection of a plant cell, tissue or plant comprising said selectable marker gene, and cultivating said transferred shoots on said shoot elongation medium until said shoots have elongated to a length of at least about 2 cm.

Figure 3:

The axillary meristematic tissue of the primary or higher node can be provided in various forms:

a) Method A: Seedling axillary meristem: The entire seedling or a substantial part thereof (such as the seedling minus roots or the seedling without one or both cotyledons) can be employed, inoculated with *Agrobacterium* and placed on shoot induction medium (SIM). Preferably the substantially entire seedling is selected from the group of material consisting of i) an entire seedling, and
ii) a seedling having the roots removed, and
iii) a seedling having one or both cotyledons removed, and
iv) a seedling having the roots and one or both cotyledons removed, and
v) a seedling having the roots, both cotyledons and part of the epicotyl removed leaving the axillary meristem attached to part of the epicotyl.

b) Method B: Leaf axillary meristem: The primary or higher leaves are dissected in a way that the axillary meristematic tissue remains attached to the petioles of the leafs, dipped in *Agrobacterium* solution, co-cultivated on co-cultivation medium, and placed on the shoot induction medium (SIM).

c) Method C: Propagated axillary meristem: From a germinated (preferably about) 7-day old seedling the hypocotyl and one and a half or part of both cotyledons are removed from each seedling. The seedlings are then placed on propagation media for 2 to 4 weeks. One shoot is derived from growth of the main apical bud and—occasionally—one growth from each axillary bud at the cotyledonary node. Each shoot grows approximately 7 cm in length and contains 3 to 6 shorted internodes to obtain explants from (FIG. 3). Axillary nodes from the first to the fourth leaf node can be excised. An average of three to four explants can be obtained from each seedling.

Beside the explicitly mentioned sources (Method A, B, C) point out above, other sources may be suitable for the axillary meristematic tissue. These sources may for example be more restricted explants derived from a soybean seedling such as only the epicotyl and the primary leaf node. Obviously such restricted (i.e. small) explants can not only be obtained from the primary node but also from higher nodes as well (e.g., secondary and higher nodes).

The soybean seedling presenting the source for the axillary meristematic tissue explant generation is preferably germinated for about 4 to 10 days prior to explant generation. The present invention provides a novel and efficient method of performing germline transformation of soybean using *Agrobacterium*-mediated transformation directly on axillary meristematic cells of a primary or higher leaf node of soybean seedling. Direct shoot induction from transformed axillary meristematic cells results in germline transgenic plants. The overall process is rapid and efficient. One significant aspect of this invention is that the reduction of the pretreatment period of soybean seeds has improved the shoot production in surviving explants as well as reduced the time taken to produce plants that are transferable to a greenhouse. Also, the reduction of time and materials provides a system that is economically beneficial to those who implement it. The method of the invention is not requiring a step of callus culture, which is known in the art to highly cultivar dependent (especially in the regeneration step). In consequence, because axillary meristematic cells are present in all soybean cultivars and virtually have all a similar regeneration capacity, the method of the invention can be used on any soybean variety and cultivar.

Various *Agrobacterium* strains can be employed. Both *Agrobacterium tumefaciens* and *Agrobacterium rhizogenes* strains can be used. In a preferred embodiment "disarmed" strains (i.e., for which the tumor- or hair root phenotype inducing genes have been deleted) are utilized. An especially preferred *Agrobacterium rhizogenes* strain is a disarmed *Agrobacterium rhizogenes* strain K599 or a derivative thereof. Such strains are described in U.S. provisional application No. 60/606,789, filed Sep. 2, 2004, hereby incorporated entirely by reference.

In a preferred embodiment of the invention, the axillary meristematic tissue is wounded prior to inoculation with *Agrobacterium*.

In another preferred embodiment, the media of at least one of step (b), (b1), (b2), and/or (c), comprises a cytokinin (like e.g., 6-benzylaminopurine (BAP)). Preferably the concentration is between about 1 µM and about 10 µM 6-benzylaminopurine (BAP).

It is furthermore especially preferred, that the media of at least one of step (b), (b1), (b2), (c) and/or (c1), preferably at least (b) and (c1), comprises between about 0.1 µM and about 2 µM Gibberellic acid (GA3).

In another preferred embodiment, the media of at least one of step (b), (b1), (b2), and (c), preferably at least (b) comprises least one thiol compound, preferably selected from the group consisting of sodium thiolsulfate, dithiotrietol (DTT) and cysteine. Preferably the concentration is between about 1 mM and 10 mM of L-Cysteine, 0.1 mM to 5 mM DTT, and/or 0.1 mM to 5 mM sodium thiolsulfate.

In another preferred embodiment of the invention, the media of at least one of step (c1) and/or (d) comprises between about 0.01 mg/l and about 1 µM mg/l indole acetic acid (IAA), and/or between about 0.1 µM and about 4 µM Gibberellic acid (GA3), and/or between about 0.5 µM and about 6 µM zeatin riboside acid.

Other objects, advantages, and features of the present invention will become apparent from the following specification.

GENERAL DEFINITIONS

Abbreviations: BAP—6-benzylaminopurine; 2,4-D—2,4-dichlorophenoxyacetic acid; MS—Murashige and Skoog medium (Murashige T and Skoog F (1962) Physiol. Plant. 15, 472-497); NAA—1-naphtaleneacetic acid; MES, 2-(N-morpholino-ethanesulfonic acid, IAA indole acetic acid; IBA: indole butyric acid; Kan: Kanamycin sulfate; GA3-Gibberellic acid; Timentin™: ticarcillin disodium/clavulanate potassium.

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention, which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent, more preferably 5 percent up or down (higher or lower).

As used herein, the word "or" means any one member of a particular list and also includes any combination of members of that list.

The term "nucleic acid" refers to deoxyribonucleotides or ribonucleotides and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "polynucleotide".

The phrase "nucleic acid sequence" as used herein refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid which is transcribed and translated in a sequence-specific manner to produce into a particular polypeptide or protein when placed under the control of appropriate regulatory sequences. The coding region is said to encode such a polypeptide or protein.

The term "antisense" is understood to mean a nucleic acid having a sequence complementary to a target sequence, for example a messenger RNA (mRNA) sequence the blocking of whose expression is thought to be initiated by hybridization with the target sequence.

The term "sense" is understood to mean a nucleic acid having a sequence which is homologous or identical to a target sequence, for example a sequence which binds to a protein transcription factor and which is involved in the expression of a given gene. According to a preferred embodiment, the nucleic acid comprises a gene of interest and elements allowing the expression of the said gene of interest.

The term "gene" refers to a coding region operably joined to appropriate regulatory sequences capable of regulating the expression of the polypeptide in some manner. A gene includes untranslated regulatory regions of DNA (e.g., promoters, enhancers, repressors, etc.) preceding (up-stream) and following (downstream) the coding region (open reading frame, ORF) as well as, where applicable, intervening sequences (i.e., introns) between individual coding regions (i.e., exons).

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

The terms "polypeptide", "peptide", "oligopeptide", "polypeptide", "gene product", "expression product" and "protein" are used interchangeably herein to refer to a polymer or oligomer of consecutive amino acid residues.

The term "isolated" as used herein means that a material has been removed from its original environment. For example, a naturally occurring polynucleotide or polypeptide present in a living animal is not isolated, but the same polynucleotide or polypeptide, separated from some or all of the coexisting materials in the natural system, is isolated. Such polynucleotides can be part of a vector and/or such polynucleotides or polypeptides could be part of a composition, and would be isolated in that such a vector or composition is not part of its original environment.

The term "wild-type", "natural" or of "natural origin" means with respect to an organism, polypeptide, or nucleic acid sequence, that said organism is naturally occurring or available in at least one naturally occurring organism which is not changed, mutated, or otherwise manipulated by man.

The term "transgenic" or "recombinant" as used herein (e.g., with regard to a soybean cell or plant) is intended to refer to cells and/or plants that have incorporated exogenous genes or DNA sequences, including but not limited to genes or DNA sequences which are perhaps not normally present, genes not normally transcribed and translated ("expressed") in a given cell type, or any other genes or DNA sequences which one desires to introduce into the non-transformed cell and/or plant, such as genes which may normally be present in the non-transformed cell and/or plant but which one desires to have altered expression. Preferably, the term "recombinant" with respect to nucleic acids as used herein means that the nucleic acid is covalently joined and adjacent to a nucleic acid to which it is not adjacent in its natural environment. "Recombinant" poly-peptides or proteins refer to polypeptides or proteins produced by recombinant DNA techniques, i.e., produced from cells transformed by an exogenous recombinant DNA construct encoding the desired polypeptide or protein. Recombinant nucleic acids and polypeptide may also comprise molecules which as such does not exist in nature but are modified, changed, mutated or otherwise manipulated by man.

A "recombinant polypeptide" is a non-naturally occurring polypeptide that differs in sequence from a naturally occurring polypeptide by at least one amino acid residue. Preferred methods for producing said recombinant polypeptide and/or nucleic acid may comprise directed or non-directed mutagenesis, DNA shuffling or other methods of recursive recombination.

The terms "heterologous nucleic acid sequence" or "heterologous DNA" are used inter-changeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed.

The "efficiency of transformation" or "frequency of transformation" as used herein can be measured by the number of transformed cells (or transgenic organisms grown from individual transformed cells) that are recovered under standard experimental conditions (i.e. standardized or normalized with respect to amount of cells contacted with foreign DNA, amount of delivered DNA, type and conditions of DNA delivery, general culture conditions etc.). For example, when isolated petioles are used as starting material for transformation, the frequency of transformation can be expressed as the number of transgenic shoots (or resulting plant lines) obtained per inoculated petiole.

The term "cell" refers to a single cell. The term "cells" refers to a population of cells. The population may be a pure population comprising one cell type. Likewise, the population may comprise more than one cell type. In the present invention, there is no limit on the number of cell types that a cell population may comprise. The cells may be synchronize or not synchronized, preferably the cells are synchronized.

The term "chromosomal DNA" or "chromosomal DNA-sequence" is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., PCR analysis, Southern blot analysis, fluorescence in situ hybridization (FISH), and in situ PCR.

The term "structural gene" as used herein is intended to mean a DNA sequence that is transcribed into mRNA which is then translated into a sequence of amino acids characteristic of a specific polypeptide.

The term "expression" refers to the biosynthesis of a gene product. For example, in the case of a structural gene, expression involves transcription of the structural gene into mRNA and—optionally—the subsequent translation of mRNA into one or more polypeptides.

The term "expression cassette" or "expression construct" as used herein is intended to mean the combination of any nucleic acid sequence to be expressed in operable linkage with a promoter sequence and—optionally—additional elements (like e.g., terminator and/or polyadenylation sequences) which facilitate expression of said nucleic acid sequence.

The term "promoter" as used herein is intended to mean a DNA sequence that directs the transcription of a DNA sequence (e.g., a structural gene). Typically, a promoter is located in the 5'-region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter. Also, the promoter may be regulated in a tissue-specific or tissue preferred manner such that it is only active in transcribing the associated coding region in a specific tissue type(s) such as leaves, roots or meristem.

The term "operable linkage" or "operably linked" is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. Operable linkage, and an expression cassette, can be generated by means of customary recombination and cloning techniques as described (e.g., in Ausubel F M et al. (1987) Current Protocols in Molecular Biology, Greene Publishing Assoc. and Wiley Interscience; Maniatis T, Fritsch E F and Sambrook J (1989) Molecular Cloning: A Laboratory Manual, 2nd Ed., Cold Spring Harbor Laboratory, Cold Spring Harbor (NY); Gelvin et al. (Eds) (1990) Plant Molecular Biology Manual; Kluwer Academic Publisher, Dordrecht, The Netherlands; Silhavy T J, Berman M L and Enquist L W (1984) Experiments with Gene Fusions, Cold Spring Harbor Laboratory, Cold Spring Harbor (NY)). However, further sequences which, for example, act as a linker with specific cleavage sites for restriction enzymes, or as a signal peptide, may also be positioned between the two sequences. The insertion of sequences may also lead to the expression of fusion proteins. Preferably, the expression cassette, consisting of a linkage of promoter and nucleic acid sequence to be expressed, can exist in a vector-integrated form and be inserted into a plant genome, for example by transformation.

The term "transformation" includes introduction of genetic material into plant cells, preferably resulting in chromosomal integration and stable heritability through meiosis. Transformation also includes introduction of genetic material into plant cells in the form of plant viral vectors involving epichromosomal replication and gene expression which may exhibit variable properties with respect to meiotic stability.

The terms "meristem" or "meristematic cells" or meristematic tissue" can be used interchangeable and are intended to mean undifferentiated plant tissue, which continually divides, forming new cells, as that found at the tip of a stem or root.

The term "node" or "leaf node" is intended to mean the point on a stem where a leaf is attached or has been attached. The term "internode" is intended to mean the section or part between two nodes on a stem.

The term "petiole" is intended to mean the stalk by which a leaf is attached to a stem, also called a leaf-stalk.

The term "axillary bud" is intended to mean a small protuberance along a stem or branch, sometimes enclosed in protective scales and containing an undeveloped shoot, leaf, or flower; also called a lateral bud.

The term "hypocotyl" is intended to mean the part of the stem between the seed leaves (the cotyledons) and the root.

The term "leaf axil" is intended to mean the angle between a leaf and the stem on which it is borne. The axillary bud occurs at the leaf axil.

The term "cotyledon" is intended to mean a leaf of the embryo of a seed plant, which upon germination either remains in the seed or emerges, enlarges, and becomes green; also called a seed leaf. The soybean seed consists of two seed halves, which are cotyledons or seed leaves. The two cotyledons contain food and nutrient reserves that nourish the seedling until it becomes established. Cotyledon color is green in the developing pod but in present grain varieties, it turns yellow as the plants mature. The embryo axis is located between the cotyledons and is attached to them near the end closest to the micropyle.

The germination process is initiated when the seed is exposed to a favorable environment including correct temperature, water and oxygen. The radicle is normally the first organ to break through the seedcoat in the process of soybean germination. It develops into the primary root of the soybean plant. After the radicle emerges from the seedcoat, it grows mainly downward and develops into the main taproot. Lateral branch roots develop from the taproot. Once the soybean seed has started the germination process, the hypocotyl [part of the stem between the radicle (the young primary root) and cotyledons] elongates and pulls the swollen cotyledons toward the soil surface. The seedcoat is usually sloughed by the time the cotyledons have emerged from the soil. Soon after the cotyledons emerge, the hypocotyl ceases to elongate and the crook (hypocotyledonary arch) straightens. The cotyledons then separate, exposing the epicotyl which starts to grow. The epicotyl at first consists of two unifoliolate leaves (leaves with only one leaflet) with a growing point located between them. The above-ground growth of the soybean plant originates from the epicotyl.

The stem, which develops from the epicotyl, is the primary supporting and translocating structure of the plant. Nodes of the main stem are rapidly formed, with only 4 to 5 weeks being required for formation of all nodes. A node can be identified by the presence of a leaf or branch from the main stem. Although the length of the internode (section between nodes) is genetically controlled, it is also modified by light, water, nutrients and other environmental factors. Branching from axillary buds occurs when the main stem apex can no longer suppress bud development.

Except at the cotyledonary and second nodes of the main stem, the soybean plant has a single trifoliolate leaf (a leaf with 3 leaflets) at each node alternately attached to each side of the stem. The two unifoliolate leaves (consisting of a petiole and a single leaflet) are attached opposite to each other at the second node. The first trifoliolate leaf is at the third node. The petiole attaches the leaf to the main stem or branch. A pair of lance-shaped modified leaves (stipules) are located at the base of the petiole in the petiole-stem junction. At the base of the petiole and at the base of each leaflet is a large group of cells called the pulvinus. Changes in the relative turgidity (water content) of the pulvinis causes the leaflets and petiole to assume different angles.

In each axil (junction of a stem and a branch or leaf) an axillary bud is present. This bud may develop into a branch, a flower cluster, or fail to develop, depending on the environment.

DETAILED DESCRIPTION OF THE INVENTION

The present invention is a method for the direct germline genetic transformation of varieties of soybean, *Glycine max*. This method is based on *Agrobacterium*-mediated gene delivery into individual soybean cells in the axillary meristem of primary or higher node of a germinated soybean. The transformed cells are then induced to form shoots that are, at a high frequency, germline soybean transformants that can be cultivated into whole sexually mature and fertile transgenic soybean plants. The method does not involve a phase of callus culture, and hence the time period of the entire process from seed to transgenic seed is remarkably concise.

Accordingly a first embodiment of the invention related to a method for producing a transgenic soybean plant comprising the steps of:
(a) providing an axillary meristematic tissue of a primary or higher leaf node of a soybean seedling, and
(b) co-cultivating said axillary meristematic tissue with an *Agrobacterium* comprising a transgenic T-DNA, said transgenic T-DNA comprising at least one plant expression cassette for an agronomically valuable trait, and—optionally—one or more selectable marker genes, and
(c) transferring said co-cultivated axillary meristematic tissue on a shoot induction medium comprising
  (i) at least one plant growth factor in a concentration suitable to induce de novo shoot induction from said axillary meristematic tissue, and
  (ii) optionally one or more selection compounds which in combination with the selectable marker gene of (b) allow for identification and/or selection of a plant cell, tissue or plant comprising said selectable marker gene, and/or
  (iii) optionally one or more antibiotics suitable to inhibit *Agrobacterium* growth, and cultivating said co-cultivated axillary meristematic tissue until shoots are induced and developed therefrom and isolating said shoots, and (d) transferring said isolated shoots to a rooting medium and cultivating said shoots on said rooting medium until said shoots have formed roots, and further regenerating the so derived plantlets into mature plants, which comprise inserted into their genome a T-DNA comprising said at least one plant expression cassette for an agronomically valuable trait, and—optionally—said at least one selectable marker gene.

The method described here is based on *Agrobacterium*-mediated gene delivery into growing cells in an axillary meristem of primary or higher leaf nodes. The method described here does not utilize a callus or proliferative phase. Instead, the *Agrobacterium*-mediated gene delivery is made into cells in the axillary meristem of primary or higher node of a soybean seedling. The axillary meristem may be inoculated with *Agrobacterium* when comprised in the complete seedling, or may be attached to an explant e.g., an excised petiole or leaf. Then the axillary meristem region is cultured in the presence of a hormone to induce direct shoot formation. Preferably, the meristem is cultivated in the presence of a selection marker (e.g., the herbicide phosphinotricin or a D-amino acid like e.g. D-alanine or D-serine). The result of this step is the induction of the formation of soybean shoots, which arise from a small cluster of cells including a trans-formed meristematic cell. The time period required for this method is greatly reduced compared to other *Agrobacterium*-mediated transformation protocols. Viable pheno-typically positive soybean shoots can be collected 4 to 6 weeks from the initiation of the procedure. The entire $T_0$ (primary transformant) plant life cycle is not greatly longer than the minimum required for a soybean plant to grow to maturity in a greenhouse.

The method of the invention provides one or more advantages over the methods described in the prior art:

1) For the axillary meristem methods, germinated seedlings of about 4 to 10 days, preferably about 7 days are needed. The efforts for establishing cultures are simplified using the method of the invention over embryogenic cultures.
2) The method is time efficient: The method of the invention based an axillary meristem methods produce de novo shoots within about 2 weeks after *Agrobacterium* infection and transgenic shoot primordia can be detected within about 3 weeks of *Agrobacterium* infection. The process for axillary meristem transformation after *Agrobacterium* infection is 3 to 4 weeks on shoot induction medium, a minimum of 2-4 weeks on shoot elongation medium, and 7 days on rooting medium.
3) Plant produced using *Agrobacterium*-mediated methods versus particle bombardment have less problems associated with the integration of multiple or fragmented copies of the introduced DNA into the genome (Hadi et al. (1996) Plant Cell Rep 15:500-505; Trick et al. (1997) Plant Tissue Cult Biotechnol 3:9-26).
4) The method of the invention is highly genotype and cultivar independent. Axillary meristem development is more likely across genotypes. The soybean tissue manipulations in this process are analogous to those in prior particle-mediated trans-formation methods, which have proven to be adaptable to all tested elite soybean varieties. This method is equally adapted for direct genetic transformation into elite soybean cultivars, thus potentially avoiding the need for extensive cross-breeding between varieties.
5) Method based on embryo axes transformation provide only between 3 to 7 shoots per explant. The method of the invention based on axillary meristem transformation is similar in time to plant production. An advantage is the proliferation of great numbers of shoot primordia (100 to 1,000's) that can give rise to multiple transgenic shoots (increases chance from culture to greenhouse) and increase chance that transgenic cell is selected for shoot elongation.
6) The method of the invention based on axillary meristem transformation are more amenable to selection due to the smaller tissue mass of the callus/shoot pad that are formed on the shoot induction medium as compared to the cotyledonary-node. The hypocotyl and/or epicotyl responsible for uptake of the selection compound seem to offer improved uptake properties in comparison with the more hard-tissued cotyledonary leaves.
7) Because of the small tissue size of the leaf explants and the propagated explants, the methods of the invention do not need as much medium, materials, and space for the culture process. For the cotyledonary node, only 5 explants can be cultured on one plate, however with the propagated and leaf explants, up to 20 can be cultured on a single plate.
8) For the variation based on propagated axillary meristem there is the additional advantage that plenty target material (i.e. multiple explants) can be obtained from material derived from 3 to 4 week-old propagated plantlets. One shoot is derived from growth of the main apical bud and—occasionally—one growth from each axillary bud at the cotyledonary node. Each shoot grows approximately 7 cm in length and contains 3 to 6 shorted internodes to obtain explants from. The small size of explants are amenable to *Agrobacterium* infection, selection and regeneration, and the propagated axillary meristems has surprisingly proven to be highly regenerable and produce plants without an intermediate callus phase. The small size of the explant and the vigorous growth of shoots should be favorable for the selection of trans-formed cells, which is problematic in current transformation methodologies.

The starting material for the transformation process is a soybean seed. The seed is first sterilized,—optionally—soaked for softening. The seeds are imbibed in water for approximately 3 minutes and then allowed to soften for up to 2 hours. The seeds are then put on germination media and germinated for a time period of about 4 to 10 days, preferably for about 5 to 8 days, and most preferably for about 7 days. The epicotyl is preferably about 0.5 cm at this time for propagated axillary meristem and leaf axillary meristem methods and generally 0.5 to 2 cm for seedling axillary meristem method. Preferably germination is carried out under high light condition ($>100$ μM m$^{-2}$s$^{-1}$) at 25° C.

The target tissue employed for *Agrobacterium* mediated transformation is axillary meristematic tissue comprised in the primary or higher leaf nodes. A primary leaf node is the node (i.e. the point on a stem where a leaf is attached or has been attached) directly following the cotyledonary node (i.e. the point on a stem where a cotyledonary leaf is attached or has been attached) when moving in the direction from the root to the leaves. Higher leaf nodes are all leaf nodes following the primary leaf node such as for example secondary, tertiary, quaternary etc. leaf nodes. Preferred is the axillary meristematic tissue of the primary leaf node.

The axillary meristematic tissue of the primary or higher node can be provided and employed in various forms in the subsequent *Agrobacterium* co-cultivation step:

a) Method A: Seedling axillary meristem: The entire seedling or a substantial part thereof (such as the seedling minus roots or the seedling without one or both cotyledons) can be employed, inoculated with *Agrobacterium* and placed on shoot induction medium (SIM). Preferably the substantially entire seedling is selected from the group of material consisting of
   i) an entire seedling, and
   ii) a seedling having the roots removed, and
   iii) a seedling having one or both cotyledons removed, and iv) a seedling having the roots and one or both cotyledons removed, and v) a seedling having the roots, both cotyledons and part of the epicotyl removed leaving the axillary meristem attached to part of the epicotyl.

b) Method B: Leaf axillary meristem: The primary or higher leafs are dissected in a way that the axillary meristematic tissue remains attached to the petioles of the leaves, dipped in (inoculated with) *Agrobacterium* solution, co-cultivated on co-cultivation medium, and placed on the shoot induction medium (SIM). The small size of the explant and the vigorous growth of shoots should be favorable for the selection of transformed cells, which is problematic in current transformation methodologies.

c) Method C: Propagated axillary meristem: From a germinated (preferably about) 7-day old seedling the hypocotyl and one and a half or part of both cotyledons are removed from each seedling. The seedlings are then placed on propagation media for 2 to 4 weeks. The seedlings produce several branched shoots to obtain explants from (FIG. 3). Axillary nodes from the first to the fourth leaf node can be excised. An average of three to four explants can be obtained from each seedling.

Beside the explicitly mentioned sources (Method A, B, C) point out above, other sources may be suitable for the axillary meristematic tissue. These sources may for example be more restricted explants derived from a soybean seedling such as only the epicotyl and the primary leaf node. Obviously such restricted (i.e. small) explants can not only be obtained from the primary node but also from higher nodes as well (e.g., secondary and higher nodes).

Preferably the method of the invention comprises one or more additional steps selected from the group of:

(a1) wounding the explant prior to, during or immediately after co-cultivation, and (b1) transferring said co-cultivated axillary meristematic tissue after step (b) to a medium comprising at least one antibiotic suitable to inhibit *Agrobacterium* growth, and—optionally—at least one plant growth factor, wherein said medium is preferably lacking a selection compound which in combination with the selectable marker gene of (b) would allow for identification and/or selection of plant cells, organs or plants comprising said selectable marker gene, and, (b2) further incubating said axillary, meristematic tissue after step (b) and—optionally (b1)—on a shoot induction medium (SIM) comprising at least one plant growth factor, wherein said shoot induction medium is preferably lacking a selection compound which in combination with the selectable marker gene of (b) would allow for identification and/or selection of plant cells, organs or plants comprising said selectable marker gene, and (c1) transferring said shoots after step (c) to a shoot elongation medium comprising (i) at least one plant growth factor in a concentration suitable to allow shoot elongation, and (ii) optionally one or more selection compounds which in combination with the selectable marker gene of (b) allow for identification and/or selection of a plant cell, tissue or plant comprising said selectable marker gene, and cultivating said transferred shoots on said shoot elongation medium until said shoots have elongated to a length of at least about 2 cm.

In a preferred embodiment of the invention, the axillary meristematic tissue is wounded (step (a1)). Wounding seems to have at least two enhancing effects on the method of the invention:

(i) wounding facilitates *Agrobacterium* infection and gene transfer efficiency, (ii) wounding enhances efficiency of de novo shoot induction presumably by disrupting the meristematic tissue connection significantly increasing the number of shoots developing from the explant tissue.

Wounding can be prior to inoculation (co-cultivation), during inoculation or after inoculation with *Agrobacterium*. For achieving both beneficial effects wounding is preferably done prior to or during co-cultivation, more preferably prior to co-cultivation. Many methods of wounding can be used, including, for example, cutting, abrading, piercing, poking, penetration with fine particles or pressurized fluids, plasma wounding, application of hyperbaric pressure, or sonication. Wounding can be performed using objects such as, but not limited to, scalpels, scissors, needles, abrasive objects, airbrush, particles, electric gene guns, or sound waves. Another alternative to enhance efficiency of the co-cultivation step is vacuum infiltration (Bechtold, et al. (1998) Meth. Mol. Biol. 82, 259-266; Trieu, et al. (2000) The Plant Journal 22(6), 531-541)).

The T-DNA is introduced into soybeans means of *Agrobacterium*-mediated DNA transfer. The term "*Agrobacterium*" as used herein means all species of the *Agrobacterium* family (including *Agrobacterium tumefaciens* and *Agrobacterium rhizogenes*). Preferably, transformation is realized utilizing strains of *Agrobacterium tumefaciens* or *Agrobacterium* rhizogenes. The principles of plant transformation by means of *Agrobacterium*-mediated DNA transfer are well known in the art (Horsch R B et al. (1985) Science 225: 1229 pp).

The *Agrobacterium* strain will include a DNA construct (e.g., a plasmid) comprising a T-DNA which comprises at least one selectable marker gene and—optionally—an additional plant expression cassette for an agronomically valuable trait. As a result of the *Agrobacterium* mediated transfer, said T-DNA will normally be present in all or substantially all of the cells of the plant tissue after transformation and regeneration.

*Agrobacterium tumefaciens* and *A. rhizogenes* are plant-pathogenic soil bacteria, which genetically transform plant cells. The Ti- and Ri-plasmids of *A. tumefaciens* and *A. rhizogenes*, respectively, carry genes responsible for genetic transformation of the plant (Kado (1991) Crit. Rev Plant Sci 10:1). Vectors are based on the *Agrobacterium* Ti- or Ri-plasmid and utilize a natural system of DNA transfer into the plant genome. As part of this highly developed parasitism *Agrobacterium* transfers a defined part of its genomic information (the T-DNA; flanked by about 25 bp repeats, named left and right border) into the chromosomal DNA of the plant cell (Zupan et al., (2000) Plant J 23(1):11-28). By combined action of the so-called vir genes (part of the original Ti-plasmids) said DNA-transfer is mediated. For utilization of this natural system, Ti-plasmids were developed which lack the original tumor inducing genes ("disarmed vectors"). In a further improvement, the so-called "binary vector systems", the T-DNA was physically separated from the other functional elements of the Ti-plasmid (e.g., the vir genes), by being incorporated into a shuttle vector, which allowed easier handling (EP-A 120 516; U.S. Pat. No. 4,940,838). These binary vectors comprise (beside the disarmed T-DNA with its border sequences), prokaryotic sequences for replication both in *Agrobacterium* and *E. coli*. It is an advantage of *Agrobacterium*-mediated transformation that in general only the DNA flanked by the borders is transferred into the genome and that preferentially only one copy is inserted. Descriptions of *Agrobacterium* vector systems and methods for *Agrobacterium*-mediated gene transfer are known in the art (Gruber et al. (1993) "Vectors for Plant Transformation," in METHODS IN PLANT MOLECULAR BIOLOGY AND BIOTECHNOLOGY; pp. 89-119; Miki et al. (1993) "Procedures for Introducing Foreign DNA into Plants" in METHODS IN PLANT MOLECULAR BIOLOGY AND BIOTECHNOLOGY; pp. 67-88; Moloney et al. (1989) Plant Cell Reports 8: 238).

Hence, for *Agrobacterium*-mediated transformation the genetic composition (e.g., comprising an expression cassette) is integrated into specific plasmids, either into a shuttle or intermediate vector, or into a binary vector. If a Ti or Ri plasmid is to be used for the transformation, at least the right border, but in most cases the right and left border, of the Ti or Ri plasmid T-DNA is linked to the expression cassette to be introduced in the form of a flanking region. Binary vectors are preferably used. Binary vectors are capable of replication both in *E. coli* and in *Agrobacterium*. They may comprise a selection marker gene and a linker or polylinker (for insertion of e.g. the expression cassette to be transferred) flanked by the right and left T-DNA border sequence. They can be transferred directly into *Agrobacterium* (Holsters et al. (1978) Mol Gen Genet. 163:181-187). The selection marker gene permits the selection of transformed *Agrobacteria* and is, for example, the nptIII gene, which confers resistance to kanamycin. The *Agrobacterium*, which acts as host organism in this case, should already contain a plasmid with the vir region. The latter is required for transferring the T-DNA to the plant cell. An *Agrobacterium* transformed in this way can be used for transforming plant cells. The use of T-DNA for transforming plant cells has been studied and described intensively (EP 120 516; Hoekema (1985) In: The Binary Plant Vector System, Offsetdrukkerij Kanters B. V., Alblasserdam, Chapter V; An et al. (1985) EMBO J. 4:277-287).

Common binary vectors are based on "broad host range"-plasmids like pRK252 (Bevan et al. (1984) Nucl Acid Res 12:8711-8720) or pTJS75 (Watson et al. (1985) EMBO J. 4(2):277-284) derived from the P-type plasmid RK2. Most of these vectors are derivatives of pBIN19 (Bevan et al. (1984) Nucl Acid Res 12:8711-8720). Various binary vectors are known, some of which are commercially available such as, for example, pBI101.2 or pBIN19 (Clontech Laboratories, Inc. USA). Additional vectors were improved with regard to size and handling (e.g. pPZP; Hajdukiewicz et al. (1994) Plant Mol Biol 25:989-994). Improved vector systems are described also in WO 02/00900.

Various *Agrobacterium* strains can be employed. Both *Agrobacterium tumefaciens* and *Agrobacterium rhizogenes* strains can be used. In a preferred embodiment "disarmed" strains (i.e., for which the tumor- or hair root phenotype inducing genes have been deleted) are utilized. An especially preferred *Agrobacterium rhizogenes* strain is a disarmed *Agrobacterium rhizogenes* K599 strain. Such strains are described in U.S. provisional application No. 60/606,789, filed Sep. 2, 2004, hereby incorporated entirely by reference. Preferred *Agrobacterium* strains to be employed in the method of the invention may include but shall not be limited to octopine strains, e.g., LBA4404 or agropine strains, e.g., EHA101 or EHA105. Suitable strains of *A. tumefaciens* for DNA transfer are for example EHA101-[pEHA101] (Hood et al. (1986) J Bacteriol 168:1291-1301), EHA105-[pEHA105] (Li (1992) Plant Mol Biol 20:1037-1048), LBA4404 [pAL4404] (Hoekema et al. (1983) Nature 303:179-181), C58C1[pMP90] (Koncz & Schell (1986) Mol Gen Genet. 204:383-396), and C58C1 [pGV2260] (Deblaere et al. (1985) Nucl Acids Res 13:4777-4788). Other suitable strains are *Agrobacterium tumefaciens* C58, a nopaline strain. Other suitable strains are *A. tumefaciens* C58C1 (Van Laerebeke et al. (1974) Nature 252, 169-170), A136 (Watson et al. (1975) J. Bacteriol 123, 255-264) or LBA4011 (Klapwijk et al. (1980) J. Bacteriol., 141, 128-136). The *Agrobacterium* strain may contain an octopine-type Ti-plasmid, preferably disarmed, such as pAL4404. Generally, when using octopine-type Ti-plasmids or helper plasmids, it is preferred that the virF gene be deleted or inactivated (Jarchow et al. (1991) Proc. Natl. Acad. Sci. USA 88:10426-10430). Additional suitable strains are C58C1[pGV2260] and C58C1[pMP90]. Strain C58C1[pGV2260] is an "Octopine-type" strain while C58C1[pMP90] is a "Nopaline-type" strain. The genetic background of both is *Agrobacterium* strain C58. C58 is also the genetic background for strain GV3101.

The method of the invention can also be used in combination with particular *Agrobacterium* strains to further increase the transformation efficiency, such as *Agrobacterium* strains wherein the vir gene expression and/or induction thereof is altered due to the presence of mutant or chimeric virA or virG genes (e.g. Hansen et al (1994) Proc. Natl. Acad. Sci. USA 91:7603-7607; Chen and Winans (1991) J. Bacteriol. 173: 1139-1144; Scheeren-Groot et al. (1994) J. Bacteriol 176: 6418-6426). Possible are further combinations of *Agrobacterium tumefaciens* strain (e.g., LBA4404; Hiei et al. (1994) Plant J 6: 271-282) with super-virulent plasmids (e.g., pTOK246-based vectors; Ishida Y et al. (1996) Nature Biotech 745-750), so called super-virulent strains. An example of a super-virulent strain is the succinamopine strain EHA105.

A binary vector or any other vector can be modified by common DNA recombination techniques, multiplied in *E. coli*, and introduced into *Agrobacterium* by e.g., electroporation or other transformation techniques (Mozo and Hooykaas (1991) Plant Mol Biol 16:917-918).

*Agrobacteria* are grown and used in a manner as known in the art. The vector comprising *Agrobacterium* strain may, for example, be grown for 3 days on YEP medium (see Example 2) supplemented with the appropriate antibiotic (e.g., 50 mg/l spectinomycin). Bacteria are collected with a loop from the solid medium and resuspended. In a preferred embodiment of the invention, *Agrobacterium* cultures are started by use of aliquots frozen at −80° C. For *Agrobacterium* treatment of the various soybean axillary meristem explant tissues, the bacteria are preferably resuspended in the co-cultivation medium (CCM).

The concentration of *Agrobacterium* used for infection and co-cultivation may need to be varied. Thus, generally a range of *Agrobacterium* concentrations from $OD_{600}$ 0.1 to 3.0 and a range of co-cultivation periods from a few hours to 7 days can be used. Preferably for the various axillary meristematic tissue explants the following concentrations of *Agrobacterium* suspensions are employed:
a) Method A (seedling axillary meristem): From about $OD_{600}$=0.5 to about 3, preferably from about $OD_{600}$=1 to 2.
b) Method B (leaf axillary meristem): From about $OD_{600}$=0.1 to about 1, preferably from about $OD_{600}$=0.125 to 0.5.
c) Method C (propagated axillary meristem): From about $OD_{600}$=0.2 to about 1.5, preferably from about $OD_{600}$=0.5 to 0.8.

The co-cultivation of *Agrobacterium* with the various soybean axillary meristem explant tissues is in general carried out for about 1 to about 6 days, preferably about 3 to about 5 days for *Agrobacterium tumefaciens* strains, and about 2 to about 3 days for *Agrobacterium rhizogenes* strains.

The explants are then inoculated with the *Agrobacterium* culture for a few minutes to a few hours, typically about 10 minutes to 3 hours, preferably about 0.5 hours to 1 hour. The excess media is drained and the *Agrobacterium* are permitted to co-cultivate with the meristem tissue for several days, typically three to five days in the dark. During this step, the

*Agrobacterium* transfers the foreign genetic construct into some cells in the soybean axillary meristem. Normally no selection compound is present during this step.

It is possible, although not necessary, to employ one or more phenolic compounds in the medium prior to or during the *Agrobacterium* co-cultivation. "Plant phenolic compounds" or "plant phenolics" suitable within the scope of the invention are those isolated substituted phenolic molecules which are capable to induce a positive chemotactic response, particularly those who are capable to induce increased vir gene expression in a Ti-plasmid containing *Agrobacterium* sp., particularly a Ti-plasmid containing *Agrobacterium tumefaciens*. Preferred is acetosyringone. Moreover, certain compounds, such as osmoprotectants (e.g. L-proline preferably at a concentration of about 700 mg/L or betaine), phytohormones (inter alia NAA), opines, or sugars, are expected to act synergistically when added in combination with plant phenolic compounds. The plant phenolic compound, particularly acetosyringone, can be added to the medium prior to contacting the various soybean axillary meristem explant tissues with *Agrobacteria* (for e.g., several hours to one day). Possible concentrations of plant phenolic compounds in the medium range from about 25 μM to 700 μM. Particularly suited induction conditions for *Agrobacterium tumefaciens* have been described (Vernade et al. (1988) J. Bacteriol. 170: 5822-5829). Efficiency of transformation with *Agrobacterium* can be enhanced by numerous other methods known in the art like for example vacuum infiltration (WO 00/58484), heat shock and/or centrifugation, addition of silver nitrate, sonication etc.

Supplementation of the co-cultivation medium with antioxidants (e.g., dithiothreitol), or thiol compounds (e.g., L-cysteine, Olhoft P M & D A Somers (2001) Plants Cell Reports 20:706-711; US2001034888) which can decrease tissue necrosis due to plant defense responses (like phenolic oxidation) may further improve the efficiency of *Agrobacterium*-mediated transformation.

After the co-cultivation with the bacteria described above (e.g., by a washing step). The medium employed after the co-cultivation step (e.g., the medium employed in step (b1) (c), and/or (c1)) preferably contains a bacteriocide (antibiotic). This step is intended to terminate or at least retard the growth of the non-transformed cells and kill the remaining *Agrobacterium* cells. Accordingly, the method of the invention comprises preferably the step of:

(b1) transferring said co-cultivated axillary meristematic tissue after step (b) to a medium comprising at least one antibiotic suitable to inhibit *Agrobacterium* growth, and—optionally—at least one plant growth factor, wherein said medium is preferably lacking a selection compound which in combination with the selectable marker gene of (b) would allow for identification and/or selection of plant cells, organs or plants comprising said selectable marker gene, and, Preferred antibiotics to be employed are e.g., carbenicillin (500 mg/L or—preferably—100 mg/L) or Timentin™ (GlaxoSmithKline; used preferably at a concentration of about 250-500 mg/L; Timentin™ is a mixture of ticarcillin disodium and clavulanate potassium; 0.8 g Timentin™ contains 50 mg clavulanic acid with 750 mg ticarcillin. Chemically, ticarcillin disodium is N-(2-Carboxy-3,3-dimethyl-7-oxo-4-thia-1-azabicyclo[3.2.0]hept-6-yl)-3-thiophenemalonamic acid disodium salt. Chemically, clavulanate potassium is potassium (Z)-(2R,5R)-3-(2-hydroxyethylidene)-7-oxo-4-oxa-1-azabicyclo[3.2.0]heptane-2-carboxylate).

After the co-cultivation step the co-cultivated explants are incubated on a shoot induction medium comprising at least one plant growth factor. Said incubation on shoot induction medium can be started immediately after the co-cultivation step (i.e. in parallel with step (b1) for inhibiting growth of the *Agrobacteria*) or after other intermediate steps such as (b1) (inhibiting growth of the *Agrobacteria*) and/or (b2) (regeneration without selection compound; see below).

These media may further contain at least one compound, which in combination with the selectable marker gene of (b) allows for identification and/or selection of plant cells (e.g., a selection compound) may be applied. However, it is preferred that explants are incubated for a certain time from about 4 to about 7 days after the co-cultivation step (b) on medium lacking a selection compound which in combination with the selectable marker gene of (b) would allow for identification and/or selection of plant cells, organs or plants comprising said selectable marker gene. Establishment of a reliable resistance level against said selection compound needs some time to prevent unintended damage by the selection compound even to the transformed cells and tissue. Accordingly, the method of the invention may comprise a step between co-cultivation and selection which is carried out without a selection compound. This step may be step (b1) and/or a specific additional step:

(b2) further incubating said axillary, meristematic tissue after step (b) and—optionally (b1)—on a shoot induction medium (SIM) comprising at least one plant growth factor, wherein said shoot induction medium is preferably lacking a selection compound which in combination with the selectable marker gene of (b) would allow for identification and/or selection of plant cells, organs or plants comprising said selectable marker gene.

The media as employed during the method of the invention for shoot induction (and/or shoot elongation) may be optionally further supplemented with one or more plant growth regulator, like e.g., cytokinin compounds (e.g., 6-benzylaminopurine) and/or auxin compounds (e.g., 2,4-D). The term "plant growth regulator" (PGR) as used herein means naturally occurring or synthetic (not naturally occurring) compounds that can regulate plant growth and development. PGRs may act singly or in consort with one another or with other compounds (e.g., sugars, amino acids). The term "auxin" or "auxin compounds" comprises compounds which stimulate cellular elongation and division, differentiation of vascular tissue, fruit development, formation of adventitious roots, production of ethylene, and—in high concentrations—induce dedifferentiation (callus formation). The most common naturally occurring auxin is indoleacetic acid (IAA), which is transported polarly in roots and stems. Synthetic auxins are used extensively in modern agriculture. Synthetic auxin compounds comprise indole-3-butyric acid (IBA), naphthylacetic acid (NAA), and 2,4-dichlorphenoxyacetic acid (2,4-D). Compounds that induce shoot formation include, but not limited to, IAA, NAA, IBA, cytokinins, auxins, kinetins, glyphosate, and thiadiazuron.

The term "cytokinin" or "cytokinin compound" comprises compounds which stimulate cellular division, expansion of cotyledons, and growth of lateral buds. They delay senescence of detached leaves and, in combination with auxins (e.g. IAA), may influence formation of roots and shoots. Cytokinin compounds comprise, for example, 6-isopentenyladenine (IPA) and 6-benzyladenine/6-benzylaminopurine (BAP).

In another preferred embodiment, the media of at least one of step (b), (b1), (b2), and/or (c), comprises a cytokinin (like e.g., 6-benzylaminopurine (BAP). Preferably the concentration is between about 1 µM and about 10 µM 6-benzylaminopurine (BAP). For the shoot induction medium a BAP concentration of about 1 to about 3 µM is preferred. Preferably, the BAP concentration is not higher than 5 µM.

It is furthermore especially preferred, that the media of at least one of step (b), (b1), (b2), (c) and/or (c1), preferably at least (b) and (c1), comprises between about 0.1 µM and about 2 µM Gibberellic acid (GA3).

In another preferred embodiment, the media of at least one of step (b), (b1), (b2), and (c) comprises least one thiol compound, preferably selected from the group consisting of sodium thiolsulfate, dithiotrietol (DTT) and cysteine. Preferably the concentration is between about 1 mM and 10 mM of L-Cysteine, 0.1 mM to 5 mM DTT, and/or 0.1 mM to 5 mM sodium thiolsulfate.

The explants are incubated on said shoot induction medium until shoots have been developed. The shoot primordia that form are usually no longer than 0.3 cm in size. Formation of shoot primordia begins around 1 week on shoot induction medium and, on average, such shoot initiation continues for about 3 to 4 weeks to reach maximum size. Accordingly, co-cultivated explants are incubated on said shoot induction medium for about 2 to 6 weeks, preferably about 3 to 4 weeks.

*Agrobacterium*-mediated techniques typically may result in gene delivery into a limited number of cells in the targeted tissue. Therefore, in a preferred embodiment of the invention, a selection compound is applied post-transformation to kill all of the cells in the targeted tissues that are not transformed or to identify transformed cells through a selective advantage. The length of culture depends, in part, on the toxicity of the selection compound to untransformed cells. The selectable marker gene and the corresponding selection compound used for said selection or screening can be any of a variety of well-known selection compounds, such as antibiotics, herbicides, or D-amino acids (see below for details). The length of this culture step is variable (depending on the selection compound and its concentration, the selectable marker gene), extending from one day to about 180 days.

Insertion of a selectable and/or screenable marker gene is comprised within the scope of the method of the invention. This may be advantageous e.g., for later use as a herbicide-resistance trait. Various selectable marker genes and corresponding selection compounds are known in the art. Furthermore, reporter genes can be employed to allow visual screening, which may or may not (depending on the type of reporter gene) require supplementation with a substrate as a selection compound.

Various time schemes can be employed for the various selection marker genes. In case of resistance genes (e.g., against herbicides or D-amino acids) selection is usually applied throughout the shoot initiation for about 4 weeks and beyond at least 4 weeks into shoot elongation. Such a selection scheme can be applied for all selection regimes, including kanamycin. It is furthermore possible (although not explicitly preferred) to remain the selection also throughout the entire regeneration scheme including rooting.

For example, with the kanamycin resistance gene (neomycin phosphotransferase, NPTII) as the selective marker, kanamycin at a concentration of from about 3 to 200 mg/l may be included in the medium. Typical concentrations for selection are 5 to 50 mg/l. The tissue is grown upon this medium for a period of about 1 to about 4 weeks, preferably about 7 days until shoots have developed. Shoot formation begins in about 1 to about 2 weeks depending on treatment and co-cultivation conditions.

For example, with the phosphinotricin resistance gene (bar) as the selective marker, phosphinotricin at a concentration of from about 1 to 50 mg/l may be included in the medium. Typical concentrations for selection are from about 1 to about 15 mg/l. The tissue is grown upon this medium for a period of about 1 to about 4 weeks, preferably about 7 days until shoots have developed. Shoot formation begins in about 1 to 2 weeks depending on treatment and co-cultivation conditions.

For example, with the dao1 gene as the selective marker, D-serine or D-alanine at a concentration of from about 3 to 100 mM may be included in the medium. Preferably, for D-serine concentrations from about 10 to about 70 mM (or from about 1 to about 7.5 g/L) are used. Typical concentrations for selection are from about 10 mM to about 50 mM (or from about 1 to 5.3 g/l). The tissue is grown upon this medium for a period of about 1 to about 4 weeks, preferably about 7 days until shoots have developed. Shoot formation begins in about 1 to about 2 weeks depending on treatment and cocultivation conditions.

In a preferred embodiment all shoots formed before transformation will be removed up to about 2 weeks after co-cultivation to stimulate new growth from the meristems. This helps to reduce chimerism in the primary transformant and increase amplification of transgenic meristematic cells. During this time the explant may or may not be cut into smaller pieces (i.e. detaching the node from the explant by cutting the epicotyl).

After 2 to 4 weeks (or until a mass of shoots has formed) on SIM medium (preferably with selection), the explants will be transferred to shoot elongation (SEM) medium that will stimulate shoot elongation (of the shoot primordia). This medium may or may not contain a selection compound, but preferably contains a selection compound. The frequency and length of the shoots elongating are influenced by the hormone levels, in particular BAP, in the SIM (Example 9).

In another preferred embodiment of the invention, the media of at least one of step (c1) and/or (d) comprises between about 0.01 mg/l (0.057 M) and about 1 mg/l (5.7 µM) indole acetic acid (IAA), and/or between about 0.1 µM and about 4 µM Gibberellic acid (GA3), and/or between about 0.5 µM and about 6 µM trans-zeatin riboside acid.

Preferably, after every 2 to 3 weeks the explants are transferred to fresh SEM medium (preferably containing the selection compound) after carefully removing dead tissue. The explants should hold together and not fragment into pieces and retain somewhat healthy. Preferably, the explants will continue to be transferred until the explant dies or shoots elongate.

The elongated shoots are ready for harvest about 4 to 8 weeks after transfer to the shoot elongation medium. The shoots are evaluated for phenotypic regularity and health, and only shoots with elongated stems (approximately 1 inch or 2 cm) and full trifoliate leaf formation are harvested.

The collected shoots are placed on a rooting medium to induce root formation. Root formation takes approximately 1 to 4 weeks, following which the plants can be transferred to soil and grown to full maturity. The rooting medium may (also not explicitly preferred) also contain the selection compound. Preferably, elongated shoots (length larger than 3 cm) are removed and placed into rooting medium (RM) for about 1 week (Method B), or about 2 to 4 weeks depending on the cultivar (Method C) at which time roots begin to form. In the case of explants with roots, they are transferred directly into soil. Rooted shoots are transferred to soil and hardened in a growth chamber for 2 to 3 weeks before transferring to the greenhouse. Regenerated plants obtained using this method are fertile and have produced on average 500 seeds per plant.

The $T_0$ plants created by this technique are transgenic plants and are regularly recovered with quite reasonable yields. For Method C, the average regeneration time of a soybean plantlet using the propagated axillary meristem protocol is 14 weeks from explant inoculation. Therefore, this method has a quick regeneration time that leads to fertile, healthy soybean plants.

Transformed plant material (e.g., cells, tissues or plantlets), which express marker genes, are capable of developing in the presence of concentrations of a corresponding selection compound (e.g., antibiotic or herbicide) which suppresses growth of an untransformed wild type tissue. The resulting plants can be bred and hybridized in the customary fashion. Two or more generations should be grown in order to ensure that the genomic integration is stable and hereditary.

Other important aspects of the invention include the progeny of the transgenic plants prepared by the disclosed methods, as well as the cells derived from such progeny, and the seeds obtained from such progeny.

CONSTITUTION OF THE T-DNA OF THE INVENTION

As with other *Agrobacterium*-mediated methods, the foreign genetic construction, or transgene, to be inserted into the soybean genome is created in vitro by normal techniques of recombinant DNA manipulations. The genetic construct is then transformed into the *Agrobacterium* strain for delivery into the soybean cells. The *Agrobacterium* is non-oncogenic, and several such strains are now widely available.

Preferably, the T-DNA inserted into the genome of the target soybean plant comprises at least one expression cassette, which may—for example—facilitate expression of selection marker gene, trait genes, antisense RNA or double-stranded RNA. Preferably said expression cassettes comprise a promoter sequence functional in plant cells operatively linked to a nucleic acid sequence which—upon expression—confers an advantageous phenotype to the so transformed plant. The person skilled in the art is aware of numerous sequences which may be utilized in this context, e.g. to increase quality of food and feed, to produce chemicals, fine chemicals or pharmaceuticals (e.g., vitamins, oils, carbohydrates; Dunwell (2000) J Exp Bot 51 Spec No:487-96), conferring resistance to herbicides, or conferring male sterility. Furthermore, growth, yield, and resistance against abiotic and biotic stress factors (like e.g., fungi, viruses or insects) may be enhanced. Advantageous properties may be conferred either by overexpressing proteins or by decreasing expression of endogenous proteins by e.g., expressing a corresponding antisense (Sheehy et al. (1988) Proc Natl Acad Sci USA 85: 8805-8809; U.S. Pat. No. 4,801,340; Mol J N et al. (1990) FEBS Lett 268(2):427-430) or double-stranded RNA (Matzke M A et al. (2000) Plant Mol Biol 43:401-415; Fire A. et al. (1998) Nature 391:806-811; Waterhouse P M et al. (1998) Proc Natl Acad Sci USA 95:13959-13964; WO 99/32619; WO 99/53050; WO 00/68374; WO 00/44914; WO 00/44895; WO 00/49035; WO 00/63364).

For expression in plants, plant-specific promoters are preferred. The term "plant-specific promoter" is understood as meaning, in principle, any promoter which is capable of governing the expression of genes, in particular foreign genes, in plants or plant parts, plant cells, plant tissues or plant cultures. In this context, expression can be, for example, constitutive, inducible or development-dependent. The following are preferred:

a) Constitutive Promoters

"Constitutive" promoters refers to those promoters which ensure expression in a large number of, preferably all, tissues over a substantial period of plant development, preferably at all times during plant development. A plant promoter or promoter originating from a plant virus is especially preferably used. The promoter of the CaMV (cauliflower mosaic virus) 35S transcript (Franck et al. (1980) Cell 21:285-294; Shewmaker et al. (1985) Virology 140:281-288; Gardner et al. (1986) Plant Mol Biol 6:221-228; Odell et al. (1985) Nature 313:810-812) or the 19S CaMV promoter (U.S. Pat. No. 5,352,605; WO 84/02913; Benfey et al. (1989) EMBO J. 8:2195-2202) are especially preferred. Another suitable constitutive promoter is the rice actin promoter (McElroy et al. (1990) Plant Cell 2: 163-171), Rubisco small subunit (SSU) promoter (U.S. Pat. No. 4,962,028), the legumin B promoter (GenBank Acc. No. X03677), the promoter of the nopaline synthase from *Agrobacterium*, the TR dual promoter, the OCS (octopine synthase) promoter from *Agrobacterium*, the ubiquitin promoter (Holtorf et al., (1995) Plant Mol Biol 29:637-649), the ubiquitin 1 promoter (Christensen et al. (1989) Plant Mol. Biol. 12: 619-632; Christensen et al. (1992) Plant Mol Biol 18:675-689; Bruce et al. (1989) Proc Natl Acad Sci USA 86:9692-9696), the Smas promoter, the cinnamyl alcohol dehydrogenase promoter (U.S. Pat. No. 5,683, 439), the promoters of the vacuolar ATPase subunits, the pEMU promoter (Last D I et al. (1991) Theor. Appl. Genet. 81, 581-588); the MAS promoter (Velten et al. (1984) EMBO J. 3(12): 2723-2730.) and maize H3 histone promoter (Lepetit et al. (1992) Mol Gen Genet. 231: 276-285; Atanassova et al. (1992) Plant J 2(3): 291-300), the promoter of the *Arabidopsis thaliana* nitrilase-1 gene (GenBank Acc. No.: U38846, nucleotides 3862 to 5325 or else 5342) or the promoter of a proline-rich protein from wheat (WO 91/13991), and further promoters of genes whose constitutive expression in plants.

b) Tissue-Specific or Tissue-Preferred Promoters

Furthermore preferred are promoters with specificities for seeds, such as, for example, the phaseolin promoter (U.S. Pat. No. 5,504,200; Bustos et al. (1989) Plant Cell 1(9):839-53; Murai et al., Science 23: 476-482 (1983); Sengupta-Gopalan et al., (1985) Proc. Natl. Acad. Sci. USA 82: 3320-3324), the promoter of the 2S albumin gene (Joseffson et al. (1987) J Biol Chem 262:12196-12201), the legumine promoter (Shirsat et al. (1989) Mol Gen Genet. 215:326-331), the USP (unknown seed protein) promoter (Baumlein et al. (1991a) Mol Gen Genet. 225(3):459-467), the napin gene promoter (U.S. Pat. No. 5,608,152; Stalberg et al. (1996) Planta 199: 515-519), the promoter of the sucrose binding proteins (WO 00/26388) or the legumin B4 promoter (LeB4; Baumlein et al. (1991b) Mol Gen Genet. 225:121-128; Becker et al. (1992) Plant Mol. Biol. 20: 49), the *Arabidopsis* oleosin promoter (WO 98/45461), and the *Brassica* Bce4 promoter (WO 91/13980). Further preferred are a leaf-specific and light-induced promoter such as that from cab or Rubisco (Simpson et al. (1985) EMBO J. 4:2723-2729; Timko et al. (1985) Nature 318: 579-582); an anther-specific promoter such as that from LAT52 (Twell et al. (1989b) Mol Gen Genet. 217: 240-245); a pollen-specific promoter such as that from Zml3 (Guerrero et al. (1993) Mol Gen Genet. 224:161-168); and a microspore-preferred promoter such as that from apg (Twell et al. (1983) Sex. Plant Reprod. 6: 217-224).

c) Chemically Inducible Promoters

The expression cassettes may also contain a chemically inducible promoter (review article: Gatz et al. (1997) Annu Rev Plant Physiol Plant Mol Biol 48:89-108), by means of which the expression of the exogenous gene in the plant can be controlled at a particular point in time. Such promoters such as, for example, the PRP1 promoter (Ward et al. (1993) Plant Mol Biol 22:361-366), a salicylic acid-inducible promoter (WO 95/19443), a benzenesulfonamide-inducible promoter (EP 0 388 186), a tetracyclin-inducible promoter (Gatz et al. (1991) Mol Gen Genetics 227:229-237; Gatz et al. (1992) Plant J 2:397-404), an abscisic acid-inducible promoter EP 0 335 528) or an ethanol-cyclohexanone-inducible promoter (WO 93/21334) can likewise be used. Also suitable is the promoter of the glutathione-S transferase isoform II gene (GST-II-27), which can be activated by exogenously applied safeners such as, for example, N,N-diallyl-2,2-dichloroacetamide (WO 93/01294) and which is operable in a large number of tissues of both monocots and dicots. Further exemplary inducible promoters that can be utilized in the instant invention include that from the ACE1 system which responds to copper (Mett et al. (1993) Proc Natl Acad Sci USA 90: 4567-4571); or the In2 promoter from maize which responds to benzenesulfonamide herbicide safeners (Hershey et al. (1991) Mol Gen Genetics 227:229-237; Gatz et al. (1994) Mol Gen Genetics 243:32-38). A promoter that responds to an inducing agent to which plants do not normally respond can be utilized. An exemplary inducible promoter is the inducible promoter from a steroid hormone gene, the transcriptional activity of which is induced by a glucocorticosteroid hormone (Schena et al. (1991) Proc Natl Acad Sci USA 88:10421).

Particularly preferred are constitutive promoters. Furthermore, promoters may be linked operably to the nucleic acid sequence to be expressed, which promoters make possible the expression in further plant tissues or in other organisms, such as, for example, *E. coli* bacteria. Suitable plant promoters are, in principle, all of the above-described promoters.

The genetic component and/or the expression cassette may comprise further genetic control sequences in addition to a promoter. The term "genetic control sequences" is to be understood in the broad sense and refers to all those sequences that have an effect on the materialization or the function of the expression cassette according to the invention. For example, genetic control sequences modify the transcription and translation in prokaryotic or eukaryotic organisms. Preferably, the expression cassettes according to the invention encompass a promoter functional in plants 5'-upstream of the nucleic acid sequence in question to be expressed recombinantly, and 3'-downstream a terminator sequence as additional genetic control sequence and, if appropriate, further customary regulatory elements, in each case linked operably to the nucleic acid sequence to be expressed recombinantly.

Genetic control sequences furthermore also encompass the 5'-untranslated regions, introns or noncoding 3'-region of genes, such as, for example, the actin-1 intron, or the Adh1-S introns 1, 2 and 6 (general reference: The Maize Handbook, Chapter 116, Freeling and Walbot, Eds., Springer, New York (1994)). It has been demonstrated that they may play a significant role in the regulation of gene expression. Thus, it has been demonstrated that 5'-untranslated sequences can enhance the transient expression of heterologous genes. Examples of translation enhancers which may be mentioned are the tobacco mosaic virus 5'-leader sequence (Gallie et al. (1987) Nucl Acids Res 15:8693-8711) and the like. Furthermore, they may promote tissue specificity (Rouster J et al. (1998) Plant J 15:435-440).

The expression cassette may advantageously comprise one or more enhancer sequences, linked operably to the promoter, which make possible an increased recombinant expression of the nucleic acid sequence. Additional advantageous sequences, such as further regulatory elements or terminators, may also be inserted at the 3'-end of the nucleic acid sequences to be expressed recombinantly. Polyadenylation signals which are suitable as control sequences are plant polyadenylation signals, preferably those which essentially correspond to T-DNA polyadenylation signals from *Agrobacterium tumefaciens*, in particular the OCS (octopine synthase) terminator and the NOS (nopaline synthase) terminator.

Control sequences are furthermore to be understood as those permitting removal of the inserted sequences from the genome. Methods based on the cre/lox (Sauer (1998) Methods 14(4):381-92; Odell et al. (1990) Mol Gen Genet. 223: 369-378; Dale and Ow (1991) Proc Natl Acad Sci USA 88:10558-10562), FLP/FRT (Lysnik (1993) Nucl Acid Res 21:969-975), or Ac/Ds system (Wader et al. (1987) in TOMATO TECHNOLOGY 189-198 (Alan R. Liss, Inc.); U.S. Pat. No. 5,225,341; Baker et al. (1987) EMBO J. 6: 1547-1554; Lawson et al. (1994) Mol Gen Genet. 245:608-615) permit an—if appropriate tissue-specific and/or inducible—removal of a specific DNA sequence from the genome of the host organism. Control sequences may in this con-text mean the specific flanking sequences (e.g., lox sequences), which later allow removal (e.g., by means of cre recombinase).

The genetic component and/or expression cassette of the invention may comprise further functional elements. The term functional element is to be understood in the broad sense and refers to all those elements that have an effect on the generation, amplification or function of the genetic component, expression cassettes or recombinant organisms according to the invention. Functional elements may include for example (but shall not be limited to):

1. Selectable Marker Genes

Selectable marker genes are useful to select and separate successfully transformed or homologous recombined cells. Preferably, within the method of the invention one marker may be employed for selection in a prokaryotic host, while another marker may be employed for selection in a eukaryotic host, particularly the plant species host. The markers may be protection against a biocide, such as antibiotics, toxins, heavy metals, or the like, or may function by complementation, imparting prototrophy to an auxotrophic host. Preferred selectable marker genes for plants may include but are not be limited to the following:

1.1 Negative Selection Markers

Negative selection markers confer a resistance to a biocidal compound such as a metabolic inhibitor (e.g., 2-deoxyglucose-6-phosphate, WO 98/45456), antibiotics (e.g., kanamycin, G 418, bleomycin or hygromycin) or herbicides (e.g., phosphinothricin or glyphosate). Especially preferred negative selection markers are those which confer resistance to herbicides. Examples which may be mentioned are:

Phosphinothricin acetyltransferases (PAT; also named Bialophos™ resistance; bar; De Block et al. (1987) Plant Physiol 91:694-701; EP 0 333 033; U.S. Pat. No. 4,975, 374)

5-enolpyruvylshikimate-3-phosphate synthase (EPSPS; U.S. Pat. No. 5,633,435) or glyphosate oxidoreductase gene (U.S. Pat. No. 5,463,175) conferring resistance to Glyphosate™ (N-(phosphonomethyl)glycine) (Shah et al. (1986) Science 233: 478)

Glyphosate™ degrading enzymes (Glyphosate™ oxidoreductase; gox),

Dalapon™ inactivating dehalogenases (deh)

Sulfonylurea- and imidazolinone-inactivating acetolactate synthases (for example mutated ALS variants with, for example, the S4 and/or Hra mutation Bromoxynil™ degrading nitrilases (bxn)

Kanamycin- or. G418-resistance genes (NPTII; NPTI) coding e.g., for neomycin phosphotransferases (Fraley et al. (1983) Proc Natl Acad Sci USA 80:4803), which expresses an enzyme conferring resistance to the antibiotic kanamycin and the related antibiotics neomycin, paromomycin, gentamicin, and G418, 2-Deoxyglucose-6-phosphate phosphatase (DOGR1—Gene product; WO 98/45456; EP 0 807 836) conferring resistance against 2-desoxyglucose (Randez-Gil et al. (1995) Yeast 11:1233-1240)

Hygromycin phosphotransferase (HPT), which mediates resistance to hygromycin (Vanden Elzen et al./(1985) Plant Mol. Biol. 5:299).

Dihydrofolate reductase (Eichholtz et al. (1987) Somatic Cell and Molecular Genetics 13: 67-76)

Additional negative selectable marker genes of bacterial origin that confer resistance to antibiotics include the aadA gene, which confers resistance to the antibiotic spectinomycin, gentamycin acetyl transferase, streptomycin phosphotransferase (SPT), aminoglycoside-3-adenyl transferase and the bleomycin resistance determinant (Hayford et al. (1988) Plant Physiol. 86:1216; Jones et al. (1987) Mol. Gen. Genet., 210:86; Svab et al. (1990) Plant Mol. Biol. 14:197; Hille et al. (1986) Plant Mol. Biol. 7:171).

Especially preferred are negative selection markers that confer resistance against the toxic effects imposed by D-amino acids like e.g., D-alanine and D-serine (WO 03/060133). Especially preferred as negative selection marker in this contest are the daoI gene (EC: 1.4. 3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3. 1.18; GenBank Acc.-No.: J01603).

1.2 Positive Selection Marker

Positive selection markers are conferring a growth advantage to a transformed plant in comparison with a non-transformed one. Genes like isopentenyltransferase from *Agrobacterium tumefaciens* (strain:PO22; Genbank Acc.-No.: AB025109) may—as a key enzyme of the cytokinin biosynthesis—facilitate regeneration of transformed plants (e.g., by selection on cytokinin-free medium). Corresponding selection methods are described (Ebinuma et al. (2000) Proc Natl Acad Sci USA 94:2117-2121; Ebinuma et al. (2000) Selection of Marker-free transgenic plants using the oncogenes (ipt, rol A, B, C) of *Agrobacterium* as selectable markers, In Molecular Biology of Woody Plants. Kluwer Academic Publishers). Additional positive selection markers, which confer a growth advantage to a transformed plant in comparison with a non-transformed one, are described e.g., in EP-A 0 601 092. Growth stimulation selection markers may include (but shall not be limited to) β-Glucuronidase (in combination with e.g., a cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

1.3 Counter Selection Marker

Counter selection markers are especially suitable to select organisms with defined deleted sequences comprising said marker (Koprek et al. (1999) Plant J 19: 719-726). Examples for negative selection marker comprise thymidine kinases (TK), cytosine deaminases (Gleave et al. (1999) Plant Mol. Biol. 40(2):223-35; Perera et al. (1993) Plant Mol. Biol. 23: 793-799; Stougaard (1993) Plant J 3:755-761), cytochrome P450 proteins (Koprek et al. (1999) Plant J 19: 719-726), haloalkan dehalogenases (Naested (1999) Plant J 18:571-576), iaaH gene products (Sundaresan et al. 1995), cytosine deaminase codA (Schlaman and Hooykaas (1997) Plant J 11:1377-1385), or tms2 gene products (Fedoroff and Smith (1993) Plant J 3:273-289).

2. Reporter Genes

Furthermore, the term selectable marker gene may further comprise other genes which allow for identification and/or selection of transformed cells or organisms, such as reporter genes which allow for visual screening and identification of such transformed cells (without application of phytotoxic compounds). Some of said reporter genes may require additional of a substrate for identification (such as the GUS gene) while others are functional without such substrates (such as GFP).

Reporter genes encode readily quantifiable proteins and, via their color or enzyme activity, make possible an assessment of the transformation efficacy, the site of expression or the time of expression. Very especially preferred in this context are genes encoding reporter proteins (Schenborn, Groskreutz (1999) Mol Biotechnol 13(1):29-44) such as the green fluorescent protein (GFP) (Sheen et al. (1995) Plant J 8(5): 777-784; Haseloff et al., (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228; Chui et al. (1996) Curr Biol 6:325-330; Leffel et al. (1997) Biotechniques 23(5):912-8), Reef-coral proteins (Wenck et al. (2003) Plant Cell Reporter 22: 241-251), chloramphenicol transferase, a luciferase (Ow et al. (1986) Science 234:856-859; Millar et al. (1992) Plant Mol Biol Rep 10:324-414), the aequorin gene (Prasher et al. (1985) Biochem Biophys Res Commun 126(3):1259-1268)), β-galactosidase, R locus gene (encoding a protein which regulates the production of anthocyanin pigments (red coloring) in plant tissue and thus makes possible the direct analysis of the promoter activity without addition of further auxiliary substances or chromogenic substrates (Dellaporta et al. (1988) In: Chromosome Structure and Function: Impact of New Concepts, 18th Stadler Genetics Symposium, 11:263-282; Ludwig et al. (1990) Science 247:449), with β-glucuronidase (GUS) being very especially preferred (Jefferson (1987b) Plant Mol. Bio. Rep., 5:387-405; Jefferson et al. (1987a) EMBO J. 6:3901-3907). β-glucuronidase (GUS) expression is detected by a blue color on incubation of the tissue with 5-bromo-4-chloro-3-indolyl-β-D-glucuronic acid, bacterial luciferase (LUX) expression is detected by light emission; firefly luciferase (LUC) expression is detected by light emission after incubation with luciferin; and galactosidase expression is detected by a bright blue color after the tissue was stained with 5-bromo-4-chloro-3-indolyl-β-D-galactopyranoside. Reporter genes may also be used as scorable markers as alternatives to antibiotic resistance markers. Such markers are used to detect the presence or to measure the level of expression of the transferred gene. The use of scorable markers in plants to identify or tag genetically modified cells works well only when efficiency of modification of the cell is high.

3. Origins of replication, which ensure amplification of the expression cassettes or vectors according to the invention in, for example, *E. coli*. Examples which may be mentioned are ORI (origin of DNA replication), the pBR322 ori or the P15A ori (Maniatis 1989). Additional examples for replication systems functional in *E. coli*, are ColE1, pSC101, pACYC184, or the like. In addition to or in place of the *E. coli* replication system, a broad host range replication system may be employed, such as the replication systems of the P-1 Incompatibility plasmids; e.g., pRK290.

These plasmids are particularly effective with armed and disarmed Ti-plasmids for transfer of T-DNA to the plant species host.

4. Elements which are necessary for *Agrobacterium*-mediated plant transformation, such as, for example, the right and/or—optionally—left border of the T-DNA or the vir region.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Sequences

SEQ ID NO: 1: Nucleotide sequence encoding vector pBPSEW008 [LB-pNOS-bar-NOSt-::pPcUBI-gusINT-NOSt-RB]

SEQ ID NO: 2: Nucleotide sequence encoding vector pBPSMM192b [LB-pSuper-gusINT-NOSt::AtAhast-AtAhas-pAtAhas-RB]

SEQ ID NO: 3: Nucleotide sequence encoding vector pBPSLM003 [LB-OCSt-bar-pMAS::pSuper-gusINT-NOSt-RB]

FIGURES

FIG. 1: Schema of a soybean plant in V2 stage. Shown are the locations of the cotyledons, unifoliate leaf, and the above trifoliate leaves. Axillary buds are found at the junctions of the cotyledon and epicotyl and each petiole and epicotyl.

Figure 2:
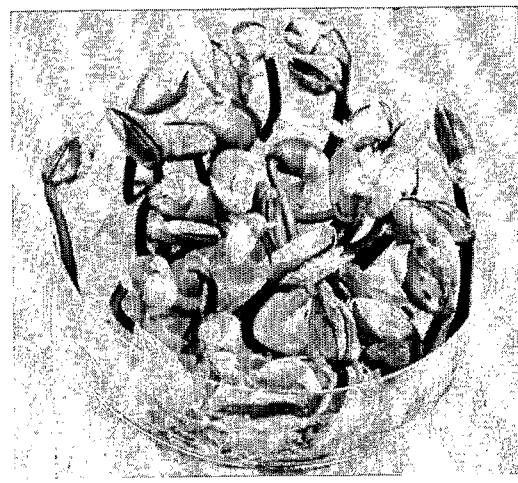

FIG. 2: Germinated soybeans of cultivar Jack about 7 days after germination.

FIG. 3: Soybean transformation method using the propagated axillary meristem explants; explant preparation. Seven-day-old seedlings are used for making propagated explants by removing the root and part of the cotyledons and placing onto 5 µM BAP containing propagation medium. The explants are prepared from new plantlets developing from the original soybean seedling. After 2 to 3 weeks on propagation medium, the axillary meristem explants are prepared from plantlets by cutting 0.5 to 1.0 cm below the axillary node on the internode, and the tip where the axillary meristems lie is cut with a scalpel to induce de novo shoot growth and allow access of target cells to the *Agrobacterium*.

FIGS. 4A-4E: Soybean transformation method using the propagated axillary meristem explants; shoot regeneration. After a 3 d co-cultivation, the explants are placed onto shoot induction medium for 35d at which time a large callus/shoot pad is formed (A, B). GUS positive shoots have been seen after 4 weeks on shoot induction medium (C). Explants with multiple shoots are then transferred to shoot elongation medium where they remain, on average, 57 to 65 days. Elongating shoots on these explants (D) are removed and placed on rooting medium 1 to 2 weeks for root development, hardened in a growth chamber for 2 to 3 weeks, then transferred to the greenhouse (E).

Figure 5:
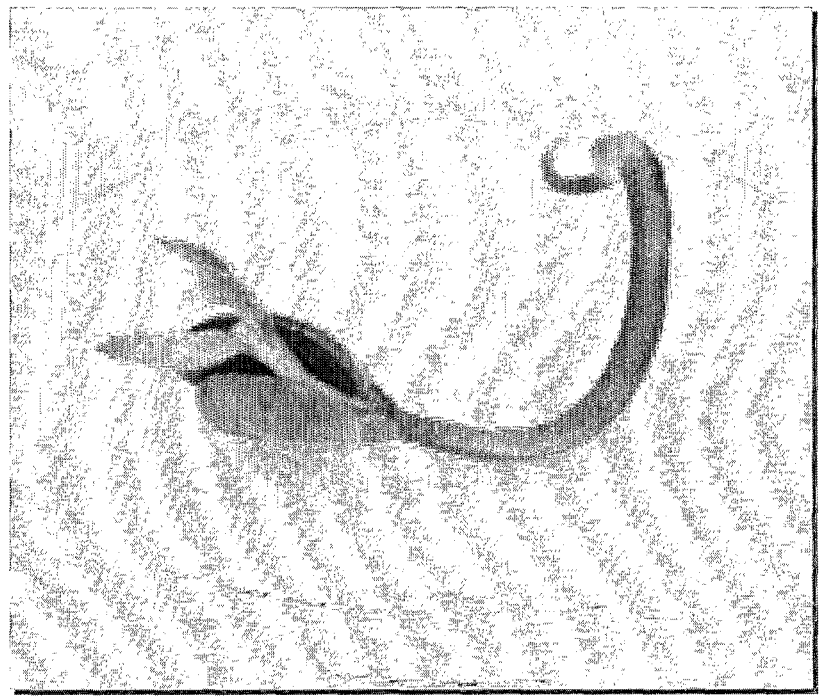
Figure 5:
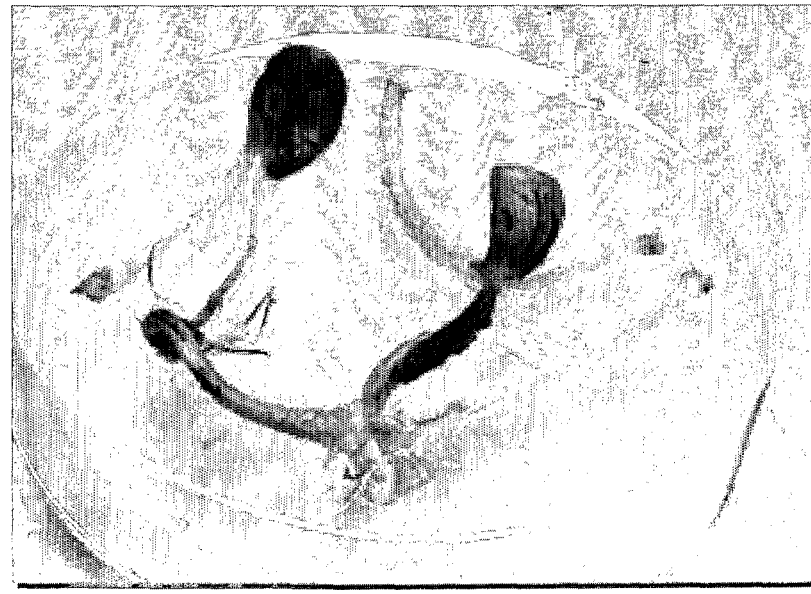

FIG. 5: Method based on seedling axillary meristem. Seven day-old seedlings (FIG. 5-1) are prepared for transformation by removing a single cotyledon, roots (optional), epicotyl above the second node (unifoliate leaf node), and the unifoliate leaves. This explant is co-cultivated with *Agrobacterium* for 5 days before placing on shoot induction medium. An example of a prepared explant 1 week on shoot induction medium is shown (FIG. 5-2).

Figure 6:
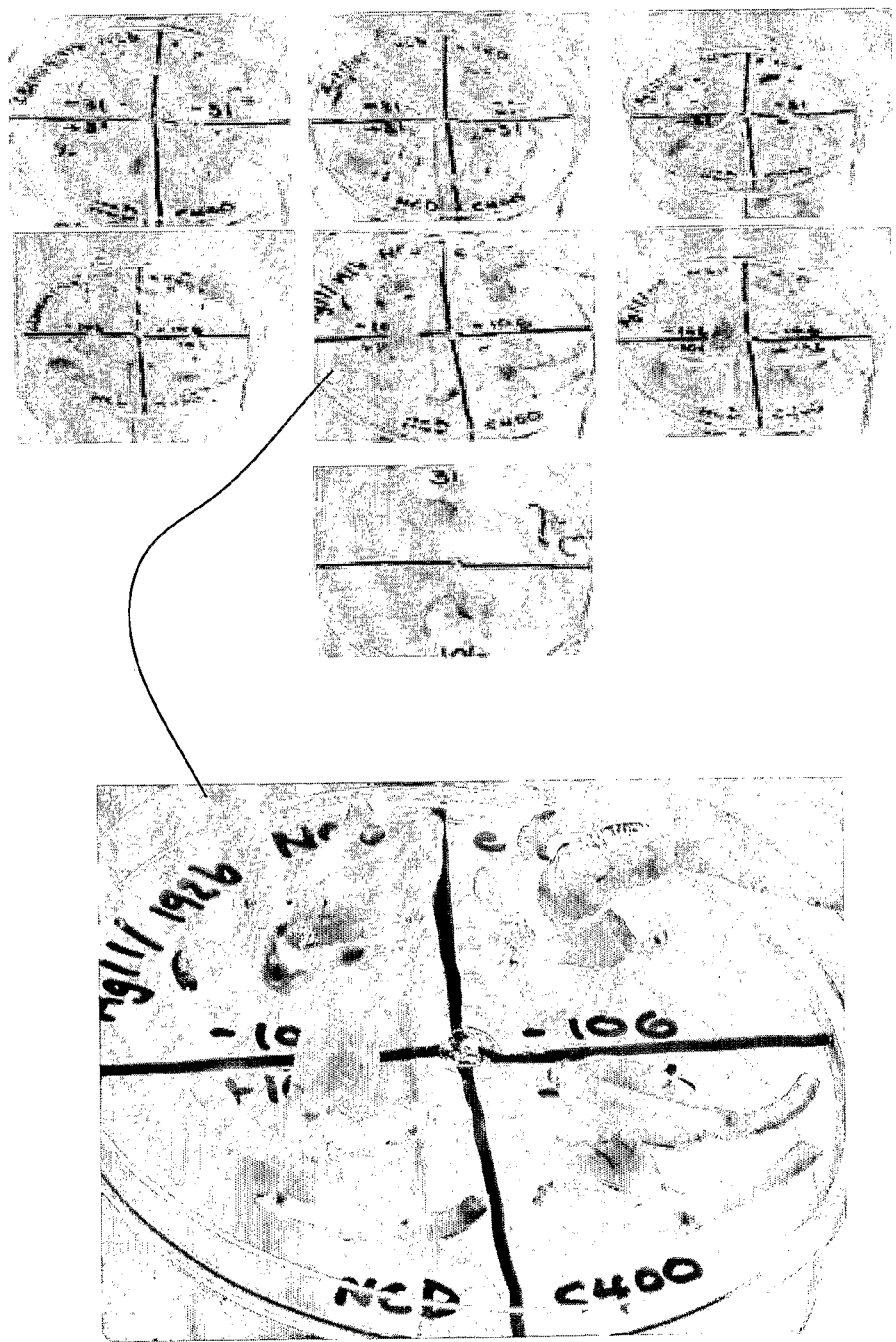

FIG. 6: Transient expression on seedling axillary meristem explants after co-cultivation with *Agrobacterium tumefaciens* on solid co-cultivation medium amended with thiol compounds.

Figure 7:
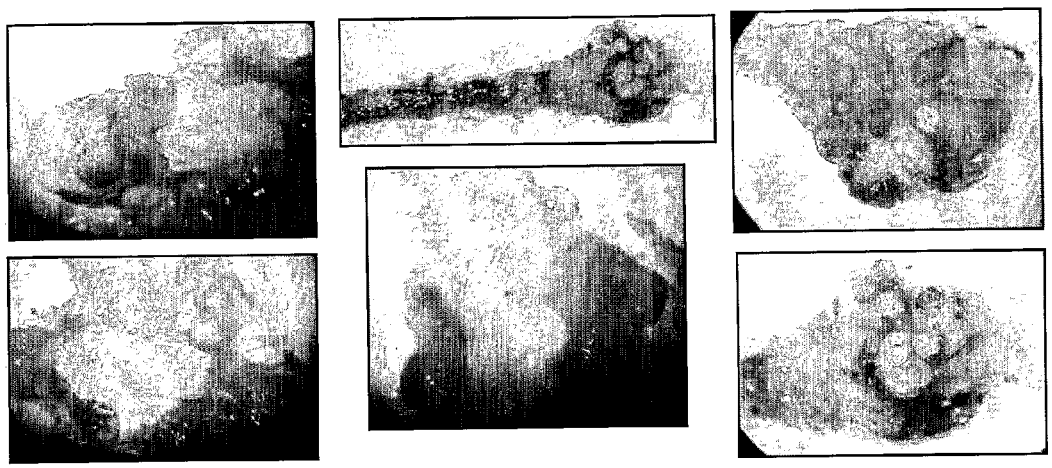
Figure 7:

FIG. 7: De novo shoot production at the primary node on the seedling explant after 2 weeks on shoot initiation medium is shown on the top panel. GUS positive shoot primordia developing on the seedling explant are shown in the lower left panel. After 4 weeks on shoot initiation medium, the explants are moved to shoot elongation medium where the shoots begin elongation 4 weeks after transfer (lower right panel).

Figure 8:
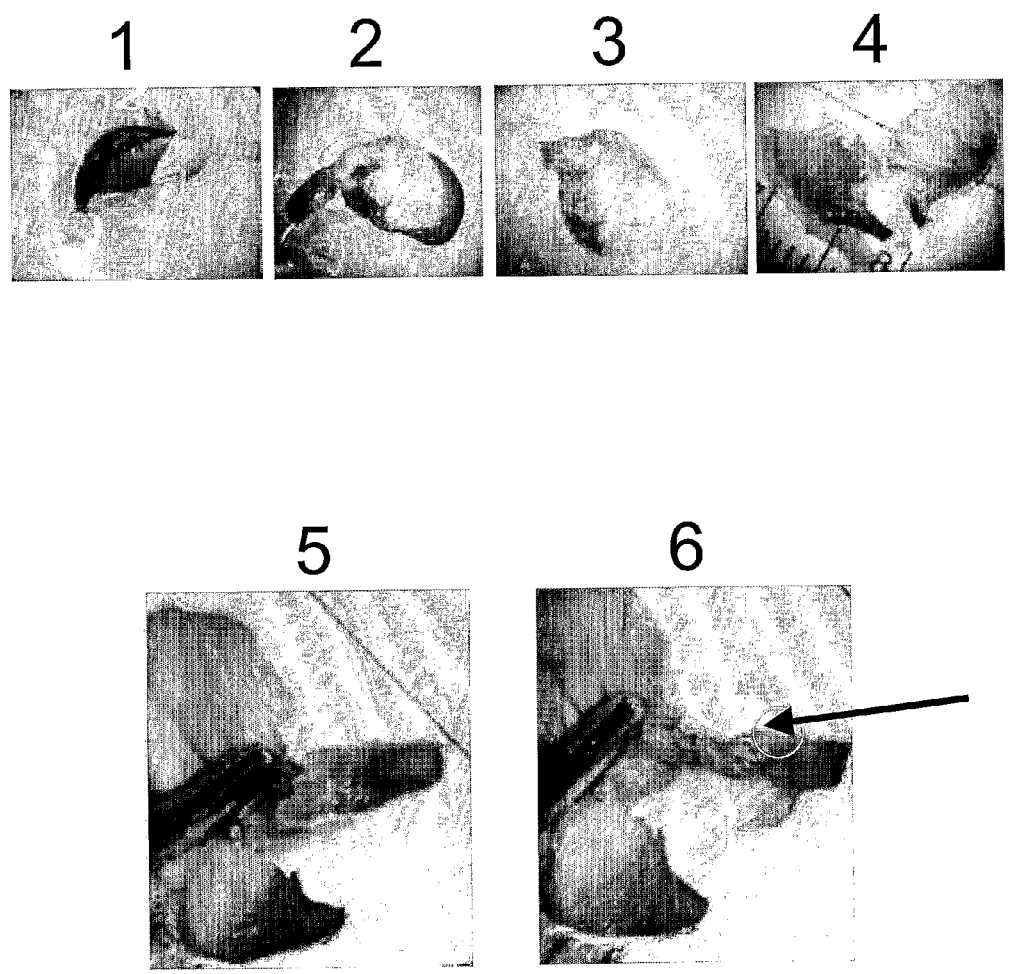

FIG. 8: Preparation of leaf axillary meristem explants. The cotyledons and epicotyl tissue are removed from the hypocotyl 2 to 4 mm below the cotyledonary node (1). To access the leaf explant, one cotyledon is removed (2) and then the epicotyl is cut above the cotyledonary-node (3). The epicotyl is bisected to release two symmetrical leaf explants (4). To induce de novo shoot production from the axillary meristem cells, all preformed shoots are carefully removed at the end of the petiole (5) and the region between the stipules, where the axillary meristem cells lie, are cut with a sharp scalpel 3 to 5 times (6).

Figure 9:
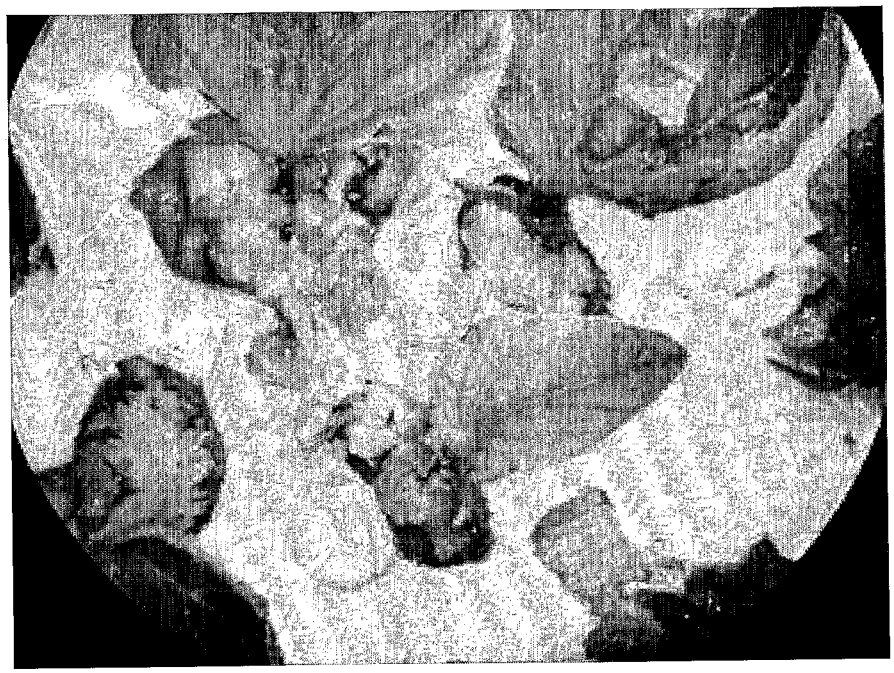
Figure 9:
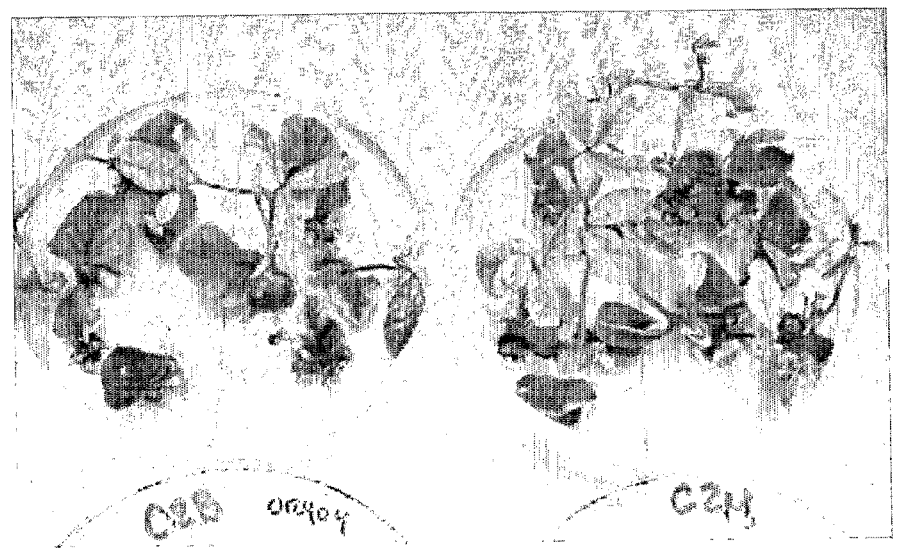

FIG. 9: De novo shoot production occurring on the base of the petiole on leaf axillary meristem explants after 2 weeks on shoot induction is shown in the top panel. After 3 to 4 weeks, the explants are transferred to shoot elongation medium where significant elongation is evident after only 18 to 36 days (bottom panel).

Figure 10:
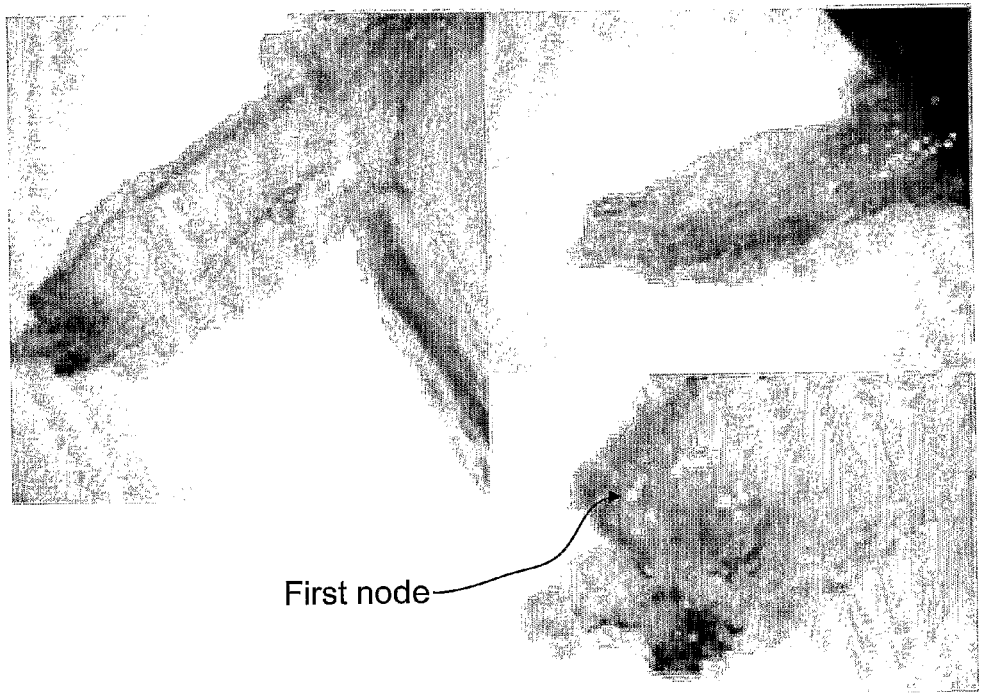

FIG. 10: Transient GUS expression on seedling axillary meristem explants after 5 days co-cultivation with *Agrobacterium*.

Figure 11:
Figure 11:
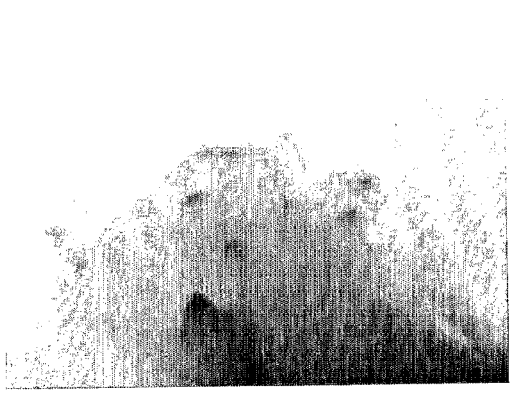
Figure 11:
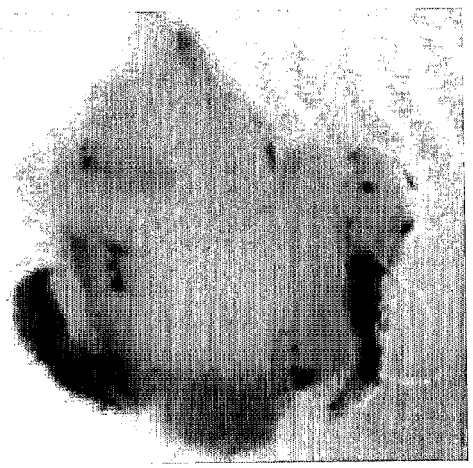

FIG. 11: Stable GUS expression on seedling axillary meristem explants after 4 weeks on shoot induction medium. Newly forming shoot primordia and larger shoots are shown with GUS positive sectors.

Figure 12A:
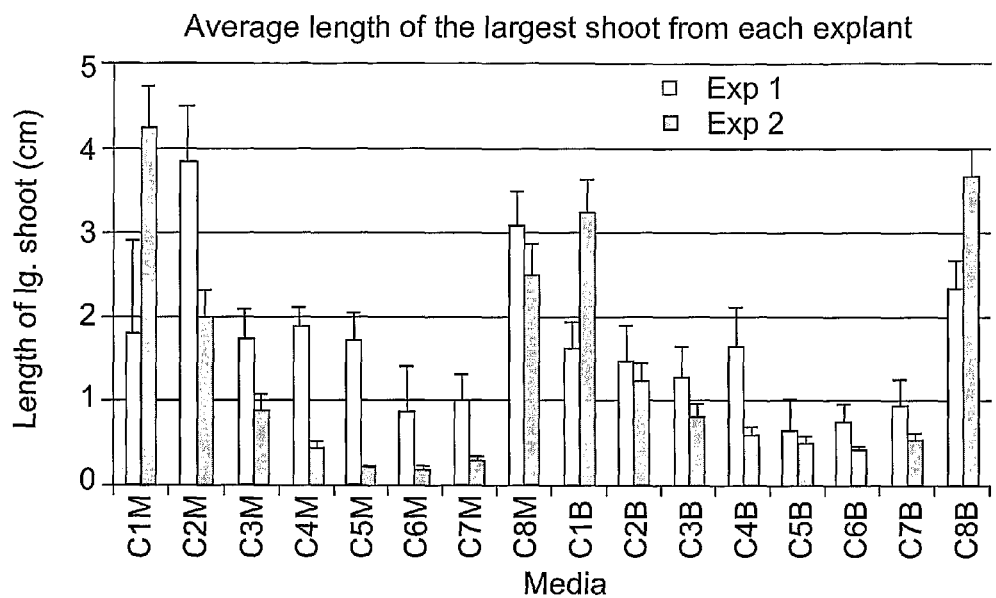
Figure 12B:
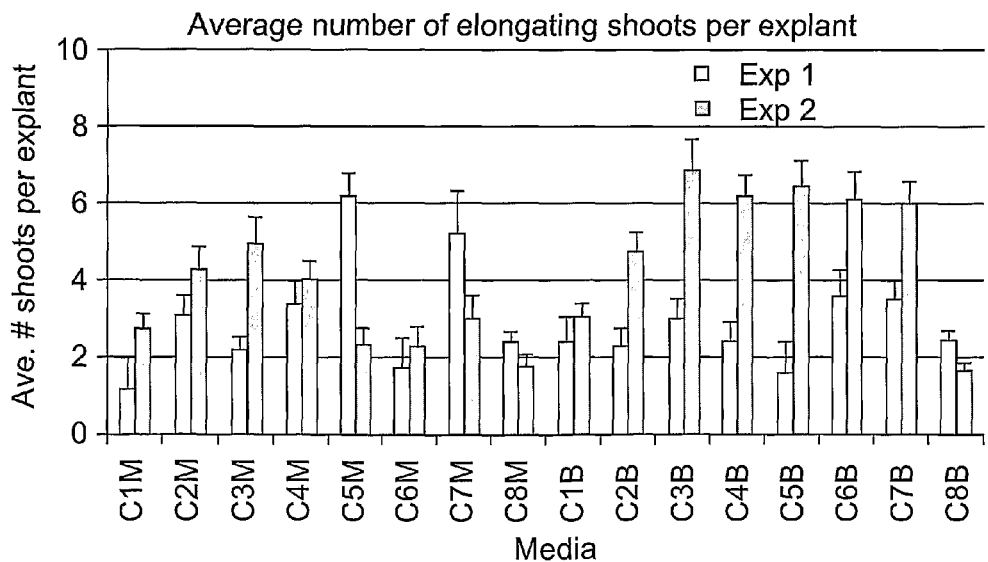

FIGS. 12A-12B: Influence of various concentrations of kinetin and BAP in shoot initiation medium on the length of the longest shoot per explant (A) and number of elongating shoots per explant (B) on leaf explants cultured 18 d on shoot elongation medium.

Figure 13:
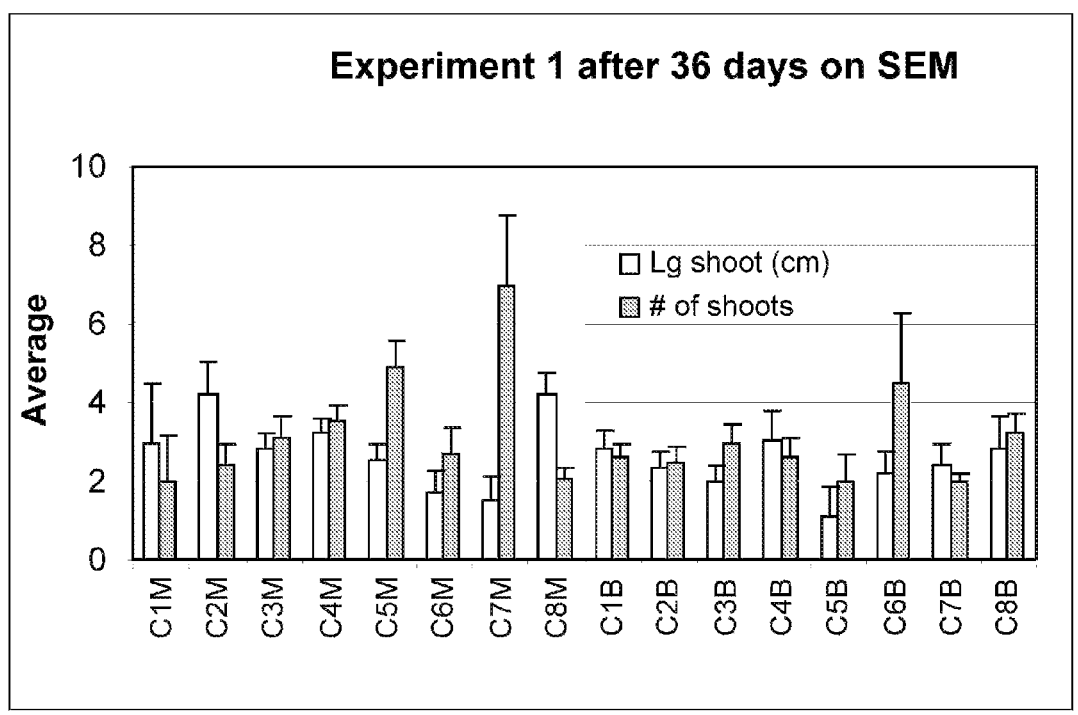

FIG. 13: Influence of various concentrations of kinetin and BAP in shoot initiation medium on the length of the longest shoot per explant and number of elongating shoots per explant on leaf explants cultured 36 d on shoot elongation medium.

Figure 14:
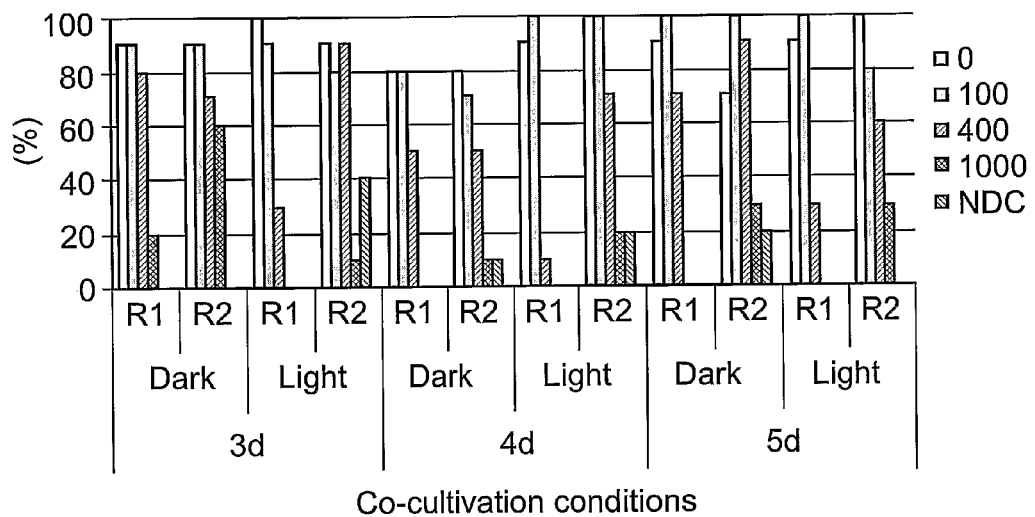

FIG. 14: The percent of leaf explants in two repetitions after 2 weeks on SIM that developed a callus shoot pad after inoculation with *A. tumefaciens* strain AGL1/pBPSEW008 and various co-cultivation conditions. (0=0 mg/L L-cysteine; 100=100 mg/L L-cysteine (0.825 mM); 400=400 mg/L L-cysteine (3.3 mM); 1000=1000 mg/L L-cysteine (8.25 mM); NDC=1 mM sodium thiolsulfate, 1 mM DTT, 1000 mg/L L-cysteine (8.25 mM))

Figure 15:
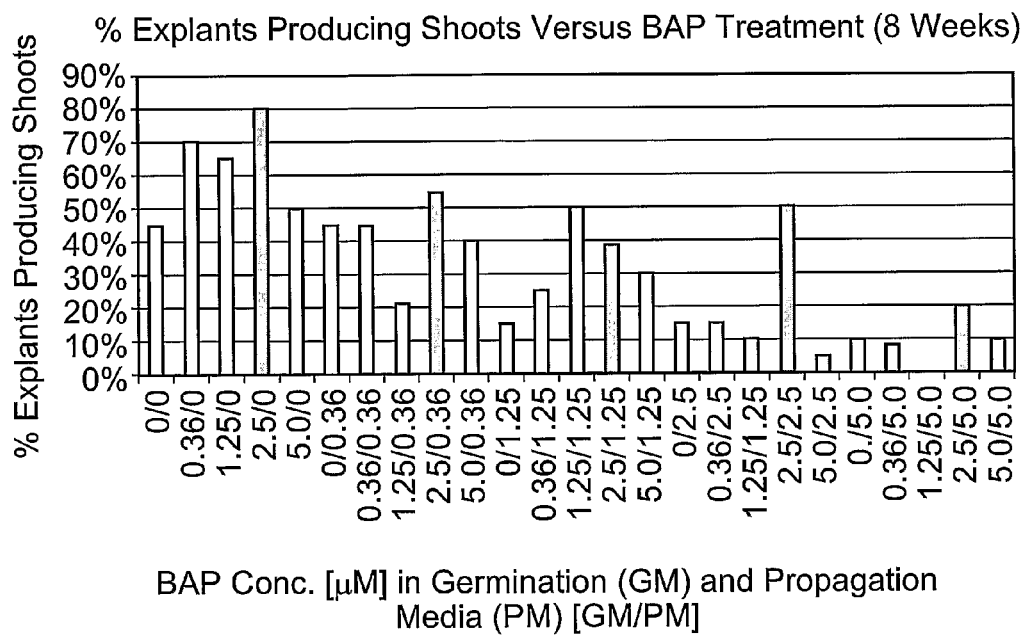
Figure 16:
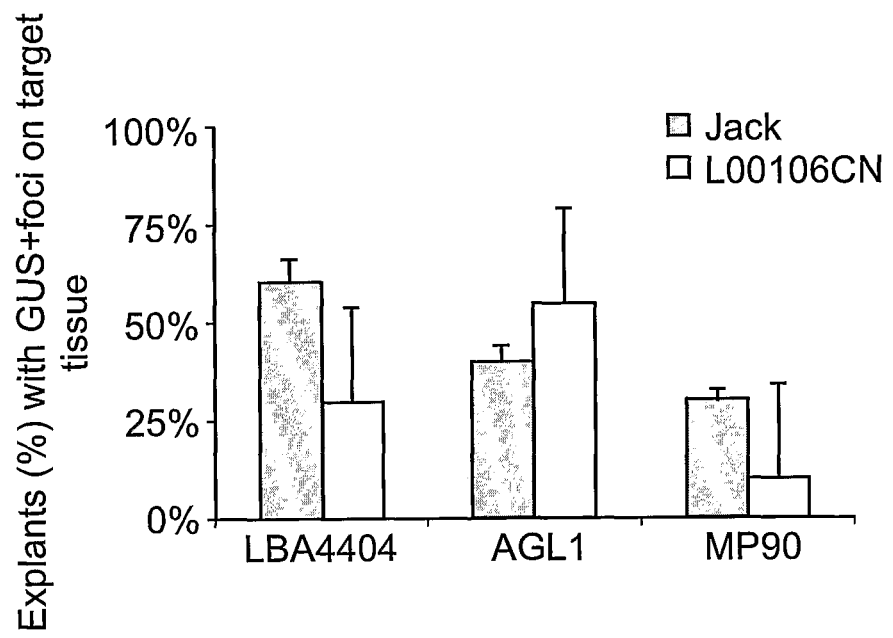

FIG. 15: Graph of propagated axillary meristem explants and response to BAP in the GM and prop medium. Percentage of explants producing elongating shoots after 4 weeks on elongation medium when exposed to various concentrations of BAP during germination and propagation FIG. 16: Evaluation of the infection capacity of three different *A. tumefaciens* strains to infect PAM explants of cultivar Jack and L00106CN. The number of explants with GUS+ foci on the target tissue were counted at 10 days post-infection FIGS. 17A-17I: Soybean transformation process using the propagated axillary meristem method. Seven-day-old seedlings (A) are used to generate a propagated plantlet by removing the root and part of the cotyledons and placing onto 5 μM BAP containing propagation medium. After 2 to 3 weeks (B), the axillary meristem explants are prepared from plantlets by removing the attached leaves and exposing the node area (C), co-cultivated with *Agrobacterium* for 3 d, then placed onto shoot induction medium for 35 d (D). Multiple shoot explants (E, F) are then transferred to shoot elongation medium where they remain, on average, 57 to 65 days. Elongating shoots on these explants (G) are removed and placed on rooting medium one to two weeks for root development (H), hardened in a growth chamber for 2 to 3 weeks, then transferred to the greenhouse (I).

EXAMPLES

Unless otherwise specified, all chemicals were from Mallinckrodt Baker, Inc. (Phillipsburg, N.J., USA), Phytotechnology Laboratories (Shawnee Mission, Kans., USA), EMD Chemicals, Inc. (Gibbstown, N.J., USA) and Sigma (St. Louis, Mo., USA).

A. Stocks Used in the Media:
1. B5 major salts
   a. 0.25 M $KNO_3$ (Potassium nitrate)
   b. 0.01 M $CaCl_2*2H_2O$ (Calcium chloride)
   c. 0.01 M $MgSO_4*7H_2O$ (Magnesium sulfate)
   d. 0.01 M $(NH_4)_2SO_4$ (Ammonium sulfate)
   e. 0.01 M $NaH_2PO_4*H_2O$ (Sodium phosphate)
2. B5 minor salts
   a. 5 mM $H_3BO_3$ (Boric acid)
   b. 10 mM $MnSO_4*H_2O$ (Manganese sulfate)
   c. 0.7 mM $ZnSO_4*7H_2O$ (Zinc sulfate)
   d. 0.45 mM KI (Potassium iodide)
   e. 0.1 mM $Na_2MoO_4*2H_2O$ (Molybdic acid)
   f. 0.01 mM $CuSO_4*5H_2O$ (Cupric sulfate)
   g. 0.01 mM $CoCl_2*6H_2O$ (Cobalt chloride)
3. B5 vitamins
   a. 0.055 M Myo-inositol
   b. 0.8 mM Nicotinic acid
   c. 0.5 mM Pyridoxine-HCl
   d. 3 mM Thiamine-HCl
4. MS major salts
   a. 0.2 M $NH_4NO_3$ (Ammonium nitrate)
   b. 0.2 M $KNO_3$ (Potassium nitrate)
   c. 30 mM $CaCl_2*2H_2O$ (Calcium chloride)
   d. 15 mM $MgSO_4*7H_2O$ (Magnesium sulfate)
   e. 12.5 mM $KH_2PO_4$ (Potassium phosphate)
5. MS minor salts
   a. 10 mM $H_3BO_3$ (Boric acid)
   b. 13 mM $MnSO_4*H_2O$ (Manganese sulfate)
   c. 3 mM $ZnSO_4*7H_2O$ (Zinc sulfate)
   d. 0.5 mM KI (Potassium iodide)
   e. 0.1 mM $Na_2MoO_4*2H_2O$ (Molybdic acid)
   f. 0.01 mM $CuSO_4*5H_2O$ (Cupric sulfate)
   g. 0.01 mM $CoCl_2*6H_2O$ (Cobalt chloride)
6. MSIII Iron
   a. 10 mM $FeSO_4*7H_2O$ (Ferrous sulfate)
   b. 10 mM $C_{10}H_{14}O_8Na_2N_2*2H_2O$ (NaEDTA)

B. Composition of Media

Unless indicated otherwise below the media can be employed for all three of the preferred explant tissues for the methods of the invention. The three method are abbreviated as follows:
a) Method A: Seedling axillary meristem—the entire seedling is employed.
b) Method B: Leaf axillary meristem—the primary or higher leaves are dissected in a way that the axillary meristematic tissue remains attached to the petioles of the leaves.
c) Method C: Propagated axillary meristem (for details see above and below)

1. Germination medium GM (solid) in 25×100 mm Petri dish or Plantcon™ (Sigma) culture boxes:
   a. 1× B5 major salts,
   b. 1× B5 minor salts,
   c. 1× MSIII iron,
   d. 2% Sucrose,
   e. 1× B5 vitamins,
   f. 5 uM BAP (optional),
   g. 0.8% Purified Agar (Sigma);
   h. pH 5.8.
2. YEP medium (solid and liquid) in Erlenmeyer flask or 15×100 mm Petri dishes:
   a. 10 g/L Bacto-peptone (Difco; Becton Dickinson & Co., Cockeysville, Md., USA),
   b. 5 g/L Yeast-extract (Difco),
   c. 5 g/L NaCl,
   d. Appropriate antibiotics for selection,
   e. 1.2% Granulated agar (Difco) solid only;
   f. pH 7.0.
3. Propagation medium MODPROP (solid) in 25×100 mm Petri dish: (METHOD C)
   a. 1× MS major salts,
   b. 1× MS minor salts,
   c. 1× MSIII iron,
   d. 1× B5 vitamins,
   e. 3% Sucrose
   f. 0.22 to 1.12 mg/L (1 μM to 5 μM) BAP (preferably about 1 μM)
   g. 0.8% Purified Agar (Sigma)
   g. pH 5.8
4. Co-cultivation medium CCM (liquid):
   a. 1/10× B5 major salts,
   b. 1/10× B5 minor salts,
   c. 1/10× MSIII iron,
   d. 1× B5 vitamins
   e. 3% Sucrose,
   f. 20 mM 2-[N-morpholino]ethanesulfonic acid (MES; $M_w$=213.26 g/Mol),
   g. 200 μM acetosyringone (AS),
   h. 0.72 μM to 1.44 μM $GA_3$ (Gibberellic acic; $M_w$=346.38 g/Mol)
   i. BAP (6-benzylaminopurine; $M_w$=225.25 g/mol): 7.5 μM.
   j. Method C only: 400 mg/L L-cysteine (3.3 mM) (Sigma)
   k. pH 5.4.
5. Co-cultivation medium CCM (solid) in 15×100 mm Petri dishes:
   a. 1/10× B5 major salts,
   b. 1/10× B5 minor salts,
   c. 1/10× MSIII iron,
   d. 1× B5 vitamins,
   e. 3% Sucrose, f. 20 mM 2-[N-morpholino]ethanesulfonic acid (MES)
g. 200 µM acetosyringone AS,
h. 0.72 µM to 1.44 µM GA$_3$ (Gibberellic acid; M$_w$=346.38 g/Mol)
i. BAP (6-benzylaminopurine; M$_w$=225.25 g/mol): 7.5 µM.
j. Thiol compounds,
   (i). 100 to 1000 g/L L-cysteine (M$_w$=121.16 g/Mol; Sigma); preferably: Method B and C: 400 mg/L L-cysteine (3.3 mM); Method A: 1 g/l (8.25 mM) L-cysteine
   (ii). 0 to 1 mM or 154.2 mg/L DTT (Fisher Scientific, Fair Lawn, N.J., USA),
   (iii). 0 to 1 mM sodium thiolsufate anhydrous (158.1 mg/L) or sodium thiolsulfate pentahydrate 245 mg/L (Mallinckrodt, Paris, Ky., USA), Method A: 1 mM dithiothrietol, 1 mM sodium thiosulfate
k. 0.5% Purified Agar;
l. pH 5.4.

6. Washing medium Modwash (liquid): (METHOD C)
   a. 1× B5 major salts,
   b. 1× B5 minor salts,
   c. 1× MSIII iron,
   d. 3% Sucrose,
   e. 1× B5 vitamins
   f. 30 mM MES,
   g. 350 mg/L Timentin™
   h. pH 5.6

6. Shoot induction medium SIM (liquid):(Method A and B)
   a. 1× B5 major salts,
   b. 1× B5 minor salts,
   c. 1× MSIII iron,
   d. 1× B5 vitamins,
   e. 3% Sucrose,
   f. 3 mM MES,
   g. 2.5 µM BAP (method B), 1 µM to 7.5 µM (preferably 1 µM) BAP (Method A)
   h. 5 uM Kinetin (only Method B)
   i. 250 mg/L Timentin™
   j. 0.8% Purified Agar;
   k. pH 5.6.

5. Shoot induction medium SIM (solid) in 20×100 mm Petri dishes:
   a. 1× B5 major salts,
   b. 1× B5 minor salts,
   c. 1× MSIII iron,
   d. 1× B5 vitamins,
   e. 3% Sucrose,
   f. 3 mM MES,
   g. 1 µM to 7.5 µM (preferably about 1 µM) BAP (Method A); 2.5 µM BAP (Method B), 5.0 µM BAP (Method C)
   h. 5 µM Kinetin (only Method A and B)
   i. 250 mg/L Timentin™
   j. Selection compound when appropriate,
   k. 0.8% Purified Agar;
   l. pH 5.6.

7. Shoot elongation medium SEM (solid) in 20×100 mm Petri dishes:
   a. 1× MS major salts,
   b. 1× MS minor salts,
   c. 1× MSIII iron,
   d. 1× B5 vitamins,
   e. 3% Sucrose,
   f. 3 mM MES,
   g. 50 mg/L L-asparagine (0.378 mM),
   h. 100 mg/L L-pyroglutamic acid (0.775 mM),
   i. 0.1 mg/L IAA (0.57 µM),
   j. 0.5 mg/L GA3 (1.44 µM),
   k. 1 mg/L trans-zeatin riboside (2.85 µM),
   l. 250 mg/L Timentin™
   m. Selection compound when appropriate,
   n. 0.8% Purified Agar;
   o. pH 5.6.

7. Rooting medium RM (solid) in 25×100 mm PYREX culture tubes (Corning Inc., New York, N.Y., USA):
   a. ½× B5 major salts,
   b. ½× B5 minor salts,
   c. 1× MSIII iron,
   d. 2% sucrose,
   e. 3 mM MES,
   f. 1 mg/L (5 µM) Indole-butyric acid (IBA, M$_w$=203.24 g/Mol) (Method A and B), 5 µM to 12.5 µM (preferably about 5 µM) IBA (Method C)
   g. 0.8% Purified Agar; Method C only: 250 mg/L Timentin
   h. pH 5.6.

Example 1

Sterilization and Germination of Soybean Seeds

Virtually any seed of any soybean variety can be employed in the method of the invention. A variety of soybean cultivar (including Jack, Williams 82, and Resnik) is appropriate for soybean transformation. Soybean seeds are sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds are removed and approximately 18 to 20 seeds are plated on solid GM medium with or without 5 µM 6-benzyl-aminopurine (BAP) in 25×100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 µM/m2s) at 25° C. are used for explant material for the three-explant types (FIG. 2). At this time, the seed coat has split, and the epicotyl with the unifoliate leaves have grown to, at minimum, the length of the cotyledons. The epicotyl should be at least 0.5 cm to avoid the cotyledonary-node tissue (since soybean cultivars and seed lots may vary in the developmental time a description of the germination stage is more accurate than a specific germination time).

For method C, The hypocotyl and one and a half or part of both cotyledons are removed from each seedling. The seedlings are then placed on propagation media for 2 to 4 weeks. The seedlings produce several branched shoots to obtain explants from (FIG. 3). The majority of the explants originate from the plantlet growing from the apical bud. These explants are preferably used as target tissue.

For inoculation of entire seedlings (Method A) or leaf explants (Method B), the seedlings are then ready for transformation (FIGS. 5 and 8).

Example 2

Growth and Preparation of *Agrobacterium* Culture

*Agrobacterium* cultures are prepared by streaking *Agrobacterium* (e.g., *A. tumefaciens* or *A. rhizogenes*) carrying the desired binary vector onto solid YEP growth medium and incubating at 25° C. until colonies appear (about 2 days). Depending on the selectable marker genes present on the Ti or Ri plasmid, the binary vector, and the bacterial chromosomes, different selection compounds will be used for *A. tumefaciens* and rhizogenes selection in the YEP solid and liquid media. Various *Agrobacterium* strains can be used for the transformation method (see above and below Example 7).

After approximately two days, a single colony (with a sterile toothpick) is picked and 50 ml of liquid YEP is inoculated with antibiotics and shaken at 175 rpm (25° C.) until an $OD_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP are inoculated with 5 μl to 3 ml of working *Agrobacterium* stock in a 500 ml Erlenmeyer flask. Shake the flask overnight at 25° C. until the $OD_{600}$ is between 0.8 and 1.0. Before preparing the soybean explants, pellet the *Agrobacteria* by centrifugation for 10 min at 5,500×g at 20° C. Resuspend the pellet in liquid CCM to the desired density ($OD_{600}$ 0.5-0.8) and place at room temperature at least 30 min before use.

Example 3

Explant Preparation and Co-Cultivation (Inoculation)

3.1 Method A: Explant Preparation on the Day of Transformation.

Seedlings at this time have elongated epicotyls from at least 0.5 cm but generally between 0.5 and 2 cm. Elongated epicotyls up to 4 cm in length have been successfully employed. Explants are then prepared with:
i) with or without some roots,
ii) with a partial, one or both cotyledons, all preformed leaves are removed including apical meristem, and the node located at the first set of leaves is injured with several cuts using a sharp scalpel (See FIG. 5).

This cutting at the node not only induces *Agrobacterium* infection but also distributes the axillary meristem cells and damages pre-formed shoots. After wounding and preparation, the explants are set aside in a Petri dish and subsequently co-cultivated with the liquid CCM/*Agrobacterium* mixture for 30 minutes. The explants are then removed from the liquid medium and plated on top of a sterile filter paper on 15×100 mm Petri plates with solid co-cultivation medium. The wounded target tissues are placed such that they are in direct contact with the medium.

3.2 Modified Method A: Epicotyl Explant Preparation

Soybean epicotyl segments prepared from 4 to 8 d old seedlings were used as explants for regeneration and transformation. Seeds of soybean cv L00106CN, 93-41131 and Jack were germinated in 1/10 MS salts or a similar composition medium with or without cytokinins for 4~8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the GUS marker gene and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a co-culture medium with L-cysteine and TTD and other chemicals such as acetosyringone for enhancing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong GUS expression were recovered. Soybean plants were regenerated from epicotyl explants. Efficient T-DNA delivery and stable transformed sectors were demonstrated.

3.3 Method B: Leaf Explants

The preparation of the leaf explant is detailed in FIG. 8. First, the cotyledon is removed from the hypocotyl. The cotyledons are separated from one another and the epicotyl is removed. The primary leaves, which consist of the lamina, the petiole, and the stipules, are removed from the epicotyl by carefully cutting at the base of the stipules such that the axillary meristems are included on the explant. To wound the explant as well as to stimulate de novo shoot formation, any pre-formed shoots are removed and the area between the stipules are cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soybean explants. Wrap five plates with Parafilm™ "M" (American National Can, Chicago, Ill., USA) and incubate for three to five days in the dark or light at 25° C.

3.4 Method C: Propagated Axillary Meristem

The preparation of the propagated axillary meristem explant is detailed in FIG. 3. Using the propagated 3-4 week-old plantlets, axillary meristem explants can be prepared from the first to the fourth node. An average of three to four explants can be obtained from each seedling. The explants are prepared from plantlets by cutting 0.5 to 1.0 cm below the axillary node on the internode and removing the petiole and leaf from the explant. The tip where the axillary meristems lie is cut with a scalpel to induce de novo shoot growth and allow access of target cells to the *Agrobacterium*. Therefore, a 0.5 cm explant includes the stem and a bud.

Once cut, the explants are immediately placed in the *Agrobacterium* suspension for 20 to 30 minutes. After inoculation, the explants are blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soybean explants. Plates are wrapped with Parafilm™ "M" (American National Can, Chicago, Ill., USA) and incubate for two to three days in the dark at 25° C.

Example 4

Shoot Induction

After 3 to 5 days co-cultivation in the dark at 25° C., the explants are rinsed in liquid SIM medium (to remove excess Agrobacterium) or Modwash medium (Method C) and blotted dry on sterile filter paper (to prevent damage especially on the lamina) before placing on the solid SIM medium. The approximately 5 explants (Method A) or 10 to 20 (Methods B and C) explants are placed such that the target tissue is in direct contact with the medium. During the first 2 weeks, the explants can be cultured with or without selective medium. Preferably, explants are transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant is placed into the medium such that it is parallel to the surface of the medium (basipetal) with the explant partially embedded into the medium.

Figure 4:
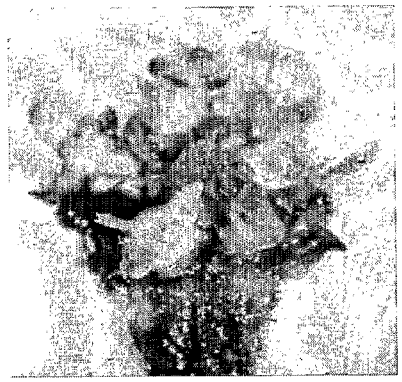
Figure 4:
Figure 4:
Figure 4:
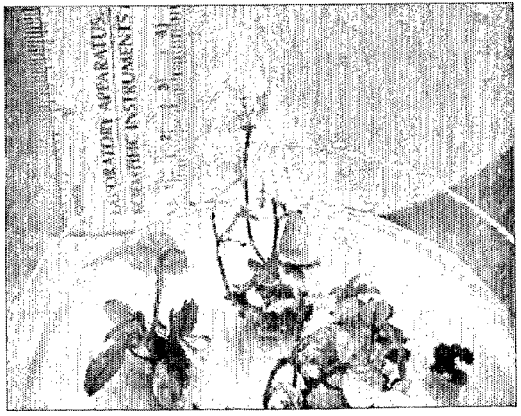
Figure 4:

Wrap plates with Scotch 394 venting tape (3M, St. Paul, Minn., USA) and place in a growth chamber for two weeks with a temperature averaging 25° C. under 18 h light/6 h dark cycle at 70-100 $\mu E/m^2 s$. Various light intensities and wavelengths, selection regimes, and SIM have been tested for this explant (Example 9). The explants will remain on the SIM medium with or without selection until de novo shoot growth occurs at the target area (e.g., axillary meristems at the first node above the epicotyl). Transfers to fresh medium can occur during this time. Explants are transferred from the SIM with or without selection to SIM with selection after about one week. At this time, there is considerable de novo shoot development at the base of the petiole of the leaf explants in a variety of SIM (Method B; FIG. 9), at the primary node for seedling explants (Method A; FIG. 7), and at the axillary nodes of propagated explants (Method C; FIG. 4).

Preferably, all shoots formed before transformation will be removed up to 2 weeks after co-cultivation to stimulate new growth from the meristems. This helps to reduce chimerism in the primary transformant and increase amplification of transgenic meristematic cells. During this time the explant may or may not be cut into smaller pieces (i.e. detaching the node from the explant by cutting the epicotyl).

Example 5

Shoot Elongation

After 2 to 4 weeks (or until a mass of shoots has formed) on SIM medium (preferably with selection), the explants will be transferred to SEM medium that will stimulate shoot elongation of the shoot primordia. This medium may or may not contain a selection compound. The frequency and length of the shoots elongating are influenced by the hormone levels, in particular BAP, in the SIM (Example 9).

After every 2 to 3 weeks, transfer the explants to fresh SEM medium (preferably containing selection) after carefully removing dead tissue. The explants should hold together and not fragment into pieces and retain somewhat healthy. The explants will continue to be transferred until the explant dies or shoots elongate. Elongated shoots >3 cm are removed and placed into RM medium for about 1 week (Method A and B), or about 2 to 4 weeks depending on the cultivar (Method C) at which time roots begin to form. In the case of explants with roots, they are transferred directly into soil. Rooted shoots are transferred to soil and hardened in a growth chamber for 2 to 3 weeks before transferring to the greenhouse. Regenerated plants obtained using this method are fertile and have produced on average 500 seeds per plant.

Transient GUS expression after 5 days of co-cultivation with *Agrobacterium tumefaciens* is widespread on the seedling axillary meristem explants especially in the regions wounding during explant preparation (Method A, FIGS. 6, 10). Explants were placed into shoot induction medium without selection to see how the primary-node responds to shoot induction and regeneration. Thus far, greater than 70% of the explants have formed new shoots at this region (FIG. 7). Expression of the GUS gene is stable after 14 days on SIM, implying integration of the T-DNA into the soybean genome. In addition, preliminary experiments have resulted in the formation of GUS positive shoots forming after 3 weeks on SIM (FIG. 7).

For Method C, the average regeneration time of a soybean plantlet using the propagated axillary meristem protocol is 14 weeks from explant inoculation. Therefore, this method has a quick regeneration time that leads to fertile, healthy soybean plants.

Example 6

Screening of Genotypes for Shoot Regeneration on the Leaf Explant

The seeds and explants were prepared as described above. A total of 17 different cultivars (9 from Soygenetics and 8 from Dairyland) were screened for shoot induction and regeneration after 2 weeks on SIM containing 5 μM Kinetin and 2.5 μM BAP. After 8 days on GM, 20 leaf explants for 6 different cultivars were prepared. Explants were placed immediately onto SIM media with 10 explants per plate. The experiment was repeated 3 times. The explants were evaluated at 3 weeks for the percentage of explants that formed a callus/shoot pad. All cultivars induced callus/shoot pads at a high percentage. The range was 85% to 100% of all explants forming a shoot pad after 3 weeks. The cultivars had a regeneration percentage greater than 95. This demonstrates, that regeneration of a callus/shoot pad on the petiole of the leaf explant is highly independent of the soybean cultivar used in this experiment. All cultivars developed a callus/shoot pad in greater than 85% of the explants that were prepared, some cultivars developed callus/shoot pads on all explants in all repetitions.

Example 7

Evaluation of the Infection Capacity of *A. tumefaciens* and *A. rhizogenes* on Leaf Explants Susceptibility of soybean to *Agrobacterium* infection is one of the most important steps in the development of a robust soybean transformation system. Genotype, developmental stage, hormonal balance and environmental conditions at the time of explant excision and preparation all affect the capacity of *Agrobacterium* to infect specific soybean tissues. The *A. tumefaciens* strain AGL1 has been used with success in soybean transformation by targeting the axillary meristems cells at the cotyledonary-node (OI-hoft & Somers (2001) Plants Cell Reports 20:706-711). The *A. rhizogenes* K599 is very effective at inducing hairy root formation and it has been demonstrated that 54 to 95% of infected cotyledons generated hairy roots from different soybean cultivars (Cho et al. (2000) Planta 210:195-204). A newly disarmed version of the *A. rhizogenes* strain K599 was included in this study. In this study, the capacity of *A. tumefaciens* and *rhizogenes* to infect the leaf explant was evaluated by analyzing transient GUS expression.

Two *Agrobacterium* strains were used: the *A. tumefaciens* strain AGL1, a derivative of AGL0 (recA::bla pTIBo542Δ Mop+ CBR)(Lazo (1991) Bio/Technology 9:963-967), and a disarmed version of *A. rhizogenes* K599 (SHA016) (pRi2659)TetR NCPPB 2659 (BASF Plant Sciences LLC, 2004). Both *Agrobacterium* strains contained the binary vector pBPSMM192b with the uidA gene under the control of the enhanced mas promoter (SuperP:pIV2GUS:nosT). On the day before explant inoculation, overnight cultures were prepared as follows: 30 ml YEP liquid containing the appropriate antibiotics were inoculated with 10-80 μl of *Agrobacterium* working stock in a baffled Erlenmeyer and shaken on an orbit shaker at 150 rpm at 28° C. for 10 to 12 hours. Once the cultures reached an $OD_{600}$ 0.5 to 0.8, the cells were pelleted by centrifugation at 3,500 rpm for 10 minutes in 50 ml falcon tubes. Cells were re-suspended in liquid CCM.

Seeds of a soybean cultivar (e.g., Jack) were sterilized and seedlings germinated as stated above. Leaf explants were prepared and immersed for 10-20 seconds in the *Agrobacterium*/CCM suspension, blotted-dry on sterile filter paper, and placed on top of filter paper on solid CCM containing 400 mg/L L-cysteine (3.3 mM). After 2 days co-cultivation, the leaf explants were rinsed in liquid SIM then placed on solid SIM containing 2.5 μM BAP and 5.0 μM kinetin for three days. After this time, transient GUS expression was evaluated on explant tissues. Two experiments were conducted. In the first experiment, two repetitions with a total of 30 explants were prepared and inoculated with AGL1. In the second experiment with one repetition, 40 explants were inoculated with AGL1 or SHA016 and assayed for GUS expression five days after inoculation.

The first experiment evaluated the ability of AGL1 to infect leaf explants. All tissues were sacrificed to GUS stain for transient expression five days after inoculation. Sixty-percent of the explants had GUS (+) foci at the cut end of the petiole were the axillary meristems are located (Table 1). In addition, other areas within the explants showed also GUS+ foci including the lamina.

TABLE 1

Intital experiment conducted tested the ability of AGL1 to infect leaf axillary meristems. GUS histochemical assay results after 6 days post-infection

|  | Total explants infected | Explants with GUS (+) foci at target areas |
| --- | --- | --- |
| Rep 1 | 10 | 6 |
| Rep 2 | 20 | 12 |

In the second experiment, both *A. tumefaciens* AGL1 and the disarmed *A. rhizogenes* strain K599 (SHA016) were successful in transferring the T-DNA into the petiole of the leaf explant. Forty percent of the explants infected with AGL1 showed GUS (+) foci in the target areas, while SHA016 showed GUS(+) foci in 4% of the target areas (Table 2). The reduction in transient GUS expression on those explants infected with SHA016 was mainly a result in tissue death during co-cultivation.

TABLE 2

The capacity of *Agrobacterium* strains AGL1 and SHA016 to infect leaf explants.

| Strain | Total explants infected | Explants with GUS (+) foci at target areas |
| --- | --- | --- |
| AGL1 | 40 | 17 |
| SH016 | 40 | 10 |

These results demonstrate the ability of disarmed *Agrobacterium tumefaciens* and *rhizogenes* strains to successfully deliver T-DNA to the cells located at or near the target area in the leaf explant.

Example 8

Optimizing Co-Cultivation Conditions for Explant Regeneration and *Agrobacterium* Infection In *Agrobacterium*-mediated transformation methods, optimization of the co-cultivation conditions is a large factor in obtaining transgenic plants. A balance between favorable *Agrobacterium* growing conditions and a healthy growth conditions for plants must be met. Common conditions that are tested include: light conditions, length of incubation, temperature, *Agrobacterium* cell density, and media components. In this study, light conditions, addition of thiol compounds to CCM (Olhoft and Somers (2001) Plants Cell Reports 20:706-711), days of incubation, and inoculation method are all considered.

In both experiments, soybean cultivar (e.g., Jack) and the *Agrobacterium tumefaciens* strain AGL1 containing the binary plasmid pBPSEW008 (SEQ ID NO: 1) was used. The binary plasmid contains nosP-bar-nosT and pUBI-gusINT-nosT. The leaf explants and *Agrobacterium* were prepared as described earlier. The final *Agrobacterium* $OD_{600}$ used for all experiments was 0.5. In the first experiment, two repetitions were made for which the following conditions were tested,
(1) addition of one of five thiol combinations added to CCM (no thiols, 100 mg/L L-cysteine (0.825 mM), 400 mg/L L-cysteine (3.3 mM), 1000 mg/L L-cysteine (8.25 mM), or 1 mM sodium thiolsulfate+1 mM DTT+ 1000 mg/L L-cysteine (8.25 mM)),
(2) 3, 4, or 5 day co-cultivation at 25° C., and
(3) incubation in the dark or under 100 μE/m2s cool white light under a 16 light/8 dark light regime.

Ten explants were prepared for each treatment. The explants were grown on SIM medium for 2 weeks after which time the percent of explants developing a callus/shoot pad were recorded.

In the second experiment, explants were prepared and subjected to the above treatments except all leaf explants were co-cultivated for 5 days and either the entire ex-plant was immersed into the *Agrobacterium*/CCM suspension for 10 minutes or the cut petiole end of the explant dipped. Ten explants were entirely immersed per treatment and 4 explants were dipped per treatment. All explants were GUS-stained immediately after co-cultivation.

In experiment 1, regeneration of a callus/shoot pad was significantly affected by the level of L-cysteine in the CCM but not the co-cultivation light conditions or the days of incubation (see FIG. 14). Between 80 to 100% of the explants co-cultivated on CCM containing no thiol compounds or 100 mg/L L-cysteine (0.825 mM), regardless of other factors tested, developed a callus/shoot pad on the petioles. However, L-cysteine levels over 400 mg/L (3.3 mM) consistently resulted in tissue death observed by bleaching of the lamina and cut end of the petiole. In experiment 2, GUS-staining on the explants with the different co-cultivation conditions revealed that CCM with thiol conditions with greater than 400 mg/L L-cysteine (3.3 mM) is favored for optimal T-DNA delivery (see Table 3).

TABLE 3

The number of GUS positive sectors on the petiole of the explants for each co-cultivation treatment for experiment 2 is given below:

| Thiol treatment | Light Conditions | Entire: explant with GUS (+) foci | Dip: explant with GUS (+) foci |
|---|---|---|---|
| 0 mg/l Cys | Light | 0/10 | 0/4 |
| 0 mg/l Cys | Dark | 1/10 | 0/4 |
| 100 mg/l Cys | Light | 6/10 | 0/4 |
| 100 mg/l Cys | Dark | 7/10 | 0/4 |
| 400 mg/l Cys | Light | 9/10 | 1/4 |
| 400 mg/l Cys | Dark | 9/10 | 3/4 |
| 1000 mg/l Cys | Light | 3/10 | 1/4 |
| 1000 mg/l Cys | Dark | 3/10 | 0/4 |
| NDC1000* | Light | 9/10 | 1/4 |
| NDC1000* | Dark | 9/10 | 2/4 |

*NDC = 1 mM Sodium thiosulfate/1 mM DTT/8.25 mM (1000 mg/L) L-Cysteine

The explants subjected to 1000 mg/L L-cysteine underwent significant bleaching therefore explaining the lower number of GUS (+) foci found on these ex-plants. This preliminary experiment also suggests that the light conditions do not play a large role in T-DNA delivery into soybean cells.

The major treatment that affected both regeneration and GUS transient expression in this set of experiments was the inclusion of thiol compounds into the CCM. The other co-culture conditions tested did not greatly influence regeneration or GUS transient expression with the numbers used in these experiments. The optimal concentration of L-cysteine was therefore found to be 400 mg/L or 3.3 mM.

Example 9

The Effect of the Shoot Initiation Medium (SIM) on Regeneration of Shoots from the Leaf Explant The culture conditions including salts, hormones, and light quality all affect the plants response to regeneration in plants. Studies comparing the effects of basal salts and hormones during shoot induction on initiation and regeneration of shoots on leaf explants has been done in pigeonpea (Dayal et al. (2003) Plant Cell Rep. 21:1072-1079). In this set of experiments, the basal salts MS and B5, levels of the cytokinins BAP and kinetin, and different light qualities were tested to see how these factors influence shoot formation and elongation on leaf explants.

Leaf explants were prepared from 7 day-old-seedlings from the Soygenetics cultivar 31 (93-41131) as stated above. The explants were randomly placed into the 16 different SIM media comprising of either MS or B5 salts and one of eight Kinetin and BAP combinations (Basic media: B5 or MS salts, B5 vitamins, MS III Iron, 3 mM MES, 3% sucrose, 0.8% purified agar, and 250 to 500 mg/L Timentin).

TABLE 4

Leaf explants were prepared and transferred to SIM that contained either B5 or MS salts with varying concentrations of kinetin and BAP.

| Code | Salts | Kinetin (µM) | BAP (µM) |
|---|---|---|---|
| C1B | B5 | 5 | 0 |
| C2B | B5 | 5 | 1 |
| C3B | B5 | 5 | 2.5 |
| C4B | B5 | 5 | 5 |
| C5B | B5 | 5 | 7.5 |
| C6B | B5 | 5 | 10 |
| C7B | B5 | 0 | 7.5 |
| C8B | B5 | 0 | 0 |
| C1M | MS | 5 | 0 |
| C2M | MS | 5 | 1 |
| C3M | MS | 5 | 2.5 |
| C4M | MS | 5 | 5 |
| C5M | MS | 5 | 7.5 |
| C6M | MS | 5 | 10 |
| C7M | MS | 0 | 7.5 |
| C8M | MS | 0 | 0 |

In experiment one, 3 repetitions were conducted in which 160 explants were pre-pared for each repetition (as detailed above) and 10 explants were randomly plated onto each of the 16 different SIM treatments. One researcher prepared all three repetitions. The explants were grown on SIM for 2 weeks before transferring five explants from Rep2 and five explants from Rep3 to SEM [1× MS major salts, 1×MS minor salts, 1×MSIII iron, 1× B5 vitamins, 3% Sucrose, 3 mM MES, 50 mg/L L-asparagine (0.378 mM), 100 mg/L L-pyroglutamic acid (0.775 mM), 0.1 mg/l IAA (0.57 µM), 0.5 mg/l GA3 (1.44 µM), 1 mg/l ZR (2.85 µM), 250 to 500 mg/L ticarcillin, 0.8% purified Agar; pH 5.6] to induce shoot elongation. Explants in this experiment were grown in a Percival chamber with a temperature averaging 25° C. under 18 h light/6 h dark cycle at >100 µE/m2s using cool white bulbs. Experiment 2 consisted of 3 repetitions in which the explants were pre-pared by 3 different researchers. Each researcher cut 160 explants and randomly placed 10 explants onto each of the 16 treatments. The explants were grown for two weeks on the respective SIM then all explants were transferred to SEM. The explants were grown in a growth chamber under a 16 h light/8 h dark cycle with a mix of cool white and GroLux lamps at <67 µE/m2s light intensity.

The number of explants that contained a callus/shoot pad was noted after 2 weeks growth on SIM. At this time, a subjective analysis of the best response of explants to the SIM media as seen from the development of the callus/shoot pad was taken from each researcher for both experiments. The influence of SIM on shoot elongation was also measured after 18 days and 36 days on SEM. The explants were scored for the average number of significantly elongating shoots per explant and the average length of the longest shoot for each explant.

The number of explants with growth of the axillary cells in the form of primordial shoots or organogenic calli was counted for each treatment. On average, among all repetitions in the two experiments, 98.6% of the explants were cut such that the axillary cells were included on the petiole (Table 5).

TABLE 5

The number of leaf explant with axillary meristem cells cut such that the axillary cells were included on the petiole.

| Exp 1 | Exp 2 |
|---|---|
| 158/160 for R1 | 159/160 for R1 |
| 155/160 for R2 | 160/160 for R2 |
| 157/160 for R3 | 159/160 for R3 |
| Average: 470/480 (97.9%) | 478/480 (99.6%) |

There was a clear difference in the callus/shoot pad growth between treatments, especially between B5 and MS salts basal media. Explants grown on MS had significant callus growth that was an intense green while explants grown on B5 mainly developed pale, green shoot primordia with insignificant callus growth. After two weeks on SIM, each researcher chose the best media for the largest, healthiest shoot pad growth. The best media for inducing shoot primordia on explants was chosen from considering observations of all three researchers across repetition 2 and 3 in experiment 1 and all three repetitions in experiment 2. The best medium is ranked as a '1'. Those treatments not chosen by any researcher is signified by a dash (–) (see Table 6).

TABLE 6

A subjective rating of the explants' response in shoot primordia formation upon exposure to different SIM media

| SIM | Exp. 1 | Exp. 2 |
|---|---|---|
| C1B | 3 | — |
| C2B | 3 | 2 |
| C3B | 2 | 1 |
| C4B | 3 | 5 |
| C5B | 2 | 5 |
| C6B | 3 | 3 |
| C7B | 3 | 6 |
| C8B | — | — |
| C1M | — | — |
| C2M | — | 4 |
| C3M | 1 | 3 |
| C4M | 3 | 5 |
| C5M | 3 | — |
| C6M | — | — |
| C7M | — | — |
| C8M | — | — |

1 to six = best to worst, (—) not chosen in any rep. by any experimenter.

From this subjective analysis, the explants on SIM with lower BAP concentrations, especially C2B, C3B, C3M, developed larger and healthier callus/shoot pads after 2 weeks. In addition, the explants grown on B5 salts also resulted in a better response in shoot induction on explants. The intensity and wavelength of the lights used in this study did not effect the formation of the callus/shoot pads after 2 weeks on SIM.

The effect of the hormones in the SIM on the length of the largest shoot per explant and the average number of elongating shoots per explant were similar for the two experiments after 18d on shoot elongation medium (FIGS. 12A, B). For both experiments, higher levels of BAP tended to result in an increase in the number of shoots beginning to elongate, however, these shoots were, in general, not as elongated. The length of the largest shoot was overall much lower in experiment 2 with the mix of light wave-lengths and low light intensity when BAP was present in the media and longer when no BAP was in the media (FIG. 12A). The BAP concentration in SIM media slightly influenced the number of shoots per explant but not as significant as the length of the largest shoot. Instead, explants on B5 basal media containing any concentration of BAP grown under the broad spectrum low light conditions tended to have more shoots per explant than the other conditions and treatments (FIG. 12B). The trend of shoot elongation on these explants did not significantly change between treatments after 36 days on SEM but for all treatments the average length of the largest shoot per explant did increase as expected (FIG. 13C). An ideal SIM would provide multiple elongating shoots per explant as well as a quick and vigorous elongation of those shoots. Based on these results, the best SIM for promoting shoot elongation are those media with no BAP or BAP at low levels, for example C2M, C4M, C8M, C1B, C4B, and C8B and high light conditions as in experiment 1.

Various shoot induction media were tested and measured for its influence on shoot formation and regeneration on the leaf explant. Explants cultured on MS basal salts in conjunction with the treatments tested lead to large amounts of dark green but friable callus growth while explants on B5 basal salts formed pa-Ie shoots with little callus growth. Media with lower levels of BAP, B5 salts, and both light regimes were the most favorable conditions in forming healthy and large pads of shoots on the leaf explant after 2 weeks on SIM. Light levels did significantly effect the elongation and formation of shoots on explants after 18d on SEM; those explants cultured on BAP with the broad spectrum but low light levels lead to more elongating shoots per explant, however, those shoots were in general shorter than other conditions tested. Therefore, leaf explants that were cultured on low levels of BAP and B5 basal salts during shoot induction and high light conditions throughout were the best for regeneration in terms of forming large, healthy callus/shoot pads that would rapidly produce multiple shoots per explant that elongated to large sizes.

Example 10

Evaluation of Two Different Donor Materials for Propagated Axillary Meristem Explants A comparison of explant material obtained from greenhouse donor plants and in vitro grown plants was made by measuring shoot regeneration from each explant. The explant material consisted of the propagated axillary meristem with the attached proximal inter-node tissue from the first to the fourth node.

Cultivar Jack was used in both growing conditions tested. For in vitro donor material, sterile seeds were sown in a Plantcon™ (SIGMA) containing ½ MS salts and 2% sucrose pH 5.7. Seedlings were maintained at 25° C. $^{16}\!/\!_{8}$ hours (light/dark) photoperiod, at a light intensity between 40 to 70 µM $m^{-2}$ $s^{-1}$. For greenhouse donor plants, seeds were sown on Metromix™ and grown in the greenhouse at 25° C. and 16 hour photoperiod. Greenhouse tissues were excised from the plant after 3 weeks. For greenhouse materials, the tissues were surface sterilized by immersion on a solution containing 5% Tween 20, followed by immersion in 70% (v/v) ethanol for 2 min then washed for 10 min in 3.5% (v/v) sodium hypochlorite solution and finally rinsed 3 times in sterile water. For in vitro donor material, no further sterilization was needed. Axillary meristem explants were placed basipetal into shoot initiation medium containing full strength MS salts and $B_5$ Gamborg's vitamins amended with either 5 µM BAP or 2 mg/L (9.1 µM) TDZ. Evaluations were made after three weeks on shoot induction medium by counting the number of shoots >0.3 mm per explant.

Explants containing the axillary meristem from both donor plants (in vitro and greenhouse) positively responded to multiple shoot induction by either BAP or TDZ (Table 7).

A higher regeneration capacity was found on axillary meristem explants from in vitro grown donor material. Of the cytokinins used, BAP had a larger shoot induction potential than TDZ. From both donor materials, explants cultured on TDZ generated large amount of callus and small shoots. Contamination was also a problem on explants derived from greenhouse grown plants.

TABLE 7

Evaluation of the regeneration capacity of axillary meristem regions from greenhouse and in vitro donor plants. Results from three repetitions (n = 212)

| Explant Source | Cytokinin | Mean # of shoots per explant (>3 mm) | SE |
| --- | --- | --- | --- |
| In vitro plant | BAP (5 uM) | 1.97 ± | 0.026 |
|  | TDZ (9.1 μM) | 0.74 ± | 0.012 |
| Greenhouse plant | BAP (5 uM) | 0.20 ± | 0.05 |
|  | TDZ (9.1 μM) | 0.32 ± | 0.033 |

Explant materials for the propagated axillary meristem transformation method have the highest shoot induction potential if they are derived from in vitro grown plants and exposed to BAP during shoot induction.

Example 11

Factors Affecting Shoot Induction Potential on Explants from in vitro Grown Plants 11.1. Effect of Culture Vessel Type on Regenerability of Axillary Meristems of Soybean An evaluation was carried out to determine if different culture vessels affected the re-generation of axillary meristem explants obtained from in vitro plantlets. Wright et al. (1987) demonstrated that soybean tissues cultured in plastic petri dishes or glass culture tubes under the same environmental growing conditions resulted in a difference in shoot regeneration and phenotypic appearances.

Seeds of cultivar Jack were surface sterilized by washing them initially in 70% (v/v) ethanol for 6 min. Seeds were then immersed in a solution that contained 25% commercial bleach (NaOCl) and 0.1% of Tween 20, stirred at 200 rpm for 20 min. Seeds were rinsed 4 times in sterile double distilled water. Germination was carried out in the light (40 to 70 μM $m^{-2} s^{-1}$) with a photoperiod of 16/8 hours (light/dark). Sterile seeds were distributed among three different culture vessels containing germination medium, (1) petri plates (150×20 mm), (2) coupled magenta boxes, and (3) Plantcon™ (SIGMA). After three weeks on the germination medium, axillary meristem explants were prepared as described above then placed basipetal into shoot initiation medium containing full strength MS salts and $B_5$ Gamborg's vitamins amended with 5 μM BAP. Regeneration capacity, measured by the average number of shoots per explant >3 mm, was conducted after 4 weeks on shoot induction.

Axillary meristem explants from plantlets germinated in the three different culture vessels have different regeneration potentials. The highest regeneration capacity was found on axillary meristem explants that were germinated on plastic petri plates; an average of 0.3 shoots per explant developed on seeds germinated in coupled Magenta boxes, 0.81 in plastic petri plates, and 0.1 in Plantcons. In addition, explants derived from the coupled magenta and Plantcon™ (SIGMA) were more difficult to remove from the plantlet and to wound presumably due to increased lignin content.

11.2. Affect of BAP Concentration in Germination Medium and/or Shoot Initiation Medium on Shoot Initiation on Propagated Axillary Meristems.

The ideal donor plant should have the ability to produce a highly regenerable axillary meristem explant and develop a large number of explants per plantlet. It was observed that when seeds were grown on hormone free medium and directly used for explant material, few axillary meristem explants could be prepared. Additionally, prolific root growth in these vessels severely limited the room and nutrients for plantlet formation. Therefore, we tested the explants ability to regenerate shoots after adding a propagation step and adding BAP to the germination medium to reduce root growth. Since BAP is also known to affect the potential of shoots to regenerate, experiments were designed to measure the regeneration capacity of explants exposed to multiple concentrations of BAP throughout germination and propagation.

Seeds were germinated as stated above with BAP concentrations of 0, 0.36, 1.25, 2.5 or 5 μM. After 7 days, the root, hypocotyl, and one cotyledon were removed and the remaining tissue placed on propagation medium (MS salts, 3% sucrose, $B_5$ vitamins, 0.8% phytagar, plus appropriate BAP) poured in Petri plate (150×20 mm). Seedlings from each BAP concentration were moved to all 5 concentrations during propagation. After 4 weeks, axillary meristem explants were prepared and transferred to shoot induction medium MS salts, 3% sucrose, $B_5$ vitamins, 5 μM BAP, 0.8% phytagar in 100× 20 mm plates. After 1 week, the material was transferred to elongation medium (MS salts, 3% sucrose, $B_5$ vitamins, 0.36 μM BAP, 0.8% phytagar) for 4 weeks before scoring for shoot elongation (shoots greater than 0.3 mm).

By removing the roots and placing the plantlets on propagation medium before explant preparation, more explants could be prepared per propagated plantlet; an average of 4 to 6 axillary meristem explants were obtained. In addition, additional cutting and propagating step did not affect the shoot induction capacity of the explants. The addition of BAP into the germination medium also tended to increase the percent of explants producing elongating shoots, especially at a concentration of 2.5 μM (FIG. 15; gray shaded bar). A general trend was found that explants in contact with higher concentrations of BAP during the propagation phase of the axillary meristem protocol produced less elongated shoots than those explants without BAP (see FIG. 15).

Addition of BAP (0.36 to 5 μM) into the germination medium did not negatively affect shoot regeneration; instead, there was a general trend towards increased shoot regeneration on seeds germinated on 2.5 μM BAP. Increased levels of BAP in the propagation medium did negatively affect shoot regeneration on explants.

11.3. Evaluation of the Effect of Two Basal Salts (MS and B5) for Germination, Propagation and Shoot Induction of Propagated Axillary Meristem Explants The composition of the salts in the culture medium is very important to the health and development of soybean plants. An experiment was conducted to compare the response of the explant's potential to initiate shoots when grown on media composed of MS basal salts or $B_5$ basal salts during germination, propagation, and shoot induction (see part [A] above for composition). Three different cultivars were used for the regeneration studies; Jack, Westag 97, and L00106CN. Seed sterilization, propagation and shoot induction was done as previously described. In addition to basal salts, 5 μM BAP was added to all three media. Two repetitions were done. The influence of the basal salts on the shoot initiation capacity was cultivar dependent. Changing the basal salts from MS to B5 resulted in a greater number of shoots per explant for cultivars L00106CN and Jack (Table 8). No significant differences in shoot formation on explants cultured on MS or B5 salts were found using the cultivar Westag 97.

TABLE 8

Evaluation of 2 media with different basal salts during germination, propagation, and shoot induction for shoot induction on propagated axillary meristems from cultivars Jack, Westag 97, and L00106CN. The mean number of shoots >0.3 mm per explant was taken after 3 weeks on shoot induction medium.

| Cultivar | n | B5 salts Mean number of shoots per PAM ± SD | n | MS salts Mean number of shoots per PAM ± SD |
|---|---|---|---|---|
| Jack | 80 | 2.20 ± 1.27 | 100 | 1.35 ± 0.35 |
| Westag 97 | 100 | 3.88 ± 0.39 | 100 | 3.40 ± 0.85 |
| L00106CN | 94 | 4.05 ± 1.48 | 72 | 2.64 ± 1.61 |

Changing the basal salts in the medium influenced the initiation of shoots on soybean PAM explants. For the cultivars Jack and Westag 97, B5 basal salts in the germination, propagation, and shoot induction media significantly increased the number of shoots produced per explant.

Example 12

Evaluation of the Regeneration Capacity of Different Public Soybean Cultivars using Propagated Axillary Meristem Explants The evaluation of the regeneration capacity of different soybean cultivars is an important component for the development of a robust soybean transformation and regeneration system. Identification of highly regenerable lines will allow more flexibility for trait development according to their source of origin. The cultivars used in two experiments included 3 US varieties, 6 Canadian varieties, and 27 Soygenetics cultivars. The cultivars included in this initial evaluation were Jack, Resnik, Williams 82 from US soybean public lines and RCAT Staples, Westag 97, RCAT Bobcat, OAC Prudence, OAC Woodstock, OAC9908 from the University of Guelph OAC (Ontario Agricultural College). Seed were surface sterilized by exposing them to 70% (v/v) ethanol for 6 min. Seeds were then immersed in a solution that contained 25% commercial bleach (NaOCl) and 0.1% Tween 20, shaken at 200 rpm for 20 min. Seeds were rinsed 4 times in sterile double distilled water. Germination was carried out in the dark for 5 to 7 days. Once germinated, roots and half of each cotyledon were removed then the remaining tissue was propagated on MSB5 medium containing 5 µM BA. Plates were placed in growth chamber conditions at 25° C. with a light intensity of (40-70 µM m$^{-2}$ s$^{-1}$) and a photoperiod of $^{16}$/s hours (light/dark). After three weeks, axillary meristem explants were prepared as described in Example 3.3 then placed basipetal into shoot initiation medium containing full strength MS salts, B$_5$ Gamborg's vitamins, and 5 µM BA. Evaluation of the total number of shoots >0.3 mm per propagated axillary meristem explant was done after 4 weeks.

Seeds and explants were prepared as described above. A completely randomized design was used for the evaluation. Two repetitions were made and two different researchers prepared the explants. A total of 40 propagated axillary meristems per cultivar were included in the evaluation. The total number of shoots >0.3 mm per propagated axillary meristem was performed after 4 weeks on shoot induction and was the main variable studied in this evaluation. A one-way analysis of variance was performed. Least square means and data were analyzed using PROC GLM (SAS Institute, Cary, N.C.). Dunnett-Hsu test at (P>0.05) was used for the multiple mean comparison having Jack as control. Analyses of residuals were also performed to confirm that the assumptions of the analysis were met.

The average number of shoots per propagated explant for 3 US varieties and 6 Canadian varieties are included in Table 9. Out of the seven cultivars tested, 5 responded to the multiple shoot induction. Cultivar Westag 97 had developed more shoots per explant than Jack. A number of soybean cultivars from different maturity groups were capable of producing a high number of multiple shoots, notably Westag 97. This trans-formation method should be suitable for a wide range of soybean cultivars.

TABLE 9

Evaluation of the shoot induction capacity of different US and Canadian soybean using propagated axillary meristems (n = 180)

| Origin | Maturity Group | Average shoots per PAM explant |
|---|---|---|
| US Cultivars | | |
| Jack (Control) | 3 | 3.0 |
| Resnik | 3 | 1.7 |
| Williams 82 | 3 | 2.4 |
| Canadian Cultivars | | |
| RCAT Staples | 2.6 | 2.6 |
| Westag 97 | 1.9 | 3.6 |
| RCAT Bobcat | 1.2 | 1.9 |
| OAC Prudence | 0 | 1.8 |
| OAC Woodstock | 0 | 1 |
| OAC 99-08 | 0 | 2.8 |

Example 13

Co-Cultivation Conditions 13.1 L-Cysteine Effect

Olhoft and Somers (2001) (Plants Cell Reports 20:706-711) demonstrated that the addition of thiol compounds (L-cysteine, sodium thiosulfate and dithiolthreitol) in the co-cultivation media enhanced transient and stable transformation of the soybean cultivar Bert when using the *Agrobacterium*-mediated cotyledonary-node transformation method (see also Olhoft et al., (2003) Planta 216:723-735). Therefore, an experiment was designed to evaluate if the addition of L-cysteine to the solid co-cultivation medium can also increase T-DNA delivery and integration to the propagated axillary meristem explants.

Explant preparation: Seeds of variety Jack were surface sterilized by exposure to 70% ethanol for 6 min then immersed in a solution that contained 25% commercial bleach (NaOCl) and 0.1% Tween 20 and stirred at 200 rpm for 20 min. Seeds were rinsed 4 times in sterile water. Germination was carried out for 7 day in the dark at 25° C. The root and half of both cotyledons were removed from the seven-day-old seedlings and imbedded into propagation media on 150×20 mm Petri plates. Plates were sealed with Parafilm™ and placed in a culture room at 25° C. in the light for 2 to 5 weeks. *A. tumefaciens* preparation and explant inoculation: *A. tumefaciens* strain AGL1 carrying the binary vector pBPSMM192b [LB-pSuper-gusINT-NOSt::AtAhast-AtAhas-pAtAhas-RB] (SEQ ID NO: 2) was used. A single colony was used to inoculate 25 to 30 ml LB media containing the appropriate antibiotics. Flasks were shaken on an orbit shaker (220 rpm) at 28° C. for 24 to 36 hours the OD$_{600}$ reached 0.8 to 1.0. The *Agrobacterium* was pelleted by centrifugation at 3500 rpm for 8 to 10 min. The bacterial cells were re-suspended in liquid co-cultivation media containing 200 μM acetosyringone. Once cut, the propagated axillary meristem explants were immediately immersed in the *A. tumefaciens* suspension and remained for 30 minutes. Infected tissues were then transferred either to a vacuum chamber (25-30 mm Hg) for 5 min or placed directly on co-cultivation media. Before transferring onto cultivation medium, explants were blotted dry on sterile filter paper. The treatment tested was the addition of 0, 400, or 800 mg/L L-cysteine into the solid co-cultivation media (0, 3.3, or 6.6 mM, respectively). Co-cultivation was carried out in the dark for 3 days at 25° C. Vacuum infiltration results in an increase of transformation efficiency in protocols which were performed without cysteine-supplementation, but has no significant effect on protocols which were performed with cysteine-supplementation.

GUS histochemical assay: Propagated axillary meristem explants infected with *A. tumefaciens* strain AGL1 were removed from the co-cultivation media after 3 days and stained with Gus overnight at 37° C. Remaining explants were transfer to shoot induction media containing 500 mg/L Timentin™. Gus histochemical assays were also performed at 10 and 45 days after inoculation.

Results: After 3 days co-cultivation, the frequency of explants with GUS$^+$ foci increased from 2.5% to 45 and 63% by the addition of 800 (6.6 mM) or 400 mg/L (3.3 mM) L-cysteine, respectively, into the solid co-cultivation medium. Explants exposed to L-cysteine underwent less browning and tissue necrosis than those explants not exposed to L-cysteine. The increases in GUS staining were also seen 10 and 45 days after co-cultivation (Table 10).

TABLE 10

Evaluation of GUS expression on explants co-cultivated in the presence or absence of L-cysteine. The frequency of propagated axillary meristems (cultivar Jack) showing GUS$^{(+)}$ foci after 3, 10, and 45 days of infection with *A. tumefaciens* AGL1 is shown. r = 2 n = 360

| L-cysteine | Day 3 | | Day 10 | | Day 45 | |
|---|---|---|---|---|---|---|
| (mg/L) | % | SE | % | SE | % | SE |
| 0 | 2.5 | 0.55 | 1.0 | 0.22 | 0.5 | 0.11 |
| 400 | 65.0 | 5.59 | 90.0 | 2.23 | 22.5 | 0.56 |
| 800 | 47.5 | 2.79 | 72.5 | 2.79 | 7.5 | 0.33 |

The addition of thiol compounds, namely L-cysteine, to solid co-cultivation medium has a beneficial effect on T-DNA delivery and integration as well as the vitality of the propagated meristem explant during and after co-cultivation.

13.2 *A. tumefaciens* Strain and Binary Vector Comparison

It is desirable to find the best *A. tumefaciens* strain and binary vector combination that will allow for efficient T-DNA delivery and integration. A comparison of three *A. tumefaciens* strains was made for the ability to infect propagated axillary meristem explants of two soybean cultivars, Jack and L00106CN. In addition, a second experiment was conducted that tested the infection capacity of *A. tumefaciens* strain, AGL1, carrying one of three different binary vectors.

Seed germination, propagation, *A. tumefaciens* and axillary meristem explant preparation, and inoculations were done as previously described. In the first experiment, three *A. tumefaciens* strains, MP90, LBA4404 and AGL1, containing the binary vector pBPSMM192b (SEQ ID NO: 2) were compared. The infected propagated axillary meristems with the 3 *A. tumefaciens* strains were removed from the co-cultivation media after 3 days and GUS stained 10 days after inoculation.

In a separate experiment, GUS expression was evaluated on explants from the cultivar L00106CN 10-days after infection with the *Agrobacterium* strain AGL1 containing the binary vectors pBPSLM003 [LB-OCSt-bar-pMAS::pSuper-gusINT-NOSt-RB] (SEQ ID NO: 3), pBPSMM192a [LB-NOSt-gusINT-pSuper::AtAhast-AtAhas-pAtAhas-RB], or pBPSMM192b [LB-pSuper-gusINT-NOSt::AtAhast-AtAhas-pAtAhas-RB] (SEQ ID NO: 2). The backbone sequence of pBPSLM003 (SEQ ID NO: 3) is different of that in pBPSMM192a and b (SEQ ID NO: 2). The vector pBPSMM192a [LB-NOSt-gusINT-pSuper::AtAhast-AtAhas-pAtAhas-RB is distinguished from the vector pBPSMM192b (SEQ ID NO: 2) by the orientation of the pSuper-gusINT-NOSt expression cassette, which is in reverse orientation.

Explants were also evaluated for GUS expression on explants that had been co-cultivated with or without 400 mg/L (3.3 mM) L-cysteine in the solid co-cultivation medium. Twenty explants of each treatment were prepared for each repetition, a total of 2 repetitions in this experiment. GUS expression was scored 10-days-post initial infection.

The number of GUS$^+$ foci on the target areas was counted on 10-day-old explants. For cultivar Jack, explants inoculated with LBA4404 (60%) had the highest frequency of GUS$^+$ sectors, followed by AGL1 and MP90. Explants from the cultivar L00106CN showed the highest frequency of GUS$^+$ sectors when inoculated with the strain AGL1 (55%). Strain MP90 had the lowest frequency of GUS positive sectors for both cultivars, although it was able to infect (see FIG. 16).

In this study, various constructs with the Super promoter driving gusA were tested to determine if the orientation of the gene on the T-DNA or the backbone sequence affects the GUS expression on inoculated explants. The average frequency of explants co-cultivated with AGL1 containing one of three binary vectors is shown in Table 11. There was no significant effect of the different binary vectors used and the level of GUS expression on the target tissue of the explant. However, a significant increase in GUS expression is evident on explants co-cultivated with 400 mg/L or 3.3 mM L-cysteine.

TABLE 11

The frequency of GUS (+) foci on explants infected with AGL1 containing three different binary vectors 10 days post-infection.

| | pBPSLM003 | | pBPSMM192a | | pBPSMM192b | |
|---|---|---|---|---|---|---|
| L-cysteine | total explants | % | total explants | % | total explants | % |
| (−) L-cysteine | 40 (6) | 15 | 40 (2) | 5 | 40 (45) | 13 |
| (+) L-cysteine | 40 (34) | 85 | 40 (31) | 77 | 40 (38) | 95 |

The explants used in this transformation method are susceptible to infection using various *Agrobacterium* strains, especially the strains LBA4404 and AGL1. It was found that L-cysteine had a much larger impact on T-DNA delivery than did the orientation or backbone sequence of the binary vector.

Example 14

Regeneration Process Throughout the Propagated Axillary Meristem Method

A robust soybean transformation system includes a quick regeneration with a limited time in tissue culture to reduce problems associated with somaclonal variation.

Figure 17:
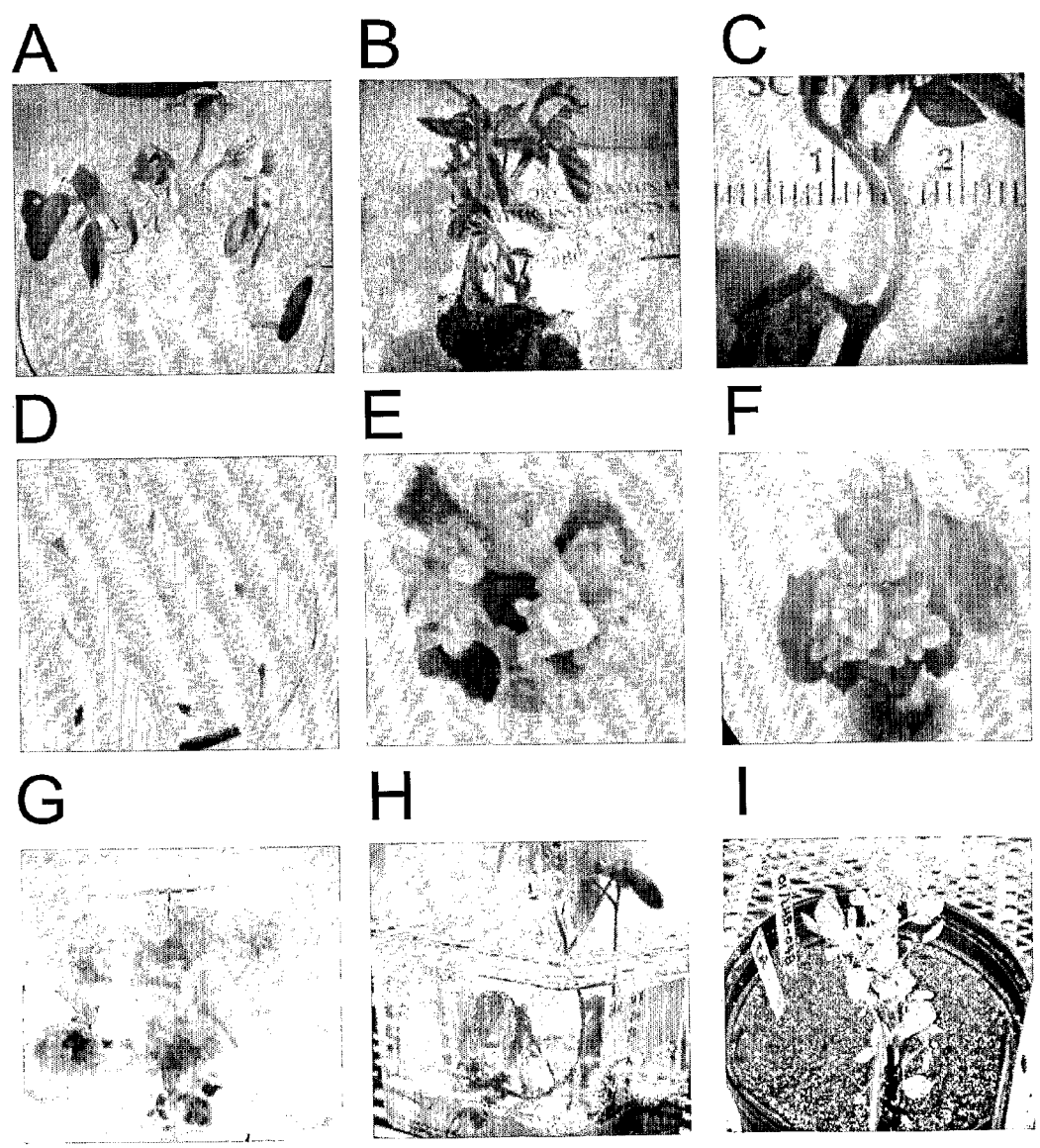

Using the transformation method outlined in above for the propagated axillary meristem method, the average regeneration time from *Agrobacterium* inoculation to plant establishment in the greenhouse was approximately 100 d. Taking the shoot induction step as day 0, elongated shoots have been obtained on average 57 to 65 days followed by a period of 3 to 4 weeks for rooting and transfer to greenhouse (FIG. 17). The transformation method described from *Agrobacterium* inoculation to greenhouse establishment is approximately 130 days on average.

What is claimed is:

1. A method for producing a transgenic soybean plant comprising the steps of:
    (a) providing an axillary meristematic tissue of a primary or higher leaf node of a soybean seedling,
    (b) co-cultivating said axillary meristematic tissue with a co-cultivation medium comprising an *Agrobacterium* comprising a transgenic T-DNA, said transgenic T-DNA comprising
        (i) at least one plant expression cassette for an agronomically valuable trait, and
        (ii) optionally one or more selectable marker genes,
    (c) transferring said co-cultivated axillary meristematic tissue on a shoot induction medium comprising
        (i) at least one plant growth factor in a concentration suitable to induce de novo shoot induction from said axillary meristematic tissue, and
        (ii) optionally one or more selection compounds which in combination with the selectable marker gene of (b) allow for identification, or selection, or identification and selection of a plant cell, tissue or plant comprising said selectable marker gene, and
        (iii) optionally one or more antibiotics suitable to inhibit *Agrobacterium* growth,
    and cultivating said co-cultivated axillary meristematic tissue until shoots are induced and developed therefrom and isolating said shoots, and
    (d) transferring said isolated shoots to a rooting medium and cultivating said shoots on said rooting medium until said shoots have formed roots, and further regenerating the so derived plantlets into mature plants, which comprise inserted into their genome a T-DNA comprising (i) said at least one plant expression cassette for an agronomically valuable trait, and
(ii) optionally said at least one selectable marker gene,
wherein the method further comprises wounding said axillary meristematic tissue prior to, during or immediately after co-cultivation of step (b), and wherein at least one of the co-cultivation medium of step (b) and the shoot induction medium of step (c) comprises at least one thiol compound.

2. The method of claim 1, wherein said method further comprises one or more additional steps selected from the group of:
(b1) transferring said co-cultivated axillary meristematic tissue after step (b) to a medium comprising
(i) at least one antibiotic suitable to inhibit *Agrobacterium* growth, and
(ii) optionally at least one plant growth factor,
wherein said medium is lacking a selection compound which in combination with the selectable marker gene of (b) would allow for identification, or selection, or identification and selection of plant cells, organs or plants comprising said selectable marker gene,
(b2) further incubating said axillary meristematic tissue after step (b) or (b1) on a shoot induction medium (SIM) comprising at least one plant growth factor, wherein said shoot induction medium is lacking a selection compound which in combination with the selectable marker gene of (b) would allow for identification, or selection, or identification and selection of plant cells, organs or plants comprising said selectable marker gene, and
(c1) transferring said shoots after step (c) to a shoot elongation medium comprising
(i) at least one plant growth factor in a concentration suitable to allow shoot elongation, and
(ii) optionally one or more selection compounds which in combination with the selectable marker gene of (b) allow for identification, or selection, or identification and selection of a plant cell, tissue or plant comprising said selectable marker gene,
and cultivating said transferred shoots on said shoot elongation medium until said shoots have elongated to a length of at least about 2 cm.

3. The method of claim 1, wherein the axillary meristematic tissue of the primary or higher node is provided in a form selected from the group consisting of:
a) the seedling axillary meristem as provided by substantially the entire seedling,
b) the leaf axillary meristem as provided by dissecting the primary or higher leaves in a way that the axillary meristematic tissue remains attached to the petioles of the leaves, and
c) propagated axillary meristem.

4. The method of claim 3, wherein the substantially entire seedling is selected from the group of material consisting of
a) an entire seedling,
b) a seedling having the roots removed,
c) a seedling having one or both cotyledons removed,
d) a seedling having the roots and one or both cotyledons removed, and
e) a seedling having the roots, both cotyledons and part of the epicotyl removed leaving the axillary meristem attached to part of the epicotyl.

5. The method of claim 1, wherein the soybean seedling is germinated for about 4 to 10 days prior to explant generation.

6. The method of claim 2, wherein the media of at least one of step (b), (b1), (b2), and (c), comprises a cytokinin.

7. The method of claim 6, wherein the cytokinin is 6-benzylaminopurine in a concentration which is between about 1 µM and about 10 µM.

8. The method of claim 2, wherein the media of at least one of step (b), (b1), (b2), (c) and (c1), comprises between about 0.1 µM and about 2 µM Gibberellic acid (GA3).

9. The method of claim 2, wherein the media of at least one of step (b) (b1), (b2), and (c) comprises at least one thiol compound.

10. The method of claim 9, wherein the thiol compound is L-cysteine in a concentration between about 1 mM and 10 mM, dithiotrietol in a concentration between about 0.1 mM to 5 mM, or sodium thiolsulfate in a concentration between 0.1 mM to 5 mM.

11. The method of claim 2, wherein the media of step (c1), or step (d), or steps (c1) and (d) comprises between about 0.01 mg/l and about 1 µM mg/l indole acetic acid (IAA), or between about 0.1 µM and about 4 µM Gibberellic acid (GA3), or between about 0.5 µM and about 6 µM zeatin riboside acid.

12. The method of claim 1, wherein the *Agrobacterium* is a strain selected from the group consisting of disarmed *Agrobacterium tumefaciens* and *Agrobacterium rhizogenes* strains.

13. The method of claim 12, wherein the *Agrobacterium* strain is a disarmed *Agrobacterium rhizogenes* K599 strain.

14. The method of claim 1, wherein the media of at least one of step (b) and (c) comprises a cytokinin.

15. The method of claim 14, wherein the cytokinin is 6-benzylaminopurine in a concentration which is between about 1 µM and about 10 µM.

16. The method of claim 1, wherein the media of at least one of step (b) and (c) comprises between about 0.1 µM and about 2 µM Gibberellic acid (GA3).

17. The method of claim 1, wherein the thiol compound is L-cysteine in a concentration between about 1 mM and 10 mM, dithiotrietol in a concentration between about 0.1 mM to 5 mM, or sodium thiolsulfate in a concentration between 0.1 mM to 5 mM.

18. The method of claim 1, wherein the media of step (d) comprises between about 0.01 mg/l and about 1 µM mg/l indole acetic acid (IAA), or between about 0.1 µM and about 4 µM Gibberellic acid (GA3), or between about 0.5 µM and about 6 µM zeatin riboside acid.

* * * * *

SEQUENCE LISTING

<160> NUMBER OF SEQ ID NOS: 3

<210> SEQ ID NO 1
<211> LENGTH: 10632
<212> TYPE: DNA
<213> ORGANISM: Unknown
<220> FEATURE:
<223> OTHER INFORMATION: vector pBPSEW008

<400> SEQUENCE: 1

```
cgctgcgctc aagtgcgcgg tacagggtcg agcgatgcac gccaagcagt gcagccgcct      60 cttcacggt gcggccttcc tggtcgatca gctcgcgggc gtgcgcgatc tgtgccgggg     120
tgagggtagg gcgggggcca aacttcacgc ctcgggcctt gcggcctcg cgcccgctcc     180 gggtgcggtc gatgattagg gaacgctcga actcggcaat gccggcgaac acggtcaaca     240
ccatgcggcc ggccggcgtg gtggtaacgc gtggtgattt tgtgccgagc tgccggtcgg     300
ggagctgttg gctggctggt ggcaggatat attgtggtgt aaacaaattg acgcttagac     360
aacttaataa cacattgcgg acgtctttaa tgtactgaat aacatccgt ttgatacttg     420 tctaaaattg gctgatttcg agtgcatcta tgcataaaaa caatctaatg acaattatta     480
ccaagcagga tcctctagaa ttcccgatct agtaacatag atgacaccgc gcgcgataat     540
ttatcctagt ttgcgcgcta tattttgttt tctatcgcgt attaaatgta taattgcggg     600
actctaatca taaaaaccca tctcataaat aacgtcatgc attacatgtt aattattaca     660
tgcttaacgt aattcaacag aaattatatg ataatcatcg caagaccggc aacaggattc     720
aatcttaaga aactttattg ccaaatgttt gaacgatcgg ggaaattcga gctcgccggc     780
gtcgacgata tcctgcaggt caaatctcgg tgacgggcag gaccggacgg ggcggtaccg     840
gcaggctgaa gtccagctgc cagaaaccca cgtcatgcca gttcccgtgc ttgaagccgg     900
ccgcccgcag catgccgcgg ggggcatatc cgagcgcctc gtgcatgcgc acgctcgggt     960
cgttgggcag cccgatgaca gcgaccacgc tcttgaagcc ctgtgcctcc agggacttca    1020
gcaggtgggt gtagagcgtg gagcccagtc ccgtccgctg gtggcggggg agacgtaca    1080 cggtcgactc ggccgtccag tcgtaggcgt tgcgtgcctt ccaggggccc gcgtaggcga    1140
tgccggcgac ctcgccgtcc acctcggcga cgagccaggg atagcgctcc cgcagacgga    1200
cgaggtcgtc cgtccactcc tgcggttcct gcggctcggt acggaagttg accgtgcttg    1260
tctcgatgta gtggttgacg atggtgcaga ccgccggcat gtccgcctcg gtggcacggc    1320
ggatgtcggc cgggcgtcgt tctgggctca tggcgcgcca gatctggatt gagagtgaat    1380
atgagactct aattggatac cgaggggaat ttatggaacg tcagtggagc atttttgaca    1440
agaaatattt gctagctgat agtgaccta ggcgactttt gaacgcgcaa taatggtttc    1500
tgacgtatgt gcttagctca ttaaactcca gaaacccgcg gctgagtggc tccttcaacg    1560
ttgcggttct gtcagttcca aacgtaaaac ggcttgtccc gcgtcatcgg cggggggtcat    1620 aacgtgactc ccttaattct ccgctcatga tcttgatccc ctgcgccatc agatccttgg    1680
cggcaagaaa gccatccagt ttactttgca gggcttccca accttaccag agggcgcccc    1740
agctggcaat tccggttcgc ttgctgtcca taaaaccgcc cagtctagct atcgccatgt    1800
aagcccactg caagctacct gctttctctt tgcgcttgcg ttttcccttg tccagatagc    1860
ccagtagctg acattcatcc ggggtcagca ccgtttctgc ggactggctt tctacgtgtt    1920
ccgcttcctt tagcagccct tgcgccctga gtgcttgcgg cagcgtgaag cttgactaga    1980
```

```
gaattcgaat ccaaaaatta cggatatgaa tataggcata tccgtatccg aattatccgt    2040
ttgacagcta gcaacgattg tacaattgct tcttaaaaa aggaagaaag aaagaaagaa     2100
aagaatcaac atcagcgtta acaaacggcc ccgttacggc ccaaacggtc atatagagta    2160
acggcgttaa gcgttgaaag actcctatcg aaatacgtaa ccgcaaacgt gtcatagtca    2220
gatcccctct tccttcaccg cctcaaacac aaaaataatc ttctacagcc tatatataca    2280 acccccccctt ctatctctcc tttctcacaa ttcatcatct ttctttctct accccccaatt  2340 ttaagaaatc ctctcttctc ctcttcattt tcaaggtaaa tctctctctc tctctctctc    2400
tctgttattc cttgttttaa ttaggtatgt attattgcta gtttgttaat ctgcttatct    2460
tatgtatgcc ttatgtgaat atctttatct tgttcatctc atccgtttag aagctataaa    2520
tttgttgatt tgactgtgta tctacacgtg gttatgttta tatctaatca gatatgaatt    2580
tcttcatatt gttgcgtttg tgtgtaccaa tccgaaatcg ttgatttttt tcatttaatc    2640
gtgtagctaa ttgtacgtat acatatggat ctacgtatca attgttcatc tgtttgtgtt    2700
tgtatgtata cagatctgaa aacatcactt ctctcatctg attgtgttgt tacatacata    2760
gatatagatc tgttatatca tttttttat taattgtgta tatatatatg tgcatagatc     2820
tggattacat gattgtgatt atttacatga ttttgttatt tacgtatgta tatatgtaga    2880
tctggacttt ttggagttgt tgacttgatt gtatttgtgt gtgtatatgt gtgttctgat    2940
cttgatatgt tatgtatgtg cagcccggat ctccgggtag gtcagtccct tatgttacgt    3000
cctgtagaaa ccccaacccg tgaaatcaaa aaactcgacg gcctgtgggc attcagtctg    3060
gatcgcgaaa actgtggaat tggtcagcgt tggtgggaaa gcgcgttaca agaaagccgg    3120
gcaattgctg tgccaggcag tttaacgat cagttcgccg atgcagatat tcgtaattat    3180
gcgggcaacg tctggtatca gcgcgaagtc tttataccga aaggttgggc aggccagcgt    3240
atcgtgctgc gtttcgatgc ggtcactcat tacggcaaag tgtgggtcaa taatcaggaa    3300
gtgatggagc atcagggcgg ctatacgcca tttgaagccg atgtcacgcc gtatgttatt    3360
gccgggaaaa gtgtacgtaa gtttctgctt ctacctttga tatatatata ataattatca    3420
ttaattagta gtaatataat attcaaata tttttttcaa aataaaagaa tgtagtatat     3480
agcaattgct tttctgtagt ttataagtgt gtatatttta atttataact tttctaatat    3540
atgaccaaaa tttgttgatg tgcaggtatc accgtttgtg tgaacaacga actgaactgg    3600
cagactatcc cgccgggaat ggtgattacc gacgaaaacg gcaagaaaaa gcagtcttac    3660
ttccatgatt tctttaacta tgccggaatc catcgcagcg taatgctcta caccacgccg    3720
aacacctggg tggacgatat caccgtggtg acgcatgtcg cgcaagactg taaccacgcg    3780
tctgttgact ggcaggtggt ggccaatggt gatgtcagcg ttgaactgcg tgatgcggat    3840
caacaggtgg ttgcaactgg acaaggcact agcgggactt gcaagtggt gaatccgcac    3900 ctctggcaac cgggtgaagg ttatctctat gaactgtgcg tcacagccaa agccagaca    3960 gagtgtgata tctacccgct tcgcgtcggc atccggtcag tggcagtgaa gggcgaacag    4020
ttcctgatta ccacaaacc gttctacttt actggctttg gtcgtcatga agatgcggac    4080
ttgcgtggca aaggattcga taacgtgctg atggtgcacg accacgcatt aatggactgg    4140
attggggcca actcctaccg tacctcgcat taccccttacg ctgaagagat gctcgactgg    4200
gcagatgaac atggcatcgt ggtgattgat gaaactgctg ctgtcggctt taacctctct    4260
ttaggcattg gtttcgaagc gggcaacaag ccgaaagaac tgtacagcga agaggcagtc    4320
aacggggaaa ctcagcaagc gcacttacag gcgattaaag agctgatagc gcgtgacaaa    4380
```

```
aaccacccaa gcgtggtgat gtggagtatt gccaacgaac cggatacccg tccgcaaggt   4440
gcacgggaat atttcgcgcc actggcggaa gcaacgcgta aactcgaccc gacgcgtccg   4500
atcacctgcg tcaatgtaat gttctgcgac gctcacaccg ataccatcag cgatctcttt   4560
gatgtgctgt gcctgaaccg ttattacgga tggtatgtcc aaagcggcga tttggaaacg   4620
gcagagaagg tactggaaaa agaacttctg gcctggcagg agaaactgca tcagccgatt   4680
atcatcaccg aatacggcgt ggatacgtta gccgggctgc actcaatgta caccgacatg   4740
tggagtgaag agtatcagtg tgcatggctg gatatgtatc accgcgtctt tgatcgcgtc   4800
agcgccgtcg tcggtgaaca ggtatggaat ttcgccgatt ttgcgacctc gcaaggcata   4860
ttgcgcgttg gcggtaacaa gaaagggatc ttcactcgcg accgcaaacc gaagtcggcg   4920
gcttttctgc tgcaaaaacg ctggactggc atgaacttcg gtgaaaaacc gcagcaggga   4980
ggcaaacaat gaatcaacaa ctctcctggc gcaccatcgt cggctacagc ctcgggaatt   5040
gctaccgagc tcgaatttcc ccgatcgttc aaacatttgg caataaagtt tcttaagatt   5100
gaatcctgtt gccggtcttg cgatgattat catataattt ctgttgaatt acgttaagca   5160
tgtaataatt aacatgtaat gcatgacgtt atttatgaga tgggttttta tgattagagt   5220
cccgcaatta tacatttaat acgcgataga aaacaaaata tagcgcgcaa actaggataa   5280
attatcgcgc gcggtgtcat ctatgttact agatcgggaa ttggcgatcg cagcttggcg   5340
taatcatggt catagctgtt tcctactaga tctgattgtc gtttcccgcc ttcagtttaa   5400
actatcagtg tttgacagga tatattggcg ggtaaaccta agagaaaaga gcgtttatta   5460
gaataatcgg atatttaaaa gggcgtgaaa aggtttatcc gttcgtccat ttgtatgtcc   5520
atgtgtttta tggacagcaa gcgaaccgga attgccagct ggggcgccct ctggtaaggt   5580
tgggaagccc tgcaaagtaa actggatggc tttcttgccg ccaaggatct gatggcgcag   5640
gggatcaaga tctgatcaag agacaggatg aggatcgttt cgcatgattg aacaagatgg   5700
attgcacgca ggttctccgg ccgcttgggt ggagaggcta ttcggctatg actgggcaca   5760
acagacaatc ggctgctctg atgccgccgt gttccggctg tcagcgcagg gcgcccggt   5820 tcttttttgtc aagaccgacc tgtccggtgc cctgaatgaa ctgcaggacg aggcagcgcg   5880
gctatcgtgg ctggccacga cgggcgttcc ttgcgcagct gtgctcgacg ttgtcactga   5940
agcgggaagg gactggctgc tattgggcga agtgccgggg caggatctcc tgtcatccca   6000
ccttgctcct gccgagaaag tatccatcat ggctgatgca atgcggcggc tgcatacgct   6060
tgatccggct acctgcccat tcgaccacca agcgaaacat cgcatcgagc gagcacgtac   6120
tcggatggaa gccggtcttg tcgatcagga tgatctggac gaagagcatc aggggctcgc   6180
gccagccgaa ctgttcgcca ggctcaaggc gcgcatgccc gacggcgagg atctcgtcgt   6240
gacccatggc gatgcctgct tgccgaatat catggtggaa aatggccgct ttctggatt   6300 catcgactgt ggccggctgg gtgtggcgga ccgctatcag acatagcgt tggctacccg   6360 tgatattgct gaagagcttg gcggcgaatg ggctgaccgc ttcctcgtgc tttacggtat   6420
cgccgctccc gattcgcagc gcatcgcctt ctatcgcctt cttgacgagt cttctgaat   6480 tgaaaaagga agaatgcatg accaaaatcc cttaacgtga gttttcgttc cactgagcgt   6540
cagacccccg agaaaagatc aaaggatctt cttgagatcc ttttttttctg cgcgtaatct   6600 gctgcttgca aacaaaaaaa ccaccgctac cagcggtggt ttgtttgccg gatcaagagc   6660
taccaactct ttttccgaag gtaactggct tcagcagagc gcagatacca atactgtcc   6720 ttctagtgta gccgtagtta ggccaccact tcaagaactc tgtagcaccg cctacatacc   6780
```

```
tcgctctgct aatcctgtta ccagtggctg ctgccagtgg cgataagtcg tgtcttaccg    6840
ggttggactc aagacgatag ttaccggata aggcgcagcg gtcgggctga acgggggtt     6900 cgtgcacaca gcccagcttg gagcgaacga cctacaccga actgagatac ctacagcgtg    6960
agctatgaga aagcgccacg cttcccgaag ggagaaaggc ggacaggtat ccggtaagcg    7020
gcagggtcgg aacaggagag cgcacgaggg agcttccagg gggaaacgcc tggtatcttt    7080
atagtcctgt cggttttcgc cacctctgac ttgagcgtcg attttgtga tgctcgtcag     7140 gggggcggag cctatggaaa aacgccagca acgcggcctt tttacggttc ctggcctttt    7200
gctggccttt tgctcacatg ttctttcctg cgttatcccc tgattctgtg gataaccgta    7260
ttaccgcctt tgagtgagct gataccgctc gccgcagccg aacgaccgag cgcagcgagt    7320
cagtgagcga ggaagcggaa gagcgcctga tgcggtattt tctccttacg catctgtgcg    7380
gtatttcaca ccgcatatgg tgcactctca gtacaatctg ctctgatgcc gcatagttaa    7440
gccagtatac actccgctat cgctacgtga ctgggtcatg gctgcgcccc gacacccgcc    7500
aacacccgct gacgcgccct gacgggcttg tctgctcccg gcatccgctt acagacaagc    7560
tgtgaccgtc tccgggagct gcatgtgtca gaggttttca ccgtcatcac cgaaacgcgc    7620
gaggcagggt gccttgatgt gggcgccggc ggtcgagtgg cgacggcgcg gcttgtccgc    7680
gccctggtag attgcctggc cgtaggccag ccatttttga gcggcagcg gccgcgatag     7740 gccgacgcga agcggcgggg cgtagggagc gcagcgaccg aagggtaggc gcttttttgca   7800 gctcttcggc tgtgcgctgg ccagacagtt atgcacaggc caggcgggtt ttaagagttt    7860
taataagttt taaagagttt taggcggaaa aatcgccttt tttctctttt atatcagtca    7920
cttacatgtg tgaccggttc ccaatgtacg gctttgggtt cccaatgtac gggttccggt    7980
tcccaatgta cggctttggg ttcccaatgt acgtgctatc cacaggaaag agaccttttc    8040 gaccttttc cctgctagg gcaatttgcc ctagcatctg ctccgtacat taggaaccgg      8100
cggatgcttc gccctcgatc aggttgcggt agcgcatgac taggatcggg ccagcctgcc    8160
ccgcctcctc cttcaaatcg tactccggca ggtcatttga cccgatcagc ttgcgcacgg    8220
tgaaacagaa cttcttgaac tctccggcgc tgccactgcg ttcgtagatc gtcttgaaca    8280
accatctggc ttctgccttg cctgcggcgc ggcgtgccag gcggtagaga aaacggccga    8340
tgccgggatc gatcaaaaag taatcggggt gaaccgtcag cacgtccggg ttcttgcctt    8400
ctgtgatctc gcggtacatc caatcagcta gctcgatctc gatgtactcc ggccgcccgg    8460
tttcgctctt tacgatcttg tagcggctaa tcaaggcttc accctcggat accgtcacca    8520
ggcggccgtt cttggccttc ttcgtacgct gcatggcaac gtgcgtggtg tttaaccgaa    8580
tgcaggtttc taccaggtcg tctttctgct ttccgccatc ggctcgccgg cagaacttga    8640
gtacgtccgc aacgtgtgga cggaacacgc ggccgggctt gtctcccttc ccttcccggt    8700
atcggttcat ggattcggtt agatgggaaa ccgccatcag taccaggtcg taatcccaca    8760
cactggccat gccggccggc cctgcgaaaa cctctacgtg cccgtctgga agctcgtagc    8820
ggatcacctc gccagctcgt cggtcacgct tcgacagacg gaaaacggcc acgtccatga    8880
tgctgcgact atcgcgggtg cccacgtcat agagcatcgg aacgaaaaaa tctggttgct    8940
cgtcgccctt gggcggcttc ctaatcgacg gcgcaccggc tgccggcggt tgccgggatt    9000
ctttgcggat tcgatcagcg gccgcttgcc acgattcacc ggggcgtgct tctgcctcga    9060
tgcgttgccg ctgggcggcc tgcgcggcct tcaacttctc caccaggtca tcacccagcg    9120
ccgcgccgat ttgtaccggg ccggatggtt tgcgaccgct cacgccgatt cctcgggctt    9180
```

```
gggggttcca gtgccattgc agggccggca gacaacccag ccgcttacgc ctggccaacc   9240
gcccgttcct ccacacatgg ggcattccac ggcgtcggtg cctggttgtt cttgattttc   9300
catgccgcct cctttagccg ctaaaattca tctactcatt tattcatttg ctcatttact   9360
ctggtagctg cgcgatgtat tcagatagca gctcggtaat ggtcttgcct tggcgtaccg   9420
cgtacatctt cagcttggtg tgatcctccg ccggcaactg aaagttgacc cgcttcatgg   9480
ctggcgtgtc tgccaggctg gccaacgttg cagccttgct gctgcgtgcg ctcggacggc   9540
cggcacttag cgtgtttgtg cttttgctca ttttctcttt acctcattaa ctcaaatgag   9600
ttttgattta atttcagcgg ccagcgcctg gacctcgcgg gcagcgtcgc cctcgggttc   9660
tgattcaaga acggttgtgc cggcggcggc agtgcctggg tagctcacgc gctgcgtgat   9720
acgggactca agaatgggca gctcgtaccc ggccagcgcc tcggcaacct caccgccgat   9780
gcgcgtgcct ttgatcgccc gcgacacgac aaaggccgct gtagccttc catccgtgac    9840 ctcaatgcgc tgcttaacca gctccaccag gtcggcggtg gcccatatgt cgtaagggct   9900
tggctgcacc ggaatcagca cgaagtcggc tgccttgatc gcggacacag ccaagtccgc   9960
cgcctggggc gctccgtcga tcactacgaa gtcgcgccgg ccgatggcct tcacgtcgcg  10020
gtcaatcgtc gggcggtcga tgccgacaac ggttagcggt tgatcttccc gcacggccgc  10080
ccaatcgcgg gcactgccct ggggatcgga atcgactaac agaacatcgg ccccggcgag  10140
ttgcagggcg cgggctagat gggttgcgat ggtcgtcttg cctgacccgc ctttctggtt  10200
aagtacagcg ataaccttca tgcgttcccc ttgcgtattt gtttatttac tcatcgcatc  10260
atatacgcag cgaccgcatg acgcaagctg ttttactcaa atacacatca ccttttaga   10320 cggcggcgct cggtttcttc agcggccaag ctggccggcc aggccgccag cttggcatca  10380
gacaaaccgg ccaggatttc atgcagccgc acggttgaga cgtgcgcggg cggctcgaac  10440
acgtacccgg ccgcgatcat ctccgcctcg atctcttcgg taatgaaaaa cggttcgtcc  10500
tggccgtcct ggtgcggttt catgcttgtt cctcttggcg ttcattctcg gcggccgcca  10560
gggcgtcggc ctcggtcaat gcgtcctcac ggaaggcacc gcgccgcctg gcctcggtgg  10620
gcgtcacttc ct                                                       10632

<210> SEQ ID NO 2
<211> LENGTH: 17396
<212> TYPE: DNA
<213> ORGANISM: Unknown
<220> FEATURE:
<223> OTHER INFORMATION: vector pBPSMM192b

<400> SEQUENCE: 2
ggctggtggc aggatatatt gtggtgtaaa caaattgacg cttagacaac ttaataacac     60
attgcggacg tttttaatgt actgaattaa cgccgaatta agctcaattg actagtggcg    120
cgcccacgtg ttaattaacg gtccgaggcc tcctcagcaa gctgttaacg cgatcgcgct    180
gaggcggacc gcacgtggaa ttcgagctcg gtacccgggg atcctctaga ttatgtattt    240
ccaactttca ttaacaatat aatcgcatat aaatgaaaaa tcgtttccag gataatattt    300
tgatgaaatc tcatattatt gttcgtactc ggattgatgt tgaaggcttg aagcgcttca    360
aattatagac cagattattt aagttttttct tttgttact ccatatcaat ttgatccatt    420
atactaccta agaaaattta ggtaacatag aattatttat tgttatagta aaaaaaagga    480
aaaccacaaa aataatctac ttttacgtat atactatttt catgacataa gtaattaagt    540
tgtacaactt ttttttaatg aaaagagaga gtaaatttat catgttcatg tgtagttacc    600
```

```
tcgtgaataa ccgacggtta tatagacgcc taacatgaat tgttcagttg aagacagttc    660
aaaacatgtg tttcactcta aaatcctcaa caaaaaaaaa gtgttaaaat tgtaaacct     720 ctttcaagca aaaaagaaa  aagtgttaga atcccaagat tctttcataa tccggaatct    780
tggctgaaaa cgtataaaag agattgacgt agtaacaagg agtcttggta tgcttccatg    840 cttttatcc  ttttttgtca tggaaccatg atttggttac catttattat gtaaccgaaa    900
ttttcattgt aataatgaat atttaaattt ttagcaaaaa aaaacaaaaa aaacaagga     960 gtcttgtctt cgttctcaaa tttcagagct cttgcacttt tcaagagttt tactttgatg   1020
agtgagacat ttgtcttttt agtgtttatt ttctaaactt aaaatagtag catcaacatc   1080
actcaattat aattcttaag atgttgtaga aaaatatttt atagatggaa agtaatcgat   1140
attaagacaa ataagaaacc aaaccggact tgtgttcag  accgaatcaa atctgaattg   1200
gagaaattat ggtggaggcg aaagtcaacg gaactaaagt ataaaaccaa atgtcaaaaa   1260
taaaacccaa ttttcatcct taaacgaacc tgctgaaacc ctaatttcga ttaccaattc   1320
cgatctaaaa agaagtcatg gaagccattg attccgcaat cgatcctctc agagatttcg   1380
ctaagagcag tgttcgtctc gtccagcgct gtcacaaacc cgatcgcaag ggtaacgcct   1440
tttctcaaaa aaatctcatt tccgattttt gatctgtaga ttagggtttt ctgaaatttt   1500
gatatcattt gtaattgaat tggttatcag aattcacgaa agtagctgtg cgtacggcga   1560
ttggatttgt ggtgatggga ttcgttggat tcttcgtgaa gctcgttttc atcccaatca   1620
acaacatcat cgttggatct tcttagtgta gtactttctt tacgaggtaa ttgatctcgc   1680
attatatatc tacattttgg ttatgttact tgacatatag tcattgattc aatagttctg   1740
ttaattcctt taaagatcat tttgactaga ccacattctt ggttcattcc tcaataattt   1800
gtaatcatat tggtggatat agaagtagat tggttataga tcagatagtg gaagacttta   1860
ggatgaattt cagctagttt ttttttttgg cttattgtct caaaagatta gtgctttgct   1920
gtctccattg cttctgctat cgacacgctt ctgtctcctt gtatctttat tatatctatt   1980
cgtcccatga gttttgtttg ttctgtattc gttcgctctg gtgtcatgga tggagtctct   2040
gttccatgtt tctgtaatgc atgttgggtt gtttcatgca agaaatgctg agataaacac   2100
tcatttgtga agtttctaa  actctgaatc gcgctacagg caatgctccg aggagtagga   2160
ggagaagaac gaaccaaacg acattatcag cccctttgagg aagctcttag ttttgttatt   2220 gttttttgtag ccaaattctc cattcttatt ccattttcac ttatctcttg ttccttatag   2280
accttataag ttttttattc atgtatacaa attatattgt catcaagaag tatctttaaa   2340
atctaaatct caaatcacca ggactatgtt tttgtccaat tcgtggaacc aacttgcagc   2400
ttgtatccat tctcttaacc aataaaaaaa gaaagaaaga tcaatttgat aaatttctca   2460
gccacaaatt ctacatttag gttttagcat atcgaaggct caatcacaaa tacaatagat   2520
agactagaga ttccagcgtc acgtgagttt tatctataaa taaaggacca aaaatcaaat   2580
cccgagggca ttttcgtaat ccaacataaa acccttaaac ttcaagtctc atttttaaac   2640
aaatcatgtt cacaagtctc ttcttcttct ctgtttctct atctcttgct catctttctc   2700
ctgaaccatg gcggcggcaa caacaacaac aacaacatct tcttcgatct ccttctccac   2760
caaaccatct cctccctcct ccaaatcacc attaccaatc tccagattct ccctcccatt   2820
ctccctaaac cccaacaaat catcctcctc ctcccgccgc cgcggtatca aatccagctc   2880
tccctcctcc atctccgccg tgctcaacac aaccaccaat gtcacaacca ctccctctcc   2940
aaccaaacct accaaacccg aaacattcat ctcccgattc gctccagatc aacccgcaa    3000
```

```
aggcgctgat atcctcgtcg aagctttaga acgtcaaggc gtagaaaccg tattcgctta    3060
ccctggaggt gcatcaatgg agattcacca agccttaacc cgctcttcct caatccgtaa    3120
cgtccttcct cgtcacgaac aaggaggtgt attcgcagca aaggatacg ctcgatcctc     3180
aggtaaacca ggtatctgta tagccacttc aggtcccgga gctacaaatc tcgttagcgg    3240
attagccgat gcgttgttag atagtgttcc tcttgtagca atcacaggac aagtccctcg    3300
tcgtatgatt ggtacagatg cgtttcaaga gactccgatt gttgaggtaa cgcgttcgat    3360
tacgaagcat aactatcttg tgatggatgt tgaagatatc cctaggatta ttgaggaagc    3420
tttcttttta gctacttctg gtagacctgg acctgttttg gttgatgttc ctaaagatat    3480
tcaacaacag cttgcgattc ctaattggga acaggctatg agattacctg gttatatgtc    3540
taggatgcct aaacctccgg aagattctca tttggagcag attgttaggt tgatttctga    3600
gtctaagaag cctgtgttgt atgttggtgg tggttgtttg aattctagcg atgaattggg    3660
taggtttgtt gagcttacgg ggatccctgt tgcgagtacg ttgatggggc tgggatctta    3720
tccttgtgat gatgagttgt cgttacatat gcttggaatg catgggactg tgtatgcaaa    3780
ttacgctgtg gagcatagtg atttgttgtt ggcgtttggg gtaaggtttg atgatcgtgt    3840
cacgggtaag cttgaggctt ttgctagtag ggctaagatt gttcatattg atattgactc    3900
ggctgagatt gggaagaata agactcctca tgtgtctgtg tgtggtgatg ttaagctggc    3960
tttgcaaggg atgaataagg ttcttgagaa ccgagcggag gagcttaagc ttgattttgg    4020
agtttggagg aatgagttga acgtacagaa acagaagttt ccgttgagct ttaagacgtt    4080
tggggaagct attcctccac agtatgcgat taaggtcctt gatgagttga ctgatggaaa    4140
agccataata agtactggtg tcgggcaaca tcaaatgtgg gcggcgcagt tctacaatta    4200
caagaaacca aggcagtggc tatcatcagg aggccttgga gctatgggat ttggacttcc    4260
tgctgcgatt ggagcgtctg ttgctaaccc tgatgcgata gttgtggata ttgacggaga    4320
tggaagcttt ataatgaatg tgcaagagct agccactatt cgtgtagaga atcttccagt    4380
gaaggtactt ttattaaaca accagcatct tggcatggtt atgcaatggg aagatcggtt    4440
ctacaaagct aaccgagctc acacatttct cggggatccg gctcaggagg acgagatatt    4500
cccgaacatg ttgctgtttg cagcagcttg cgggattcca gcggcgaggg tgacaaagaa    4560
agcagatctc cgagaagcta ttcagacaat gctggataca ccaggacctt acctgttgga    4620
tgtgatttgt ccgcaccaag aacatgtgtt gccgatgatc ccgaatggtg cactttcaa    4680
cgatgtcata acgaaggag atggccggat taaatactga gagatgaaac cggtgattat     4740
cagaaccttt tatggtcttt gtatgcatat ggtaaaaaaa cttagtttgc aatttcctgt    4800
ttgtttttggt aatttgagtt tcttttagtt gttgatctgc ctgcttttg gtttacgtca    4860
gactactact gctgttgttg tttggtttcc tttctttcat tttataaata aataatccgg    4920
ttcggtttac tccttgtgac tggctcagtt tggttattgc gaaatgcgaa tggtaaattg    4980
agtaattgaa attcgttatt agggttctaa gctgtttaa cagtcactgg gttaatatct     5040
ctcgaatctt gcatggaaaa tgctcttacc attggttttt aattgaaatg tgctcatatg    5100
ggccgtggtt tccaaattaa ataaaactac gatgtcatcg agaagtaaaa tcaactgtgt    5160
ccacattatc agtttgtgt atacgatgaa atagggtaat tcaaaatcta gcttgatatg     5220
ccttttggtt catttttaacc ttctgtaaac attttttcag attttgaaca agtaaatcca   5280
aaaaaaaaaa aaaaaaatct caactcaaca ctaaattatt ttaatgtata aaagatgctt    5340
aaaacatttg gcttaaaaga aagaagctaa aaacatagag aactcttgta aattgaagta    5400
```

```
tgaaaatata ctgaattggg tattatatga attttctga tttaggattc acatgatcca    5460
aaaaggaaat ccagaagcac taatcagaca ttggaagtag gaatatttca aaaagttttt    5520 ttttttaag taagtgacaa agcttttaa aaatagaaa agaaactagt attaaagttg       5580
taaatttaat aaacaaaaga aatttttat atttttttcat ttcttttttcc agcatgaggt  5640 tatgatggca ggatgtggat ttcatttttt tccttttgat agcctttttaa ttgatctatt  5700 ataattgacg aaaaaatatt agttaattat agatatattt taggtagtat tagcaattta   5760
cacttccaaa agactatgta agttgtaaat atgatgcgtt gatctcttca tcattcaatg   5820
gttagtcaaa aaaataaaag cttaactagt aaactaaagt agtcaaaaat tgtactttag   5880
tttaaaatat tacatgaata atccaaaacg acatttatgt gaaacaaaaa caatatctag   5940
agtcgacctg caggcatgca agcttggcgc gccttaatta aaggcctgtt aacagcgctg   6000
ggcccgttta aactgaaggc gggaaacgac aatctgatcc aagctcaagc tgctctagca   6060
ttcgccattc aggctgcgca actgttggga agggcgatcg gtgcgggcct cttcgctatt   6120
acgccagctg gcgaaagggg gatgtgctgc aaggcgatta agttgggtaa cgccagggtt   6180
ttcccagtca cgacgttgta aaacgacggc cagtgccaag cttgcatgcc aattcccgat   6240
ctagtaacat agatgacacc gcgcgcgata atttatccta gtttgcgcgc tatattttgt   6300
tttctatcgc gtattaaatg tataattgcg ggactctaat cataaaaacc catctcataa   6360
ataacgtcat gcattacatg ttaattatta catgcttaac gtaattcaac agaaattata   6420
tgataatcat cgcaagaccg gcaacaggat tcaatcttaa gaaactttat tgccaaatgt   6480
ttgaacgatc ggggaaattc gagctcggta gcaattcccg aggctgtagc cgacgatggt   6540
gcgccaggag agttgttgat tcattgtttg cctccctgct gcggttttc accgaagttc    6600 atgccagtcc agcgtttttg cagcagaaaa gccgccgact tcggtttgcg gtcgcgagtg   6660
aagatccctt tcttgttacc gccaacgcgc aatatgcctt gcgaggtcgc aaaatcggcg   6720
aaattccata cctgttcacc gacgacggcg ctgacgcgat caaagacgcg gtgatacata   6780
tccagccatg cacactgata ctcttcactc cacatgtcgg tgtacattga gtgcagcccg   6840
gctaacgtat ccacgccgta ttcggtgatg ataatcggct gatgcagttt ctcctgccag   6900
gccagaagtt cttttccag taccttctct gccgtttcca atcgccgct ttggacatac     6960 catccgtaat aacggttcag gcacagcaca tcaaagagat cgctgatggt atcggtgtga   7020
gcgtcgcaga acattacatt gacgcaggtg atcggacgcg tcgggtcgag tttacgcgtt   7080
gcttccgcca gtggcgcgaa atattcccgt gcaccttgcg gacgggtatc cggttcgttg   7140
gcaatactcc acatcaccac gcttgggtgg ttttttgtcac gcgctatcag ctctttaatc  7200
gcctgtaagt gcgcttgctg agtttccccg ttgactgcct cttcgctgta cagttctttc   7260
ggcttgttgc ccgcttcgaa accaatgcct aaagagaggt taaagccgac agcagcagtt   7320
tcatcaatca ccacgatgcc atgttcatct gcccagtcga gcatctcttc agcgtaaggg   7380
taatgcgagg tacggtagga gttggcccca atccagtcca ttaatgcgtg gtcgtgcacc   7440
atcagcacgt tatcgaatcc tttgccacgc aagtccgcat cttcatgacg accaaagcca   7500
gtaaagtaga acggtttgtg gttaatcagg aactgttcgc ccttcactgc cactgaccgg   7560
atgccgacgc gaagcgggta gatatcacac tctgtctggc ttttggctgt gacgcacagt   7620
tcatagagat aaccttcacc cggttgccag aggtgcggat tcaccacttg caaagtcccg   7680
ctagtgcctt gtccagttgc aaccacctgt tgatccgcat cacgcagttc aacgctgaca   7740
tcaccattgg ccaccacctg ccagtcaaca gacgcgtggt tacagtcttg cgcgacatgc   7800
```

```
gtcaccacgg tgatatcgtc cacccaggtg ttcggcgtgg tgtagagcat tacgctgcga   7860
tggattccgg catagttaaa gaaatcatgg aagtaagact gcttttctt gccgttttcg    7920
tcggtaatca ccattcccgg cgggatagtc tgccagttca gttcgttgtt cacacaaacg   7980
gtgatacctg cacatcaaca aattttggtc atatattaga aaagttataa attaaaatat   8040
acacacttat aaactacaga aaagcaattg ctatatacta cattcttta ttttgaaaaa    8100
aatatttgaa atattatatt actactaatt aatgataatt attatatata tatcaaaggt   8160
agaagcagaa acttacgtac acttttcccg gcaataacat acggcgtgac atcggcttca   8220
aatggcgtat agccgccctg atgctccatc acttcctgat tattgaccca cactttgccg   8280
taatgagtga ccgcatcgaa acgcagcacg atacgctggc ctgcccaacc tttcggtata   8340
aagacttcgc gctgatacca gacgttgccc gcataattac gaatatctgc atcggcgaac   8400
tgatcgttaa aactgcctgg cacagcaatt gcccggcttt cttgtaacgc gctttcccac   8460
caacgctgac caattccaca gttttcgcga tccagactga atgcccacag gccgtcgagt   8520
tttttgattt cacgggttgg ggtttctaca ggacgtaaca taagggactg acctacccgg   8580
gagatcttcg atttggtgta tcgagattgg ttatgaaatt cagatgctag tgtaatgtat   8640
tggtaatttg gaagatata ataggaagca aggctattta tccatttctg aaaaggcgaa     8700
atggcgtcac cgcgagcgtc acgcgcattc cgttcttgct gtaaagcgtt gtttggtaca   8760
cttttgacta gcgaggcttg gcgtgtcagc gtatctattc aaaagtcgtt aatggctgcg   8820
gatcaagaaa aagttggaat agaaacagaa tacccgcgaa attcaggccc ggttgccatg   8880
tcctacacgc cgaaataaac gaccaaatta gtagaaaaat aaaaactgac tcggatactt   8940
acgtcacgtc ttgcgcactg atttgaaaaa tctccctcga tcgagaaaga gatcaatgtt   9000
gagctgcttc aaaagcaatg ggattgacca gctcgcggat cctacaggcc aaattcgctc   9060
ttagccgtac aatattactc accggtgcga tgcccccccat cgtaggtgaa ggtggaaatt   9120
aatgatccat cttgagacca caggcccaca acagctacca gtttcctcaa gggtccacca   9180
aaaacgtaag cgcttacgta catggtcgat aagaaaaggc aatttgtaga tgttaacatc   9240
caacgtcgct ttcagggatc ctacaggcca aattcgctct tagccgtaca atattactca   9300
ccggtgcgat gccccccatc gtaggtgaag gtggaaatta atgatccatc ttgagaccac   9360
aggcccacaa cagctaccag tttcctcaag ggtccaccaa aaacgtaagc gcttacgtac   9420
atggtcgata agaaaaggca atttgtagat gttaacatcc aacgtcgctt tcagggatcc   9480
tacaggccaa attcgctctt agccgtacaa tattactcac cggtgcgatg cccccccatcg   9540
taggtgaagg tggaaattaa tgatccatct tgagaccaca ggcccacaac agctaccagt   9600
ttcctcaagg gtccaccaaa aacgtaagcg cttacgtaca tggtcgataa gaaaaggcaa   9660
tttgtagatg ttaacatcca acgtcgcttt cagggatccg cgagcttatc gataccgtcg   9720
aatctagagt cgacctgcag gcatgcaagc ttggcgcgcc ttaattaaag gaaactatca   9780
gtgtttgaca ggatatattg gcgggtaaac ctaagagaaa agagcgttta ttagaataac   9840
ggatatttaa aagggcgtga aaaggtttat ccgttcgtcc atttgtatgt gcatgccaac   9900
cacagggttc ccctcgggat caaagtactt tgatccaacc cctccgctgc tatagtgcag   9960
tcggcttctg acgttcagtg cagccgtctt ctgaaaacga catgtcgcac aagtcctaag   10020
ttacgcgaca ggctgccgcc ctgcccttt cctggcgttt tcttgtcgcg tgttttagtc    10080
gcataaagta gaatacttgc gactagaacc ggagacatta cgccatgaac aagagcgccg   10140
ccgctggcct gctgggctat gcccgcgtca gcaccgacga ccaggacttg accaaccaac   10200
```

```
gggccgaact gcacgcggcc ggctgcacca agctgttttc cgagaagatc accggcacca   10260
ggcgcgaccg cccggagctg gccaggatgc ttgaccacct acgccctggc gacgttgtga   10320
cagtgaccag gctagaccgc ctggcccgca gcacccgcga cctactggac attgccgagc   10380
gcatccagga ggccggcgcg ggcctgcgta gcctggcaga gccgtgggcc gacaccacca   10440
cgccggccgg ccgcatggtg ttgaccgtgt cgccggcat tgccgagttc gagcgttccc    10500
taatcatcga ccgcacccgg agcgggcgcg aggccgccaa ggcccgaggc gtgaagtttg   10560
gcccccgccc taccctcacc ccggcacaga tcgcgcacgc ccgcgagctg atcgaccagg   10620
aaggccgcac cgtgaaagag gcggctgcac tgcttggcgt gcatcgctcg accctgtacc   10680
gcgcacttga gcgcagcgag gaagtgacgc ccaccgaggc caggcggcgc ggtgccttcc   10740
gtgaggacga attgaccgag gccgacgccc tggcggccgc cgagaatgaa cgccaagagg   10800
aacaagcatg aaaccgcacc aggacggcca ggacgaaccg tttttcatta ccgaagagat   10860
cgaggcggag atgatcgcgg ccgggtacgt gttcgagccg cccgcgcacg tctcaaccgt   10920
gcggctgcat gaaatcctgg ccggtttgtc tgatgccaag ctggcggcct ggccggccag   10980
cttggccgct gaagaaaccg agcgccgccg tctaaaaagg tgatgtgtat ttgagtaaaa   11040
cagcttgcgt catgcggtcg ctgcgtatat gatgcgatga gtaaataaac aaatacgcaa   11100
ggggaacgca tgaaggttat cgctgtactt aaccagaaag gcgggtcagg caagacgacc   11160
atcgcaaccc atctagcccg cgccctgcaa ctcgccgggg ccgatgttct gttagtcgat   11220
tccgatcccc agggcagtgc ccgcgattgg gcggccgtgc gggaagatca accgctaacc   11280
gttgtcggca tcgaccgccc gacgattgac cgcgacgtga aggccatcgg ccggcgcgac   11340
ttcgtagtga tcgacggagc gccccaggcg gcggacttgg ctgtgtccgc gatcaaggca   11400
gccgacttcg tgctgattcc ggtgcagcca agcccttacg acatatgggc cacccgccgac  11460 ctggtggagc tggttaagca gcgcattgag gtcacggatg gaaggctaca agcggccttt   11520
gtcgtgtcgc gggcgatcaa aggcacgcgc atcggcggtg aggttgccga ggcgctggcc   11580
gggtacgagc tgcccattct tgagtcccgt atcacgcagc gcgtgagcta cccaggcact   11640
gccgccgccg gcacaaccgt tcttgaatca gaacccgagg gcgacgctgc ccgcgaggtc   11700
caggcgctgg ccgctgaaat taaatcaaaa ctcatttgag ttaatgaggt aaagagaaaa   11760
tgagcaaaag cacaaacacg ctaagtgccg gccgtccgag cgcacgcagc agcaaggctg   11820
caacgttggc cagcctggca gacacgccag ccatgaagcg ggtcaacttt cagttgccgg   11880
cggaggatca caccaagctg aagatgtacg cggtacgcca aggcaagacc attaccgagc   11940
tgctatctga atacatcgcg cagctaccag agtaaatgag caaatgaata aatgagtaga   12000
tgaattttag cggctaaagg aggcggcatg gaaaatcaag aacaaccagg caccgacgcc   12060
gtggaatgcc ccatgtgtgg aggaacgggc ggttggccag gcgtaagcgg ctgggttgcc   12120
tgccggccct gcaatggcac tggaaccccc aagcccgagg aatcggcgtg agcggtcgca   12180
aaccatccgg cccggtacaa atcggcgcgg cgctgggtga tgacctggtg gagaagttga   12240
aggccgcgca ggccgcccag cggcaacgca tcgaggcaga agcacgcccc ggtgaatcgt   12300
ggcaagcggc cgctgatcga atccgcaaag aatcccggca accgccggca gccggtgcgc   12360
cgtcgattag gaagccgccc aagggcgacg agcaaccaga ttttttcgtt ccgatgctct   12420
atgacgtggg cacccgcgat agtcgcagca tcatggacgt ggccgttttc cgtctgtcga   12480
agcgtgaccg acgagctggc gaggtgatcc gctacgagct tccagacggg cacgtagagg   12540
tttccgcagg gccggccggc atggccagtg tgtgggatta cgacctggta ctgatggcgg   12600
```

```
tttcccatct aaccgaatcc atgaaccgat accgggaagg gaagggagac aagcccggcc   12660
gcgtgttccg tccacacgtt gcggacgtac tcaagttctg ccggcgagcc gatggcggaa   12720
agcagaaaga cgacctggta gaaacctgca ttcggttaaa caccacgcac gttgccatgc   12780
agcgtacgaa gaaggccaag aacgccgcc tggtgacggt atccgagggt gaagccttga    12840
ttagccgcta caagatcgta aagagcgaaa ccgggcggcc ggagtacatc gagatcgagc   12900
tagctgattg gatgtaccgc gagatcacag aaggcaagaa cccggacgtg ctgacggttc   12960
accccgatta cttttttgatc gatcccggca tcggccgttt tctctaccgc ctggcacgcc   13020
gcgccgcagg caaggcagaa gccagatggt tgttcaagac gatctacgaa cgcagtggca   13080
gcgccggaga gttcaagaag ttctgtttca ccgtgcgcaa gctgatcggg tcaaatgacc   13140
tgccggagta cgatttgaag gaggaggcgg ggcaggctgg cccgatccta gtcatgcgct   13200
accgcaacct gatcgagggc gaagcatccg ccggttccta atgtacggag cagatgctag   13260
ggcaaattgc cctagcaggg gaaaaaggtc gaaaaggtct cttccctgtg gatagcacgt   13320
acattgggaa cccaaagccg tacattggga accggaaccc gtacattggg aacccaaagc   13380
cgtacattgg gaaccggtca cacatgtaag tgactgatat aaaagagaaa aaaggcgatt   13440
tttccgccta aaactcttta aaacttatta aaactcttaa aacccgcctg gcctgtgcat   13500
aactgtctgg ccagcgcaca gccgaagagc tgcaaaaagc gcctacccttcggtcgctgc   13560
gctccctacg ccccgccgct tcgcgtcggc ctatcgcggc cgctggccgc tcaaaaatgg   13620
ctggcctacg gccaggcaat ctaccagggc gcggacaagc cgcgccgtcg ccactcgacc   13680
gccggcgccc acatcaaggc accctgcctc gcgcgtttcg gtgatgacgg tgaaaacctc   13740
tgacacatgc agctcccgga gacggtcaca gcttgtctgt aagcggatgc cgggagcaga   13800
caagcccgtc agggcgcgtc agcgggtgtt ggcgggtgtc ggggcgcagc catgacccag   13860
tcacgtagcg atagcggagt gtatactggc ttaactatgc ggcatcagag cagattgtac   13920
tgagagtgca ccatatgcgg tgtgaaatac cgcacagatg cgtaaggaga aaataccgca   13980
tcaggcgctc ttccgcttcc tcgctcactg actcgctgcg ctcggtcgtt cggctgcggc   14040
gagcggtatc agctcactca aaggcggtaa tacggttatc cacagaatca ggggataacg   14100
caggaaagaa catgtgagca aaaggccagc aaaaggccag gaaccgtaaa aaggccgcgt   14160
tgctggcgtt tttccatagg ctccgccccc ctgacgagca tcacaaaaat cgacgctcaa   14220
gtcagaggtg gcgaaacccg acaggactat aaagatacca ggcgtttccc cctggaagct   14280
ccctcgtgcg ctctcctgtt ccgacccgtgc cgcttaccgg ataccgtgtcc gcctttctcc   14340
cttcgggaag cgtggcgctt tctcatagct cacgctgtag gtatctcagt tcggtgtagg   14400
tcgttcgctc caagctgggc tgtgtgcacg aaccccccgt tcagcccgac cgctgcgcct   14460
tatccggtaa ctatcgtctt gagtccaacc cggtaagaca cgacttatcg ccactggcag   14520
cagccactgg taacaggatt agcagagcga ggtatgtagg cggtgctaca gagttcttga   14580
agtggtggcc taactacggc tacactagaa ggacagtatt tggtatctgc gctctgctga   14640
agccagttac cttcggaaaa agagttggta gctcttgatc cggcaaacaa accaccgctg   14700
gtagcggtgg ttttttttgtt tgcaagcagc agattacgcg cagaaaaaaa ggatctcaag   14760
aagatccttt gatcttttct acggggtctg acgctcagtg gaacgaaaac tcacgttaag   14820
ggctgatgaa tcccctaatg attttttatca aaatcattaa gttaaggtag atacacatct   14880
tgtcatatga tcaaatggtt tcgccaaaaa tcaataatca gacaacaaaa tgtgcgaact   14940
cgatatttta cacgactctc tttaccaatt ctgccccgaa ttacacttaa aacgactcaa   15000
```

```
cagcttaacg ttggcttgcc acgccttact tgactgtaaa actctcactc ttaccgaact    15060
tggccgtaac ctgccaacca aagcgagaac aaaacataac atcaaacgaa tcgaccgatt    15120
gttaggtaat cgtcacctcc acaaagagcg actcgctgta taccgttggc atgctagctt    15180
tatctgttcg ggcaatacga tgcccattgt acttgttgac tggtctgata ccgtgagca    15240 aaaacggctt atggtattgc gagcttcagt cgcactacac ggtcgttctg ttactcttta    15300
tgagaaagcg ttcccgcttt cagagcaatg ttcaaagaaa gctcatgacc aatttctagc    15360
cgaccttgcg agcattctac cgagtaacac cacaccgctc attgtcagtg atgctggctt    15420
taaagtgcca tggtatataat ccgttgagaa gctgggttgg tactggttaa gtcgagtaag    15480
aggaaaagta caatatgcag acctaggagc ggaaaactgg aaacctatca gcaacttaca    15540
tgatatgtca tctagtcact caaagacttt aggctataag aggctgacta aaagcaatcc    15600
aatctcatgc caaattctat tgtataaatc tcgctctaaa ggccgaaaaa atcagcgctc    15660
gacacggact cattgtcacc acccgtcacc taaaatctac tcagcgtcgg caaggagcc    15720 atggattcta gcaactaact tacctgttga aattcgaaca cccaaacaac ttgttaatat    15780
ctattcgaag cgaatgcaga ttgaagaaac cttccgagac ttgaaaagtc ctgcctacgg    15840
actaggccta cgccatagcc gaacgagcag ctcagagcgt tttgatatca tgctgctaat    15900
cgccctgatg cttcaactaa catgttggct tgcgggcgtt catgctcaga acaaggttg    15960 ggacaagcac ttccaggcta acacagtcag aaatcgaaac gtactctcaa cagttcgctt    16020
aggcatggaa gttttgcggc attctggcta cacaataaca agggaagact tactcgtggc    16080
tgcaacccta ctagctcaaa atttattcac acatggttac gctttgggga aattatgagg    16140
ggatctctca gcgttaaggg attttggtca tgcattctag gtactaaaac aattcatcca    16200
gtaaaatata atattttatt ttctcccaat caggcttgat ccccagtaag tcaaaaaata    16260
gctcgacata ctgttcttcc ccgatatcct ccctgatcga ccggacgcag aaggcaatgt    16320
cataccactt gtccgccctg ccgcttctcc caagatcaat aaagccactt actttgccat    16380
ctttcacaaa gatgttgctg tctcccaggt cgccgtggga aaagacaagt tcctcttcgg    16440
gcttttccgt ctttaaaaaa tcatacagct cgcgcggatc tttaaatgga gtgtcttctt    16500
cccagttttc gcaatccaca tcggccagat cgttattcag taagtaatcc aattcggcta    16560
agcggctgtc taagctattc gtatagggac aatccgatat gtcgatggag tgaaagagcc    16620
tgatgcactc cgcatacagc tcgataatct tttcagggct ttgttcatct tcatactctt    16680
ccgagcaaag gacgccatcg gcctcactca tgagcagatt gctccagcca tcatgccgtt    16740
caaagtgcag gacctttgga acaggcagct ttccttccag ccatagcatc atgtccttt    16800 cccgttccac atcataggtg gtccctttat accggctgtc cgtcattttt aaatataggt    16860
tttcattttc tcccaccagc ttatatacct tagcaggaga cattccttcc gtatcttta    16920 cgcagcggta tttttcgatc agtttttca attccggtga tattctcatt ttagccattt    16980
attatttcct tcctctttc tacagtattt aaagataccc caagaagcta attataacaa    17040
gacgaactcc aattcactgt tccttgcatt ctaaaaccttaaataccaga aaacagcttt    17100 ttcaaagttg ttttcaaagt tggcgtataa catagtatcg acggagccga ttttgaaacc    17160
gcggtgatca caggcagcaa cgctctgtca tcgttacaat caacatgcta ccctccgcga    17220
gatcatccgt gtttcaaacc cggcagctta gttgccgttc ttccgaatag catcggtaac    17280
atgagcaaag tctgccgcct tacaacggct ctcccgctga cgccgtcccg gactgatggg    17340
ctgcctgtat cgagtggtga ttttgtgccg agctgccggt cggggagctg ttggct        17396
```

<210> SEQ ID NO 3
<211> LENGTH: 11070
<212> TYPE: DNA
<213> ORGANISM: Unknown
<220> FEATURE:
<223> OTHER INFORMATION: vector pBPSLM003

<400> SEQUENCE: 3

| | | | | | |
|---|---|---|---|---|---|
| actttgatcc | aaccccctccg | ctgctatagt | gcagtcggct | tctgacgttc | agtgcagccg | 60 |
| tcttctgaaa | acgacatgtc | gcacaagtcc | taagttacgc | gacaggctgc | cgccctgccc | 120 |
| ttttcctggc | gttttcttgt | cgcgtgtttt | agtcgcataa | agtagaatac | ttgcgactag | 180 |
| aaccggagac | attacgccat | gaacaagagc | gccgccgctg | gcctgctggg | ctatgcccgc | 240 |
| gtcagcaccg | acgaccagga | cttgaccaac | caacgggccg | aactgcacgc | ggccggctgc | 300 |
| accaagctgt | tttccgagaa | gatcaccggc | accaggcgcg | accgcccgga | gctggccagg | 360 |
| atgcttgacc | acctacgccc | tggcgacgtt | gtgacagtga | ccaggctaga | ccgcctggcc | 420 |
| cgcagcaccc | gcgacctact | ggacattgcc | gagcgcatcc | aggaggccgg | cgcgggcctg | 480 |
| cgtagcctgg | cagagccgtg | ggccgacacc | accacgccgg | ccggccgcat | ggtgttgacc | 540 |
| gtgttcgccg | gcattgccga | gttcgagcgt | tccctaatca | tcgaccgcac | ccggagcggg | 600 |
| cgcgaggccg | ccaaggcccg | aggcgtgaag | tttggccccc | gccctaccct | caccccggca | 660 |
| cagatcgcgc | acgcccgcga | gctgatcgac | caggaaggcc | gcaccgtgaa | agaggcggct | 720 |
| gcactgcttg | gcgtgcatcg | ctcgaccctg | taccgcgcac | ttgagcgcag | cgaggaagtg | 780 |
| acgcccaccg | aggccaggcg | gcgcggtgcc | ttccgtgagg | acgcattgac | cgaggccgac | 840 |
| gccctggcgg | ccgccgagaa | tgaacgccaa | gaggaacaag | catgaaaccg | caccaggacg | 900 |
| gccaggacga | accgttttc | attaccgaag | agatcgaggc | ggagatgatc | gcggccgggt | 960 |
| acgtgttcga | gccgcccgcg | cacgtctcaa | ccgtgcggct | gcatgaaatc | ctggccggtt | 1020 |
| tgtctgatgc | caagctggcg | gcctggccgg | ccagcttggc | cgctgaagaa | accgagcgcc | 1080 |
| gccgtctaaa | aaggtgatgt | gtatttgagt | aaaacagctt | gcgtcatgcg | gtcgctgcgt | 1140 |
| atatgatgcg | atgagtaaat | aaacaaatac | gcaaggggaa | cgcatgaagg | ttatcgctgt | 1200 |
| acttaaccag | aaaggcgggt | caggcaagac | gaccatcgca | acccatctag | cccgcgccct | 1260 |
| gcaactcgcc | ggggccgatg | ttctgttagt | cgattccgat | ccccagggca | gtgcccgcga | 1320 |
| ttgggcggcc | gtgcgggaag | atcaaccgct | aaccgttgtc | ggcatcgacc | gcccgacgat | 1380 |
| tgaccgcgac | gtgaaggcca | tcggccggcg | cgacttcgta | gtgatcgacg | gagcgcccca | 1440 |
| ggcggcggac | ttggctgtgt | ccgcgatcaa | ggcagccgac | ttcgtgctga | ttccggtgca | 1500 |
| gccaagccct | tacgacatat | gggccaccgc | cgacctggtg | gagctggtta | agcagcgcat | 1560 |
| tgaggtcacg | gatggaaggc | tacaagcggc | ctttgtcgtg | tcgcgggcga | tcaaaggcac | 1620 |
| gcgcatcggc | ggtgaggttg | ccgaggcgct | ggccgggtac | gagctgccca | ttcttgagtc | 1680 |
| ccgtatcacg | cagcgcgtga | gctacccagg | cactgccgcc | gccggcacaa | ccgttcttga | 1740 |
| atcagaaccc | gagggcgacg | ctgccgcgca | ggtccaggcg | ctggccgctg | aaattaaatc | 1800 |
| aaaactcatt | tgagttaatg | aggtaaagag | aaaatgagca | aaagcacaaa | cacgctaagt | 1860 |
| gccgccgtc | cgacgcacg | cagcagcaag | gctgcaacgt | tggccagcct | ggcagacacg | 1920 |
| ccagccatga | agcgggtcaa | ctttcagttg | ccggcggagg | atcacaccaa | gctgaagatg | 1980 |
| tacgcggtac | gccaaggcaa | gaccattacc | gagctgctat | ctgaatacat | cgcgcagcta | 2040 |
| ccagagtaaa | tgagcaaatg | aataaatgag | tagatgaatt | ttagcggcta | aaggaggcgg | 2100 |

```
catggaaaat caagaacaac caggcaccga cgccgtggaa tgccccatgt gtggaggaac    2160
gggcggttgg ccaggcgtaa gcggctgggt tgtctgccgg ccctgcaatg gcactggaac    2220
ccccaagccc gaggaatcgg cgtgacggtc gcaaaccatc cggcccggta caaatcggcg    2280
cggcgctggg tgatgacctg gtggagaagt tgaaggccgc gcaggccgcc cagcggcaac    2340
gcatcgaggc agaagcacgc cccggtgaat cgtggcaagc ggccgctgat cgaatccgca    2400
aagaatcccg gcaaccgccg gcagccggtg cgccgtcgat taggaagccg cccaagggcg    2460
acgagcaacc agatttttc gttccgatgc tctatgacgt gggcacccgc gatagtcgca    2520
gcatcatgga cgtggccgtt ttccgtctgt cgaagcgtga ccgacgagct ggcgaggtga    2580
tccgctacga gcttccagac gggcacgtag aggtttccgc agggccggcc ggcatggcca    2640
gtgtgtggga ttacgacctg gtactgatgg cggtttccca tctaaccgaa tccatgaacc    2700
gataccggga agggaaggga gacaagcccg gccgcgtgtt ccgtccacac gttgcggacg    2760
tactcaagtt ctgccggcga gccgatggcg gaaagcagaa agacgacctg gtagaaacct    2820
gcattcggtt aaacaccacg cacgttgcca tgcagcgtac gaagaaggcc aagaacggcc    2880
gcctggtgac ggtatccgag ggtgaagcct tgattagccg ctacaagatc gtaaagagcg    2940
aaaccgggcg gccggagtac atcgagatcg agctagctga ttggatgtac cgcgagatca    3000
cagaaggcaa gaaccggac gtgctgacgg ttcaccccga ttacttttg atcgatcccg    3060
gcatcggccg ttttctctac cgcctggcac gccgcgccgc aggcaaggca gaagccagat    3120
ggttgttcaa gacgatctac gaacgcagtg gcagcgccgg agagttcaag aagttctgtt    3180
tcaccgtgcg caagctgatc gggtcaaatg acctgccgga gtacgatttg aaggaggagg    3240
cggggcaggc tggcccgatc ctagtcatgc gctaccgcaa cctgatcgag ggcgaagcat    3300
ccgccggttc ctaatgtacg gagcagatgc tagggcaaat tgccctagca ggggaaaaag    3360
gtcgaaaagg tctctttcct gtggatagca cgtacattgg gaacccaaag ccgtacattg    3420
ggaaccggaa cccgtacatt gggaacccaa agccgtacat tgggaaccgg tcacacatgt    3480
aagtgactga tataaagag aaaaaggcg atttttccgc ctaaaactct ttaaaactta    3540
ttaaaactct taaacccgc ctggcctgtg cataactgtc tggccagcgc acagccgaag    3600
agctgcaaaa agcgcctacc cttcggtcgc tgcgctccct acgccccgcc gcttcgcgtc    3660
ggcctatcgc ggccgctggc cgctcaaaaa tggctggcct acggcaggc aatctaccag    3720
ggcgcggaca agccgcgccg tcgccactcg accgccggcg cccacatcaa ggcaccctgc    3780
ctcgcgcgtt tcggtgatga cggtgaaaac ctctgacaca tgcagctccc ggagacggtc    3840
acagcttgtc tgtaagcgga tgccgggagc agacaagccc gtcagggcgc gtcagcgggt    3900
gttggcgggt gtcggggcgc agccatgacc cagtcacgta gcgatagcgg agtgtatact    3960
ggcttaacta tgcggcatca gagcagattg tactgagagt gcaccatatg cggtgtgaaa    4020
taccgcacag atgcgtaagg agaaaatacc gcatcaggcg ctcttccgct tcctcgctca    4080
ctgactcgct gcgctcggtc gttcggctgc ggcgagcggt atcagctcac tcaaaggcgg    4140
taatacggtt atccacagaa tcaggggata acgcaggaaa gaacatgtga gcaaaaggcc    4200
agcaaaaggc caggaaccgt aaaaaggccg cgttgctggc gttttccat aggctccgcc    4260
cccctgacga gcatcacaaa aatcgacgct caagtcagag gtggcgaaac ccgacaggac    4320
tataaagata ccaggcgttt ccccctggaa gctccctcgt gcgctctcct gttccgaccc    4380
tgccgcttac cggatacctg tccgcctttc tcccttcggg aagcgtggcg ctttctcata    4440
gctcacgctg taggtatctc agttcggtgt aggtcgttcg ctccaagctg ggctgtgtgc    4500
```

```
acgaacccco cgttcagccc gaccgctgcg ccttatccgg taactatcgt cttgagtcca    4560
acccggtaag acacgactta tcgccactgg cagcagccac tggtaacagg attagcagag    4620
cgaggtatgt aggcggtgct acagagttct tgaagtggtg gcctaactac ggctacacta    4680
gaaggacagt atttggtatc tgcgctctgc tgaagccagt taccttcgga aaaagagttg    4740
gtagctcttg atccggcaaa caaaccaccg ctggtagcgg tggttttttt gtttgcaagc    4800
agcagattac gcgcagaaaa aaggatctc aagaagatcc tttgatcttt tctacggggt    4860
ctgacgctca gtggaacgaa aactcacgtt aagggatttt ggtcatgcat tctaggtact    4920
aaaacaattc atccagtaaa atataatatt ttatttctc ccaatcaggc ttgatcccca    4980
gtaagtcaaa aaatagctcg acatactgtt cttccccgat atcctccctg atcgaccgga    5040
cgcagaaggc aatgtcatac cacttgtccg ccctgccgct tctcccaaga tcaataaagc    5100
cacttacttt gccatctttc acaaagatgt tgctgtctcc caggtcgccg tgggaaaaga    5160
caagttcctc tcgggctttt tccgtcttta aaaaatcata cagctcgcgc ggatctttaa    5220
atggagtgtc ttcttcccag ttttcgcaat ccacatcggc cagatcgtta ttcagtaagt    5280
aatccaattc ggctaagcgg ctgtctaagc tattcgtata gggacaatcc gatatgtcga    5340
tggagtgaaa gagcctgatg cactccgcat acagctcgat aatcttttca gggctttgtt    5400
catcttcata ctcttccgag caaaggacgc catcggcctc actcatgagc agattgctcc    5460
agccatcatg ccgttcaaag tgcaggacct ttggaacagg cagctttcct tccagccata    5520
gcatcatgtc cttttcccgt tccacatcat aggtggtccc tttataccgg ctgtccgtca    5580
tttttaaata taggttttca ttttctccca ccagcttata taccttagca ggagacattc    5640
cttccgtatc ttttacgcag cggtattttt cgatcagttt tttcaattcc ggtgatattc    5700
tcattttagc catttattat ttccttcctc ttttctacag tatttaaaga taccccaaga    5760
agctaattat aacaagacga actccaattc actgttcctt gcattctaaa accttaaata    5820
ccagaaaaca gctttttcaa agttgttttc aaagttggcg tataacatag tatcgacgga    5880
gccgattttg aaaccgcggt gatcacaggc agcaacgctc tgtcatcgtt acaatcaaca    5940
tgctaccctc cgcgagatca tccgtgtttc aaacccggca gcttagttgc cgttcttccg    6000
aatagcatcg gtaacatgag caaagtctgc cgccttacaa cggctctccc gctgacgccg    6060
tcccggacta atgggctgcc tgtatcgagt ggtgattttg tgccgagctg ccggtcgggg    6120
agctgttggc tggctggtgg caggatatat tgtggtgtaa acaaattgac gcttagacaa    6180
cttaataaca cattgcggac gttttttaatg tactgaatta acgccgaatt aagcttggac    6240
aatcagtaaa ttgaacggag aatattattc ataaaaatac gatagtaacg ggtgatatat    6300
tcattagaat gaaccgaaac cggcggtaag gatctgagct acacatgctc aggttttta    6360
caacgtgcac aacagaattg aaagcaaata tcatgcgatc ataggcgtct cgcatatctc    6420
attaaagcag ggcatgccgg tcgagtcaaa tctcggtgac gggcaggacc ggacggggcg    6480
gtaccggcag gctgaagtcc agctgccaga aacccacgtc atgccagttc ccgtgcttga    6540
agccggccgc ccgcagcatg ccgcgggggg catatccgag cgcctcgtgc atgcgcacgc    6600
tcgggtcgtt gggcagcccg atgacagcga ccacgctctt gaagccctgt gcctccaggg    6660
acttcagcag gtgggtgtag agcgtggagc ccagtcccgt ccgctggtgg cgggggaga    6720
cgtacacggt cgactcggcc gtccagtcgt aggcgttgcg tgccttccag ggcccgcgt    6780
aggcgatgcc ggcgacctcg ccgtccacct cggcgacgag ccaggatag cgctcccgca    6840
gacgacgag gtcgtccgtc cactcctgcg gttcctgcgg ctcggtacgg aagttgaccg    6900
```

```
tgcttgtctc gatgtagtgg ttgacgatgg tgcagaccgc cggcatgtcc gcctcggtgg      6960
cacggcggat gtcggccggg cgtcgttctg ggctcatggt agactcgacg gatccacgtg      7020
tggaagatat gaattttttt gagaaactag ataagattaa tgaatatcgg tgttttggtt      7080
ttttcttgtg gccgtctttg tttatattga gattttccaa atcagtgcgc aagacgtgac      7140
gtaagtatcc gagtcagttt ttattttttct actaatttgg tcgaagcttt gggcggatcc     7200
tctagattcg acggtatcga taagctcgcg gatccctgaa agcgacgttg gatgttaaca      7260
tctacaaatt gccttttctt atcgaccatg tacgtaagcg cttacgtttt tggtggaccc      7320
ttgaggaaac tggtagctgt tgtgggcctg tggtctcaag atggatcatt aatttccacc      7380
ttcacctacg atgggggggca tcgcaccggt gagtaatatt gtacggctaa gagcgaattt     7440
ggcctgtagg atccctgaaa gcgacgttgg atgttaacat ctacaaattg ccttttctta      7500
tcgaccatgt acgtaagcgc ttacgttttt ggtggaccct tgaggaaact ggtagctgtt      7560
gtgggcctgt ggtctcaaga tggatcatta atttccacct tcacctacga tgggggcat      7620 cgcaccggtg agtaatattg tacggctaag agcgaatttg gcctgtagga tccctgaaag      7680
cgacgttgga tgttaacatc tacaaattgc cttttcttat cgaccatgta cgtaagcgct      7740 tacgttttg gtggacccct gaggaaactg gtagctgttg tgggcctgtg gtctcaagat       7800
ggatcattaa tttccacctt cacctacgat gggggggcatc gcaccggtga gtaatattgt     7860
acggctaaga gcgaatttgg cctgtaggat ccgcgagctg gtcaatccca ttgcttttga      7920
agcagctcaa cattgatctc tttctcgatc gagggagatt tttcaaatca gtgcgcaaga     7980
cgtgacgtaa gtatccgagt cagttttat ttttctacta atttggtcgt ttatttcggc      8040
gtgtaggaca tggcaaccgg gcctgaattt cgcgggtatt ctgtttctat tccaactttt     8100
tcttgatccg cagccattaa cgacttttga atagatacgc tgacacgcca agcctcgcta      8160
gtcaaaagtg taccaaacaa cgcttttacag caagaacgga atgcgcgtga cgctcgcggt     8220
gacgccattt cgccttttca gaaatggata aatagccttg cttcctatta tatcttccca      8280
aattaccaat acattacact agcatctgaa tttcataacc aatctcgata caccaaatcg      8340
aagatctccc gggtggtcag tcccttatgt tacgtcctgt agaaacccca acccgtgaaa      8400
tcaaaaaact cgacggcctg tgggcattca gtctggatcg cgaaaactgt ggaattgatc      8460
agcgttggtg ggaaagcgcg ttacaagaaa gccgggcaat tgctgtgcca ggcagttttta    8520 acgatcagtt cgccgatgca gatattcgta attatgcggg caacgtctgg tatcagcgcg     8580
aagtctttat accgaaaggt tgggcaggcc agcgtatcgt gctgcgtttc gatgcggtca     8640
ctcattacgg caaagtgtgg gtcaataatc aggaagtgat ggagcatcag ggcggctata     8700
cgccatttga agccgatgtc acgccgtatg ttattgccgg gaaaagtgta cgtaagtttc     8760
tgcttctacc tttgatatat ataataat tatcattaat tagtagtaat ataatatttc      8820
aaatattttt ttcaaaataa agaatgtag tatatagcaa ttgcttttct gtagtttata       8880
agtgtgtata ttttaattta aactttttct aatatatgac caaaatttgt tgatgtgcag     8940
gtatcaccgt ttgtgtgaac aacgaactga actggcagac tatcccgccg ggaatggtga     9000
ttaccgacga aaacggcaag aaaaagcagt cttacttcca tgatttcttt aactatgccg     9060
gaatccatcg cagcgtaatg ctctacacca cgccgaacac ctgggtggac gatatcaccg     9120
tggtgacgca tgtcgcgcaa gactgtaacc acgcgtctgt tgactggcag gtggtggcca    9180
atggtgatgt cagcgttgaa ctgcgtgatg cggatcaaca ggtggttgca actggacaag     9240
gcactagcgg gactttgcaa gtggtgaatc cgcacctctg gcaaccgggt gaaggttatc     9300
```

```
tctatgaact gtgcgtcaca gccaaaagcc agacagagtg tgatatctac ccgcttcgcg    9360
tcggcatccg gtcagtggca gtgaagggcc aacagttcct gattaaccac aaaccgttct    9420
actttactgg ctttggtcgt catgaagatg cggacttacg tggcaaagga ttcgataacg    9480
tgctgatggt gcacgaccac gcattaatgg actggattgg ggccaactcc taccgtacct    9540
cgcattaccc ttacgctgaa gagatgctcg actgggcaga tgaacatggc atcgtggtga    9600
ttgatgaaac tgctgctgtc ggctttaacc tctctttagg cattggtttc gaagcgggca    9660
acaagccgaa agaactgtac agcgaagagg cagtcaacgg ggaaactcag caagcgcact    9720
tacaggcgat taaagagctg atagcgcgtg acaaaaacca cccaagcgtg gtgatgtgga    9780
gtattgccaa cgaaccggat acccgtccgc aagtgcacgg gaatatttcg ccactggcgg    9840
aagcaacgcg taaactcgac ccgacgcgtc cgatcacctg cgtcaatgta atgttctgcg    9900
acgctcacac cgataccatc agcgatctct ttgatgtgct gtgcctgaac cgttattacg    9960
gatggtatgt ccaaagcggc gatttggaaa cggcagagaa ggtactggaa aaagaacttc   10020
tggcctggca ggagaaactg catcagccga ttatcatcac cgaatacggc gtggatacgt   10080
tagccgggct gcactcaatg tacaccgaca tgtggagtga agagtatcag tgtgcatggc   10140
tggatatgta tcaccgcgtc tttgatcgcg tcagcgccgt cgtcggtgaa caggtatgga   10200
atttcgccga ttttgcgacc tcgcaaggca tattgcgcgt tggcggtaac aagaaaggga   10260
tcttcactcg cgaccgcaaa ccgaagtcgg cggcttttct gctgcaaaaa cgctggactg   10320
gcatgaactt cggtgaaaaa ccgcagcagg gaggcaaaca atgaatcaac aactctcctg   10380
gcgcaccatc gtcggctaca gcctcgggaa ttgctaccga gctcgaattt ccccgatcgt   10440
tcaaacattt ggcaataaag tttcttaaga ttgaatcctg ttgccggtct tgcgatgatt   10500
atcatataat ttctgttgaa ttacgttaag catgtaataa ttaacatgta atgcatgacg   10560
ttatttatga gatgggtttt tatgattaga gtcccgcaat tatacattta atacgcgata   10620
gaaaacaaaa tatagcgcgc aaactaggat aaattatcgc gcgcggtgtc atctatgtta   10680
ctagatcggg aattggcatg caagcttggc actggccgtc gttttacaac gtcgtgactg   10740
ggaaaaccct ggcgttaccc aacttaatcg ccttgcagca catcccccttt cgccagctg   10800
gcgtaatagc gaagaggccc gcaccgatcg cccttcccaa cagttgcgca gcctgaatgg   10860
cgaatgctag agcagcttga gcttggatca gattgtcgtt tcccgccttc agtttaaact   10920
atcagtgttt gacaggatat attggcgggt aaacctaaga gaaaagagcg tttattagaa   10980
taacggatat ttaaaagggc gtgaaaaggt ttatccgttc gtccatttgt atgtgcatgc   11040
caaccacagg gttcccctcg ggatcaaagt                                     11070
```